United States Patent
Kularatne et al.

(10) Patent No.: US 9,254,341 B2
(45) Date of Patent: Feb. 9, 2016

(54) METHODS OF MANUFACTURE OF PTEROYL-AMINO ACID-FLUORESCENT DYES

(71) Applicant: On Target Laboratories, LLC, West Lafayette, IN (US)

(72) Inventors: Sumith A. Kularatne, West Lafayette, IN (US); Pravin Gagare, West Lafayette, IN (US); Mohammad Noshi, West Lafayette, IN (US)

(*) Notice: Subject to any disclaimer, the term of this patent is extended or adjusted under 35 U.S.C. 154(b) by 0 days.

(21) Appl. No.: 14/046,916

(22) Filed: Oct. 4, 2013

(65) Prior Publication Data

US 2014/0275533 A1    Sep. 18, 2014

Related U.S. Application Data

(60) Provisional application No. 61/791,921, filed on Mar. 15, 2013.

(51) Int. Cl.
| | | |
|---|---|---|
| *C07D 475/00* | (2006.01) | |
| *A61K 49/00* | (2006.01) | |
| *G01N 33/569* | (2006.01) | |
| *G01N 33/566* | (2006.01) | |
| *G01N 33/50* | (2006.01) | |

(52) U.S. Cl.
CPC ......... *A61K 49/0052* (2013.01); *A61K 49/0032* (2013.01); *A61K 49/0034* (2013.01); *G01N 33/5091* (2013.01); *G01N 33/566* (2013.01); *G01N 33/56966* (2013.01)

(58) Field of Classification Search
CPC ..................................................... C07D 475/00
USPC ......................................................... 544/258
See application file for complete search history.

(56) References Cited

U.S. PATENT DOCUMENTS

| | | | |
|---|---|---|---|
| 4,337,339 | A | 6/1982 | Farina et al. |
| 6,534,041 | B1 | 3/2003 | Licha |
| 2007/0009434 | A1 | 1/2007 | Low |
| 2011/0286933 | A1 | 11/2011 | Hilderbrand |

FOREIGN PATENT DOCUMENTS

| | | |
|---|---|---|
| WO | 2012032068 | 3/2012 |
| WO | 2013126797 | 8/2013 |

OTHER PUBLICATIONS

PCT, Notification of Transmittal of the International Search Report and the Written Opinion of the International Searching Authority, or the Declaration, in International application No. PCT/US2013/063593, dated Feb. 18, 2014. (7 pages).
Yang et al., Characterization of the pH of Folate Receptor-Containing Endosomes and the Rate of Hydrolysis of Internalized Acid-Labile Folate-Drug Conjugates. J Pharmacol Exp. Ther, 321 (2): 462-468, (2007). [retrieved on Jan. 27, 2014]. Retrieved from the Internet. <URL: http://jpet.aspetjournals.org/content/321/462.full.pdf>. entire document.
Mahalingham et al., 329—Evaluation of pteroyl-amino acid-NIR dye conjugates for tumor targeted fluorescence guided surgery. 246th ACS National Meeting and Exposition, Sep. 8-12, 2013. Indianapolis, Indiana. [Retrieved on Jan. 31, 2014]. Retrieved from the Internet. <URL:http://abstracts.acs.org/chem/246nm/program/view.php>. entire document.
Moon, et al., Enhanced Tumor Detection Using a Folate Receptor-Targeted Near-Infrared Fluorochrome Conjugate, Center for Molecular Imaging Reserach, Massachusetts General Hospital, Harvard Medical School, Charlestown, MA, Jan. 22, 2003, Revised Mar. 3, 2003.
Milstein, et al., Statistical approach for detection and localization of a fluorescing mouse tumor in Intralipid, Applied Optics, vol. 44, No. 12, Apr. 20, 2005.

*Primary Examiner* — Douglas M Willis
(74) *Attorney, Agent, or Firm* — McAndrews, Held & Malloy Ltd

(57) ABSTRACT

The present invention discloses a process for preparing a compound having the formula

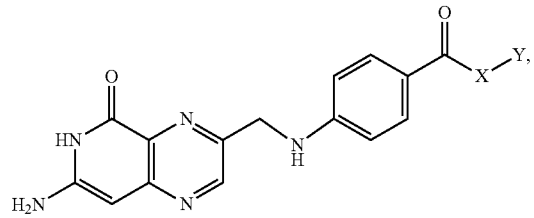

Including Reacting a compound of the formula 1:

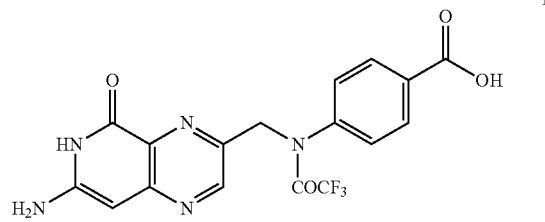

with a compound of the formula:

in the presence of a polar solvent and trifluoroacetic acid to provide a compound of the formula:
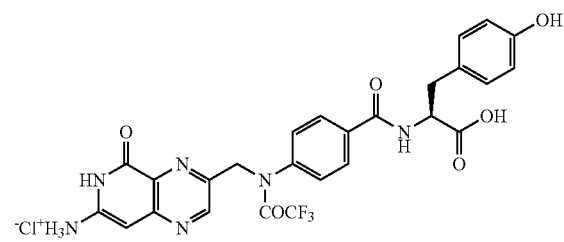
or
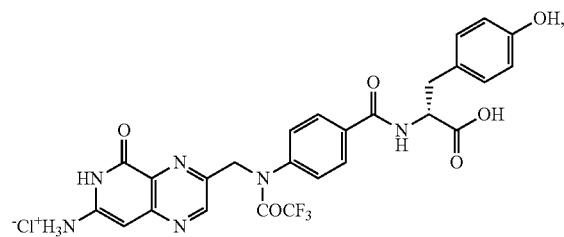
or a racemic mixture thereof; and further reacting the compound of the formula:
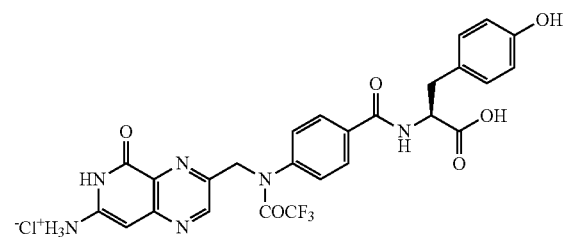
-continued
or
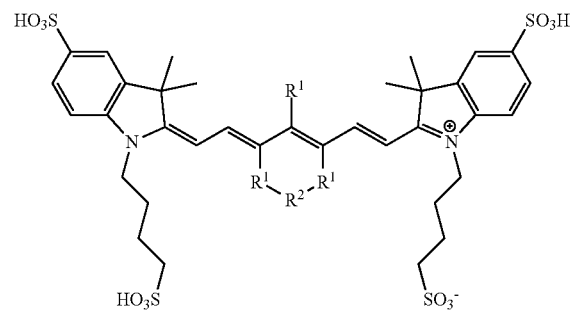
or a racemic mixture thereof; with sodium hydroxide and a compound of the formula:
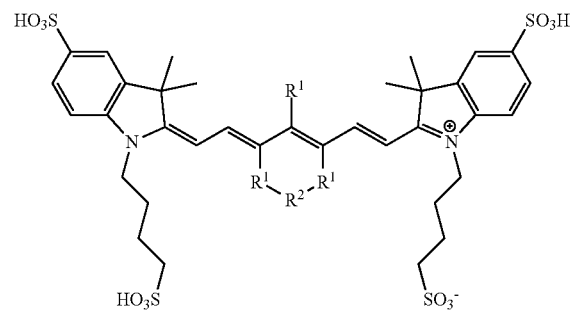
wherein
$R^1$ and $R^2$ are as defined above.
6 Claims, 17 Drawing Sheets

Figure 1 Rational of Pte-L-Tyr-S0456 (OTL-0038) NIR dye conjugate. Chemical structure of Pteroyl-Tyr-S0456 (OTL-0038) with four regions of functionality selected. (1) pterin derivative as a targeting molecule. (2) tyrosine to improve binding affinity for folate receptor. (3) phenolic moiety from tyrosine to enhance (brightness) fluorescence intensity. (4) near-IR fluorescent probe.

FIGURE 2A

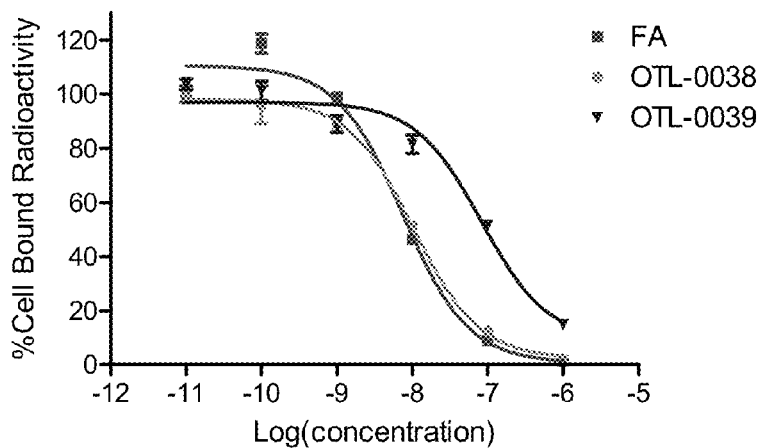

Figures 2A and 2B depict the relative binding affinity of OTL-0038, OTL-0039, and folic acid for folate receptors. Figure 2A is a plot which depicts the binding curve of each compound for folate receptors.

Figure 2B

| Test article | Binding affinity | Relative Binding Affinity |
|---|---|---|
| Folic acid | 7.4 | 1 |
| OTL-0038 | 10.4 | 0.7 |
| OTL-0039 | 81.8 | 0.09 |

Figure 2B is a table illustrating the binding affinity and relative binding affinity of all three compounds.

Figure 3A illustrates fluorescent images of nude mice with KB tumor xenografts 2 hours following intravenous injection of 10 nmol folate receptor targeted-NIR compounds (overlay of Fluorescent and white light images).

Figure 3B illustrates *ex vivo* tissue biodistribution of compounds following harvesting tissues from previously imaged mice of Figure 3A.

Figure 4A illustrates whole body fluorescent images of head-to-head comparison of Pte-L-Try-S0456 (OTL-0038) with 2nd generation folate-NIR compounds.

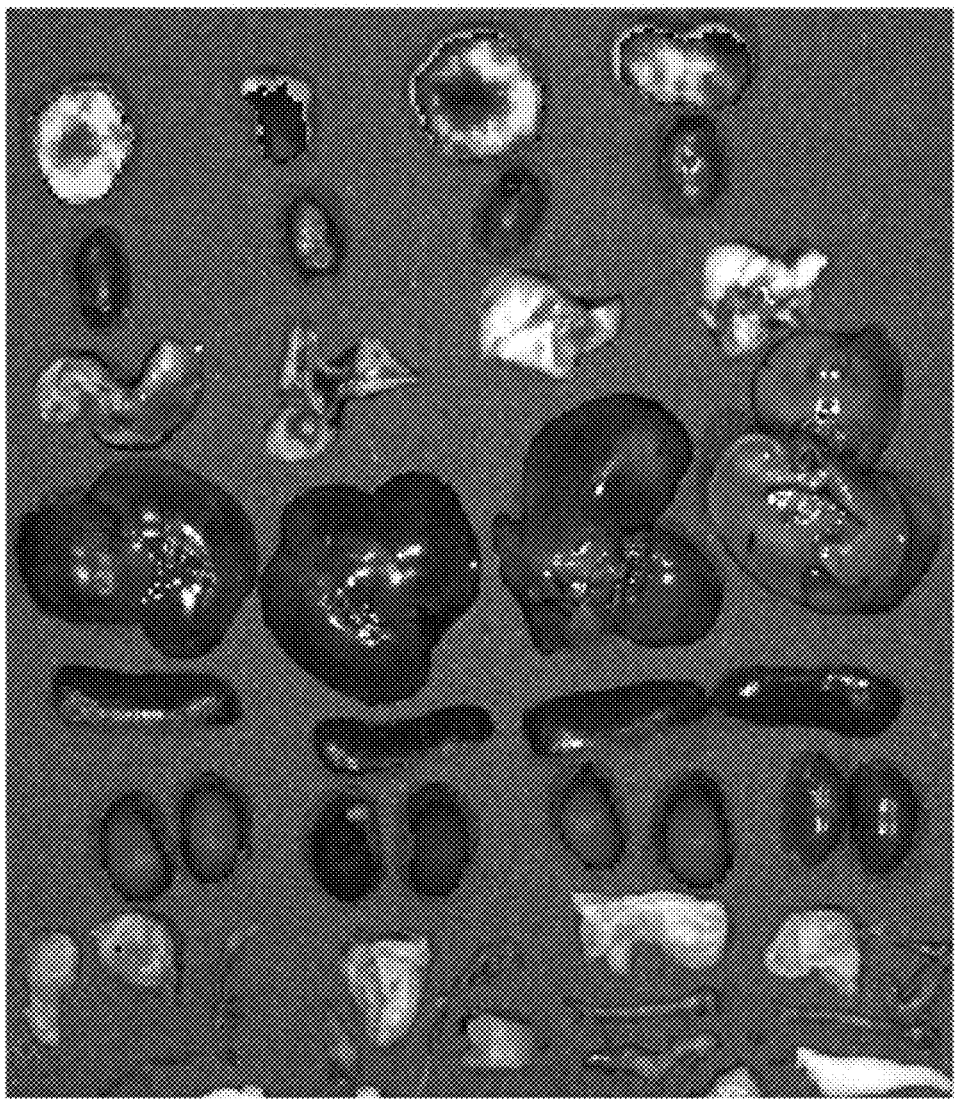
Figure 4B shows ex vivo tissue biodistribution illustrating head-to-head comparison of Pte-L-Try-S0456 (OTL-0038) with folate-ethylene diamine bridged-NIR conjugates. Dissected (sliced) tumors showed homogeneous uptake of the targeted imaging agents in the tumors.

Figure 4C shows Tumor and kidney images 2h after administering conjugates (10 nmol) to nude mice illustrating head-to-head comparison of Pte-L-Try-S0456 (OTL-0038) with folate-ethylene diamine bridged-NIR conjugates. Dissected (sliced) tumors showed homogeneous uptake of the targeted imaging agents in the tumors.

Figure 4D illustrates Folate-EDA-LS288 (OTL-0001).

Figure 4E illustrates Folate-EDA-IR800 (OTL-0002).

Figure 4F illustrates Folate-EDA-ZW800 (OTL-0003).

Figure 5 illustrates the whole body fluorescence imaging of nude mice with KB tumor xenografts injected with 1 nmol of OTL-0038 (1/10 of normal dose). After 2.5 hours, animals were euthanized by $CO_2$ asphyxiation. Whole body imaging experiments were then performed using a Caliper IVIS Lumina II Imaging Station with Living Image 4.0 software.

Figure 6 depicts the whole body fluorescence image of mice bearing tumor xenografts negative for folate receptors (A549 tumor xenografts). Whole body imaging was performed 2.5 hours after administration of 10 nmol of OTL-0038.

Figure 7 illustrates invasive tumor and kidney uptake of OTL-0038, by folate receptor – negative tumor xenografts (A549 tumor xenografts) and folate receptor – positive kidneys. Data analysis was performed 2.5 hours post injection.

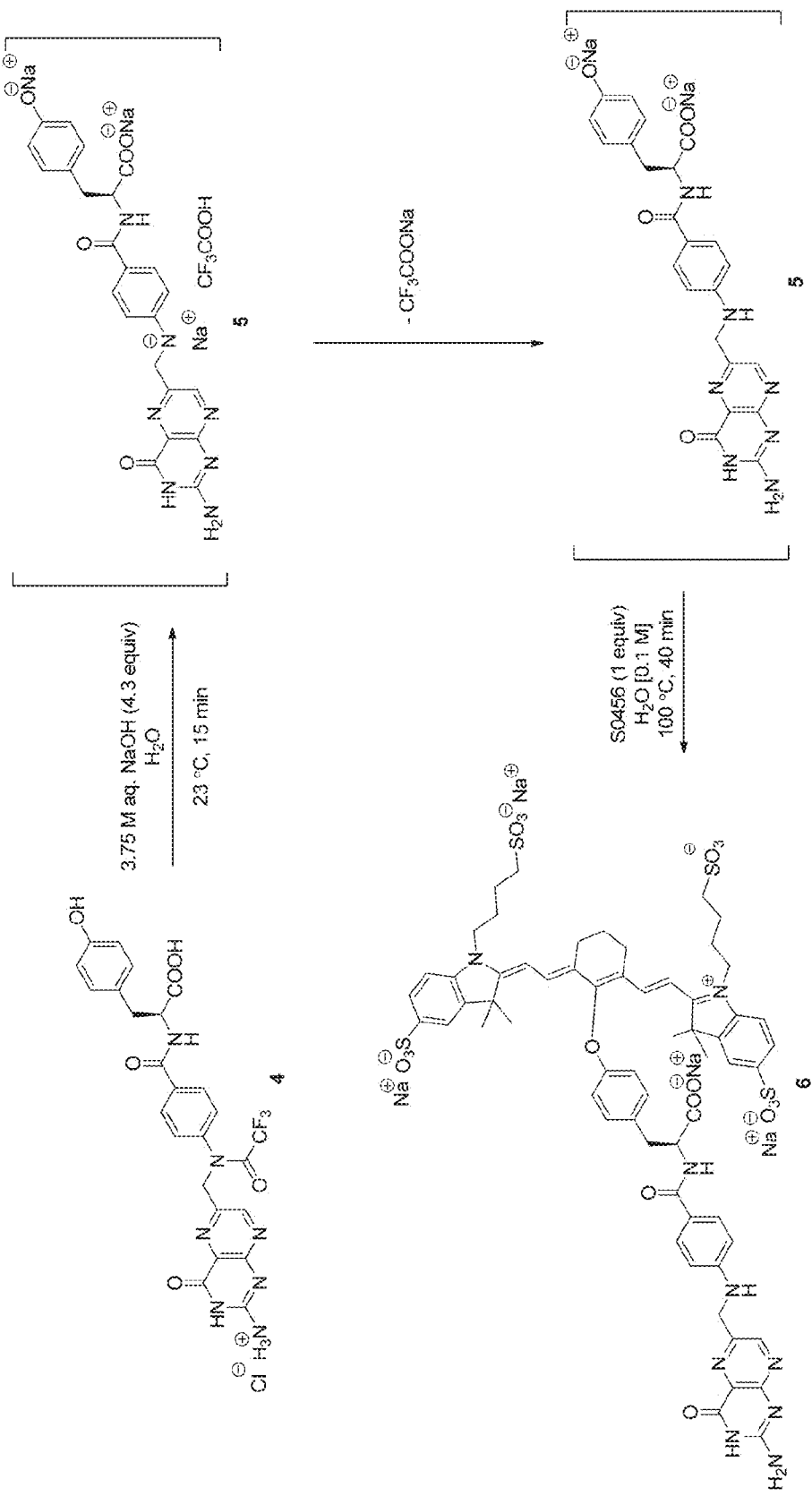
Figure 8 depicts a 3 step reaction schematic for solution phase synthesis of imaging compounds.

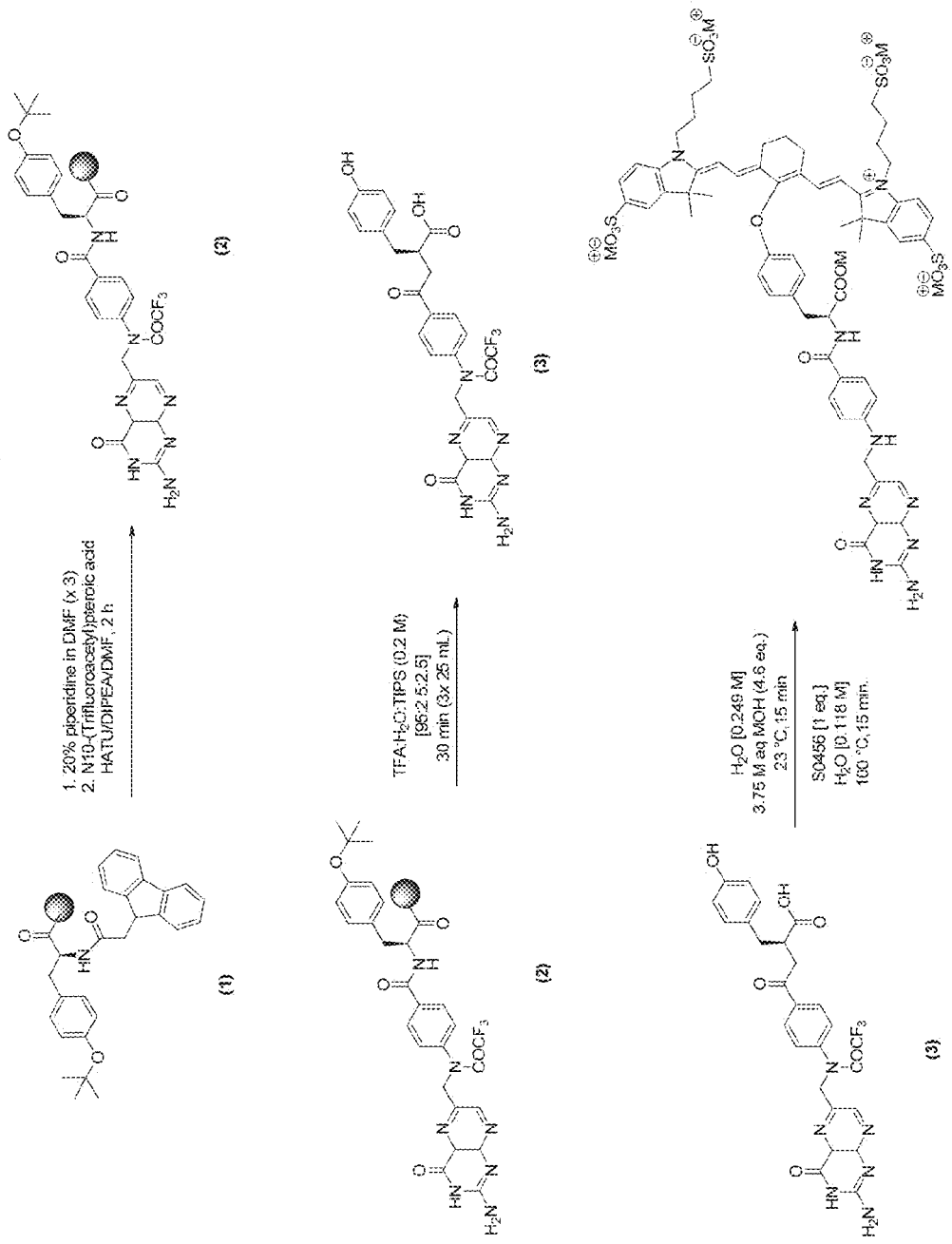
Figure 9 depicts a two step reaction schematic for solid phase synthesis of imaging compounds.

Figure 10 displays a preparative chromatogram profile of coupling reaction for OTL-0038.

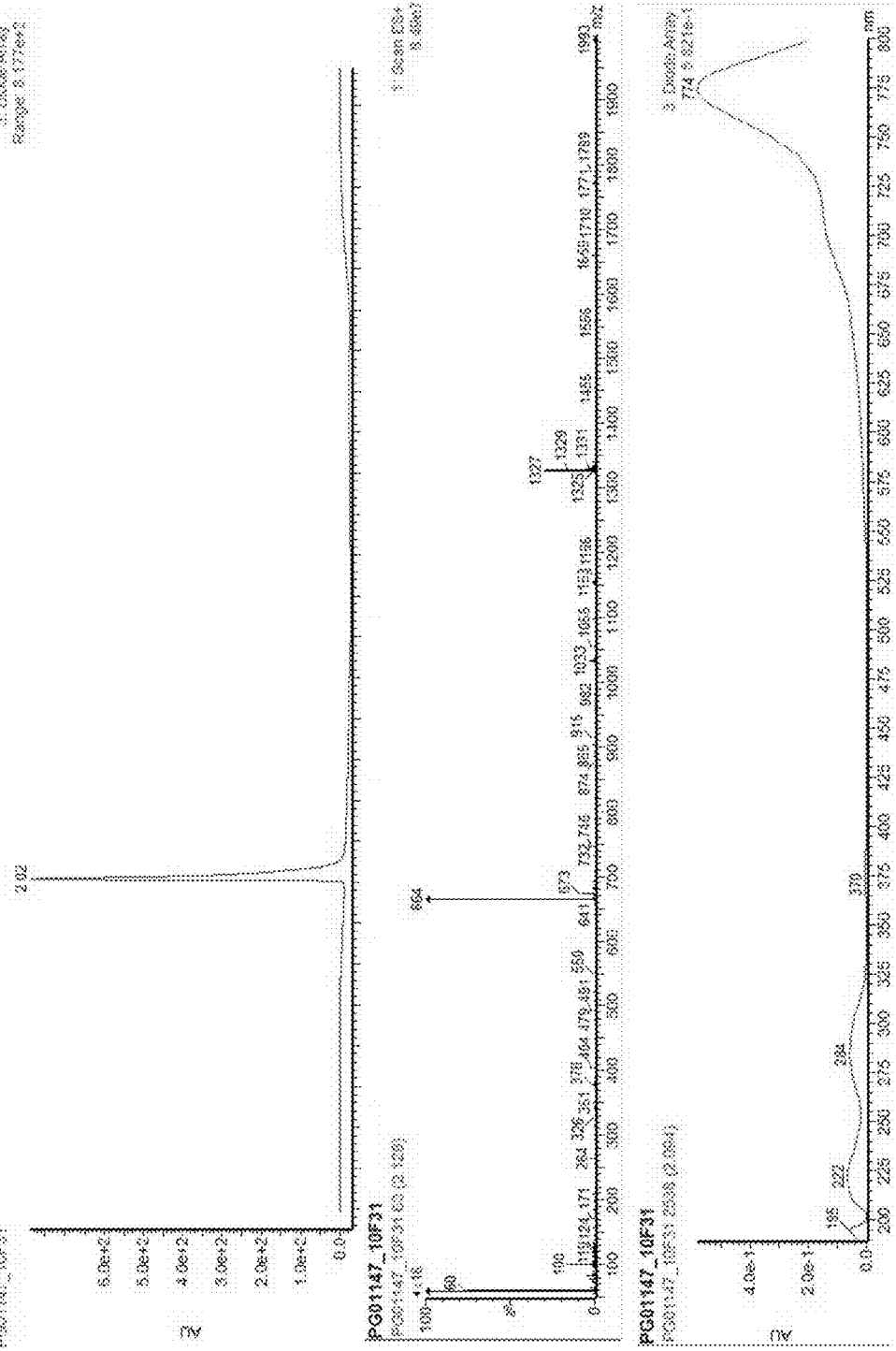
Figure 11 displays a chromatogram and a mass spectrum from an LC/MS and a UV profile of purified OTL-0038.

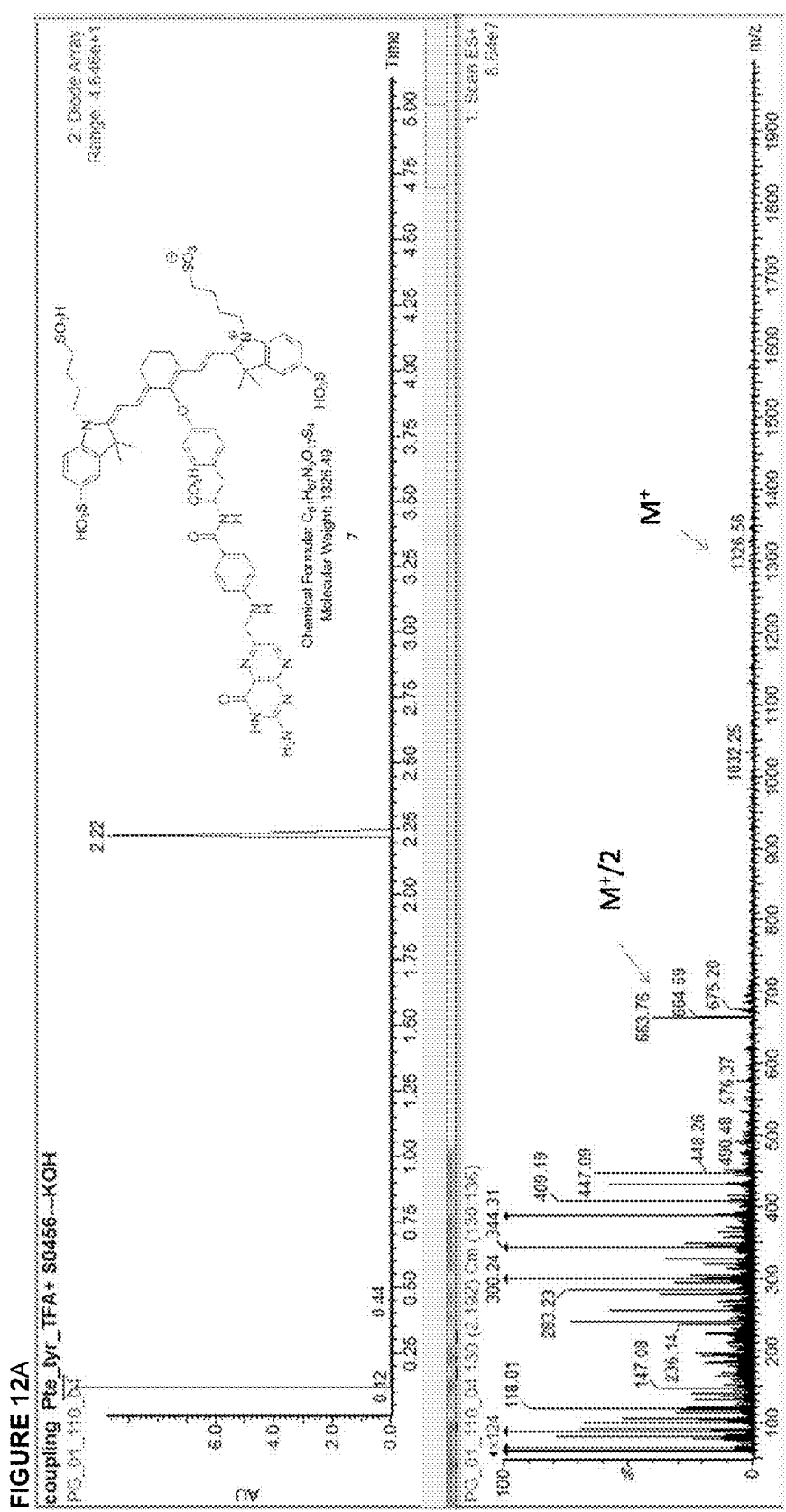
Figure 12A illustrates monitoring of reaction progress of Pte-Tyr-S0456 (OTL-0038) by LC/MS.

Figure 12B illustrates monitoring of reaction progress of folate-EDA-IR800CW by LC/MS.

METHODS OF MANUFACTURE OF PTEROYL-AMINO ACID-FLUORESCENT DYES

RELATED APPLICATIONS

The present patent application is related to and claims the priority benefit of U.S. Provisional Patent Application Ser. No. 61/791,921, filed Mar. 15, 2013 and PCT international patent application Ser. No. PCT/US13/56629, filed Aug. 26, 2013, the content of each is hereby incorporated by reference in its entirety into this disclosure.

TECHNICAL FIELD

The present disclosure is in the area of diagnostics. This disclosure provides methods of synthesizing and utilizing amino acid linking groups that are conjugated to a compound used for the targeted imaging of tumors. Conjugation of the amino acid linking groups increase specificity and detection of the compound. Methods of manufacture and synthesis of the compounds for use thereof in diagnostic imaging are contemplated.

BACKGROUND

Surgical removal of malignant disease constitutes one of the most common and effective therapeutic for primary treatment for cancer. Surgery is one of the best therapies for all the solid tumors, such prostate, ovarian, lung, breast, colon, and pancreatic cancer. While surgery cures 50% of patients with solid tumors in the US, chemo- and radiotherapy cure less than 5% of all cancer patients.

Over 700,000 patients undergo cancer surgery every year in the US and 40% of surgical patients have a recurrence of locoregional disease within 5 years. Despite of major advances in the oncology field over the last decade, hurdles to overcome in the field are complete resection of the primary tumor with negative margins, removal of the lymph nodes harboring metastatic cancer cells and identification of satellite disease. Achieving these three goals not only improves disease clearance but also guides decisions regarding postoperative chemotherapy and radiation.

While non-targeted fluorescent dyes have been shown to passively accumulate in some tumors, the resulting tumor-to-background ratios are often poor and the boundaries between malignant and healthy tissues can be difficult to define. Although ligand targeted fluorescence dyes (e.g., EC17: Folate-EDA-FITC) have been used for imaging a tissue, those dyes have been ineffective as they would not penetrate deep tissue and hence only identified the specific cells on the surface of a tissue rather than deeper within the tissue sample. In addition, it has been shown that the excitation and emission spectra of these previous fluorescence dyes was such that it produced significant background noise such that the targeted tissue was not easily detected. In addition, as discussed in the background above, fluorescein-based dyes have the disadvantages that of low shelf-life stability. EC17 easily decomposes as a result of the instability of the thiourea bridge in that compound. In addition, as EC17 uses fluorescein which has the drawback of a relatively high level of nonspecific background noise from collagen in the tissues surrounding the imaging site. Moreover, the absorption of visible light by biological chromophores, in particular hemoglobin, further limits the usefulness of dyes that incorporate fluorescein. This means that conventional dyes cannot readily detect tumors that may be buried deeper than a few millimeters in the tissue. Furthermore, fluorescence from fluorescein is quenched at low pH (below pH 5).

In order for a dye material to be useful in detecting and guiding surgery or providing other tissue imaging, it would be beneficial to overcome these drawbacks.

Not surprisingly, surgical methods for achieving more quantitative cytoreduction are now receiving greater scrutiny.

Resection of all detectable malignant lesions results in no detectable return of the disease in approximately 50% of all cancer patients and may extend life expectancy or reduce morbidity for patients in whom recurrence of the cancer is seen. Given the importance of total resection of the malignant lesions, it is beneficial to ensure that the malignant lesions are accurately and completely identified. Identification of malignant tissue during surgery is currently accomplished by three methods. First, many tumor masses and nodules can be visually detected based on abnormal color, texture, and/or morphology. Thus, a tumor mass may exhibit variegated color, appear asymmetric with an irregular border, or protrude from the contours of the healthy organ. A malignant mass may also be recognized tactilely due to differences in plasticity, elasticity or solidity from adjacent healthy tissues. Finally, a few cancer foci can be located intraoperatively using fluorescent dyes that flow passively from the primary tumor into draining lymph nodes. In this latter methodology, fluorescent (sentinel) lymph nodes can be visually identified, resected and examined to determine whether cancer cells have metastasized to these lymph nodes.

Despite the recognition of the importance of removal of tumor and the availability of certain identification techniques for visualizing tumor mass, many malignant nodules still escape detection, leading to disease recurrence and often death. Thus, there is a need for improved tumor identification. This motivation has led to introduction of two new approaches for intraoperative visualization of malignant disease. In the first, a quenched fluorescent dye is injected systemically into the tumor-bearing animal, and release of the quenching moiety by a tumor-specific enzyme, pH change, or change in redox potential is exploited to selectively activate fluorescence within the malignant mass. In the second approach, a fluorescent dye is conjugated to a tumor-specific targeting ligand that causes the attached dye to accumulate in cancers that overexpress the ligand's receptor. Examples of tumor targeting ligands used for this latter purpose include folic acid, which exhibits specificity for folate receptor (FR) positive cancers of the ovary, kidney, lung, endometrium, breast, and colon, and DUPA, which can deliver attached fluorescent dyes selectively to cells expressing prostate-specific membrane antigen (PSMA), i.e. prostate cancers and the neovasculature of other solid tumors. Beneficially, one folate-targeted fluorescent dye (folate-fluorescein or EC17) has been recently tested intra-operatively in human ovarian cancer patients. In this study, ~5× more malignant lesions were removed with the aid of the tumor-targeted fluorescent dye than without it, and all resected fluorescent lesions were confirmed by pathology to be malignant.

Conventional fluorescent techniques use probes in the visible light spectrum (.about.400-600 nm), which is not optimal for intra-operative image-guided surgery as it is associated with a relatively high level of nonspecific background light due to collagen in the tissues. Hence the signal to noise ratio from these conventional compounds is low. Moreover, the absorption of visible light by biological chromophores, in particular hemoglobin, limits the penetration depth to a few millimeters. Thus tumors that are buried deeper than a few millimeters in the tissue may remain undetected. Moreover ionization equilibrium of fluorescein (pKa=6.4) leads to pH-dependent absorption and emission over the range of 5 to 9. Therefore, the fluorescence of fluorescein-based dyes is quenched at low pH (below pH 5).

For example, the potential use of EC17 dye for a more widespread use in optical imaging for the characterization and measurement diseased tissue in a clinical setting has been hampered by the major drawback of that the attached dye (fluorescein) emits fluorescence in the visible range. This makes EC17 and related dyes poor for in vivo use in tissues because tissues typically autofluoresce strongly in the visible range, and light penetrates tissue poorly. Moreover, EC17 (folate-ethelenediamine-fluorescein isothiocyanate) includes a thiourea linker. It is well known that thiourea compounds have low shelf life due to the instability of the thiourea linkage. Thus, a compound such as EC17 is not optimal for use in optical imaging because of this instability and the related decomposition of thiourea bridge.

The combination of light absorption by hemoglobin in the visible light spectrum (<600 nm) and water and lipids in the IR range (>900 nm), offers an optical imaging window from approximately 650-900 nm in which the absorption coefficient of tissue is at a minimum. A suitable alternative to dyes that emit light in the visible range would be to develop dyes that can be used in the near infra red (NIR) range because light in the near infrared region induces very little autofluorescence and permeates tissue much more efficiently. Another benefit to near-IR fluorescent technology is that the background from the scattered light from the excitation source is greatly reduced since the scattering intensity is proportional to the inverse fourth power of the wavelength. Low background fluorescence is necessary for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components.

While the use of light in the NIR range for deeper tissue imaging is preferable to light in the visible spectrum, the NIR imaging dyes currently used in the art suffer from a number of challenges and disadvantages such as a susceptibility to photobleach, poor chemical stability, absorbance and emission spectra that fall within the same range as many physiological molecules (resulting in high background signal and autofluorescence). Moreover, most of the NIR dyes are not stable during the synthesis, especially conjugating to a ligand with an amine linker, leading to multiple unwanted side products. Therefore, taking ligand-targeted NIR imaging agent for clinic can be expensive. Thus, current imaging methods that utilize NIR fluorescent probes are not effective in deep tissue imaging (>5 mm from the surface), in quantifying fluorescence signal in mammalian tissues, or in production cost that increase preclinical-to-clinical translational time.

Two promising approaches to fluorescence-guided surgery are currently under intense investigation for use in the clinic. In one method, an activatable NIR fluorescent probe, which is minimally fluorescent in the steady state due to its proximity to an attached quencher, becomes highly fluorescent upon release of the quencher in malignant tissue. One of the most commonly used release mechanisms involves incorporation of a peptide sequence between the dye and the quencher that can be specifically cleaved by a tumor-enriched protease (i.e. cathepsins, caspases and matrix metalloproteinases). A major advantage of this strategy lies in the absence of fluorescence in tissues that lack the activating enzyme, allowing tissues along the excretion pathway (e.g. kidneys, bladder, liver) to remain nonfluorescent unless they fortuitously express the cleaving enzyme. Such tumor-activated NIR dyes can also generate substantial fluorescence in the tumor mass as long as the malignant lesion is enriched in the cleaving protease and the released dye is retained in the tumor. The major disadvantage of this methodology arises from the poor tumor specificities of many of the relevant hydrolases (most of which are also expressed in healthy tissues undergoing natural remodeling or experiencing inflammation). Moreover, the abundance of the desired proteases may vary among tumor masses, leading to slow or no activation of fluorescence in some malignant lesions and rapid development of fluorescence in others.

Thus, there remains a need for the synthesis and purification of a dye substance that can be used to specifically target diseased tissue and has increased stability and brightness for use in vivo for tissue imaging.

BRIEF SUMMARY OF THE DISCLOSURE

This disclosure provides a method for synthesizing amino acid linking groups that are conjugated to a compound used for the targeted imaging of tumors and lymph nodes.

In one embodiment of the invention, this disclosure relates to a method of synthesizing a compound having the formula

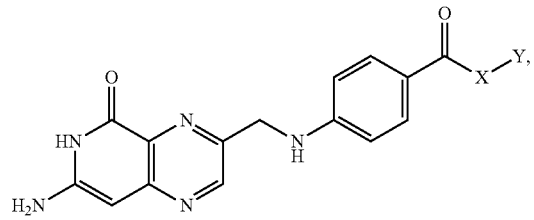

or a pharmaceutically acceptable salt or isotope thereof, wherein X is an amino acid or a derivative thereof, and Y is a dye that has a fluorescence excitation and emission spectra in the near infra red (NIR) range, and the compound maintains or enhances the fluorescence of the dye, comprising the steps of a) mixing an a pterin derivative compound and amino acids in the presence of (-(7-azabenzotriazol-1-yl)-N,N,N',N'-tetramethyluronium hexafluorophosphate (HATU), Hunig's base (DIPEA) and a polar solvent; b1) adding strong acid to form a precipitate; b2) dissolving the resulting precipitate in TFA:TIPS:$H_2O$ (95:2.5:2.5) solvent to form a suspension; c) transferring via cannula the suspension as a steady stream to methyl tertiary-butyl ether (MTBE) or diethyl ether to precipitate an intermediate compound; d) filtering and washing the intermediate compound precipitate with Methyl tertiary-butyl ether (MTBE); e) drying the intermediate compound solution under high vacuum conditions; f) suspending the resulting intermediate compound with water; g) adding aqueous sodium hydroxide (NaOH) to adjust the pH; h) mixing the aqueous solution with a fluorescent dye Y and water to obtain a resulting mixture in an oil bath or at ambient temperature; i) cooling the resulting mixture to room temperature; j1) adding the resulting mixture to stirred acetone to give a precipitate pteroyl-amino acid-fluorescent dye compound; j2) filtering the precipitate pteroyl-amino-acid-fluorescent dye under aspirator vacuum on sintered funnel washed with acetone, and k) drying the precipitate pteroyl-amino-acid-fluorescent dye compound under high vacuum conditions. The amino acid of the compound may be selected from the group consisting of tyrosine, cysteine, lysine, a derivative of tyrosine, a derivative of cysteine and a derivative of lysine. In a particular embodiment, the amino acid compound is tyrosine, and in a more particular embodiment, the amino acid compound is a derivative of tyrosine selected from the group consisting of:

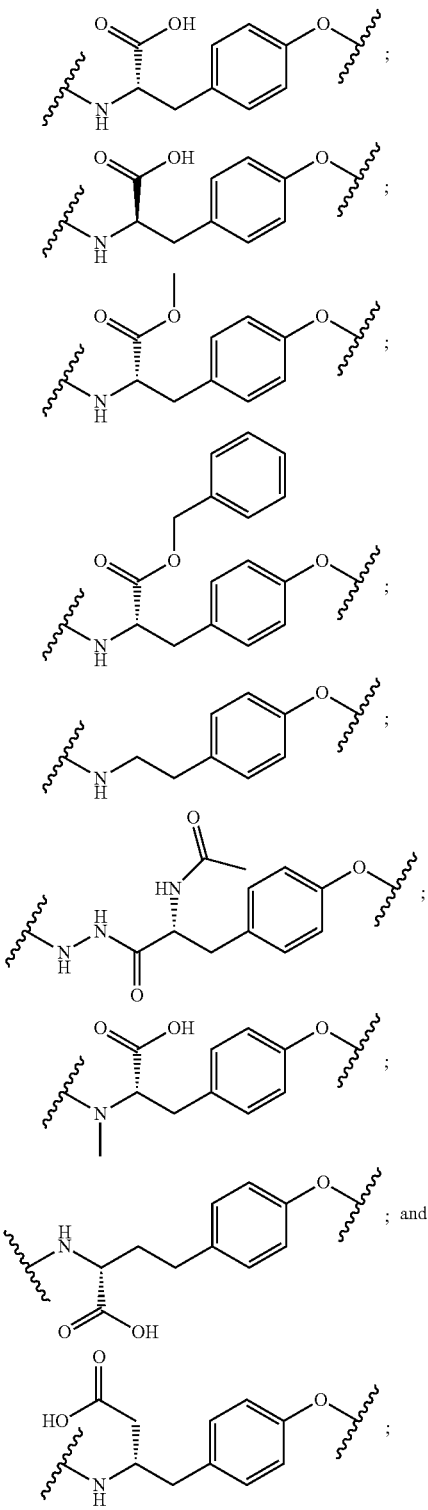

and racemic mixtures thereof.

Additionally, the dye Y of the compound may have the formula:

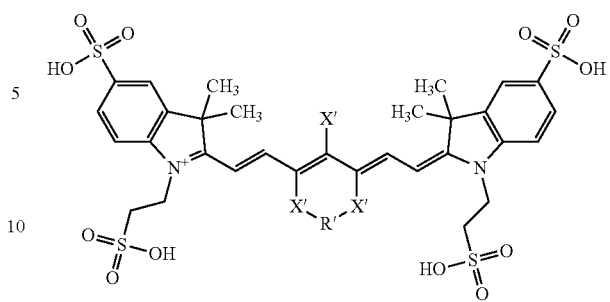

wherein X' is independently selected from the group consisting of O, S, N and C, and R' is independently selected from the group consisting of $CH_2$ and $CH_2CH_2$. In particular embodiments, the dye Y is selected from the group consisting of

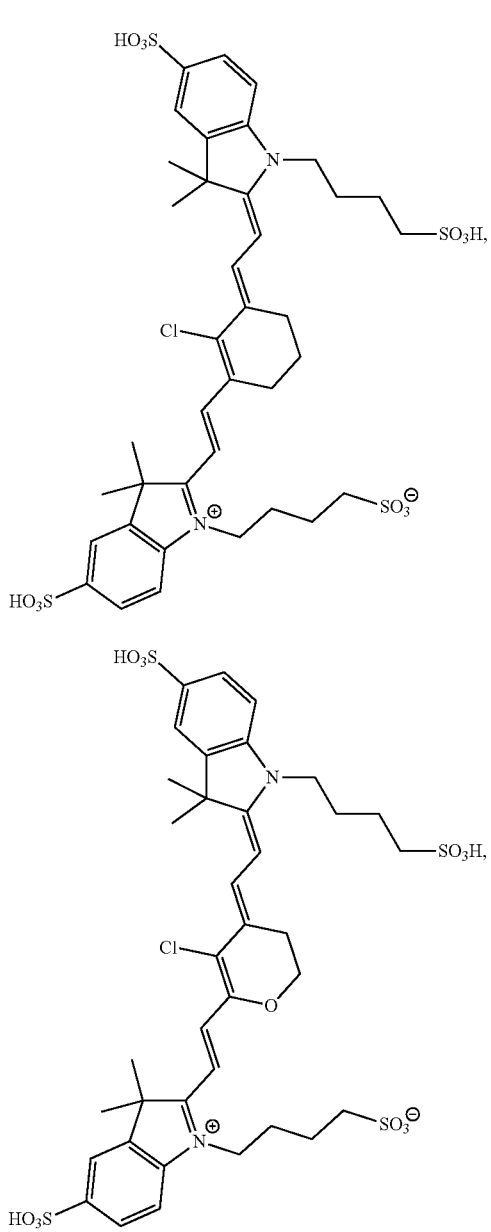

S0121

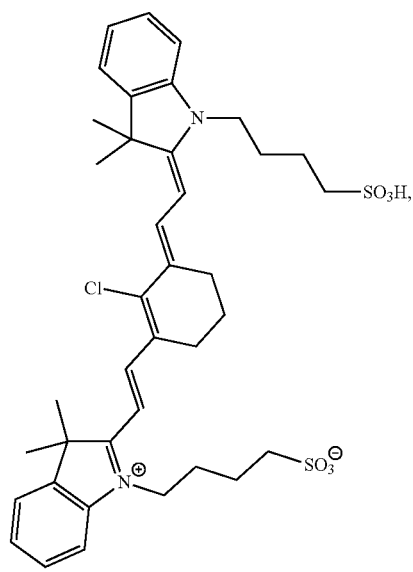

KODAK IRD28

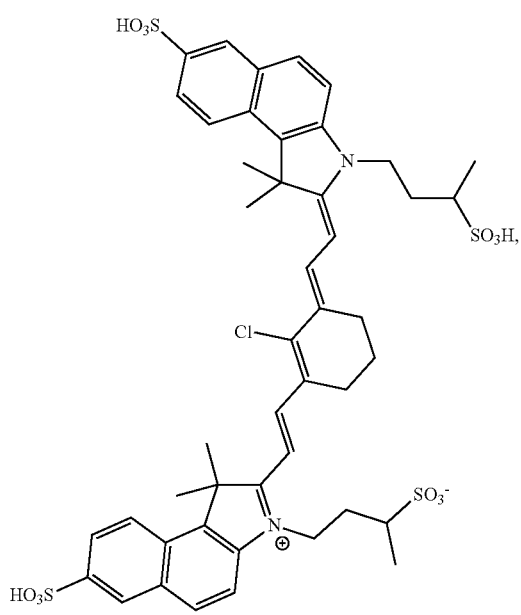

S2076

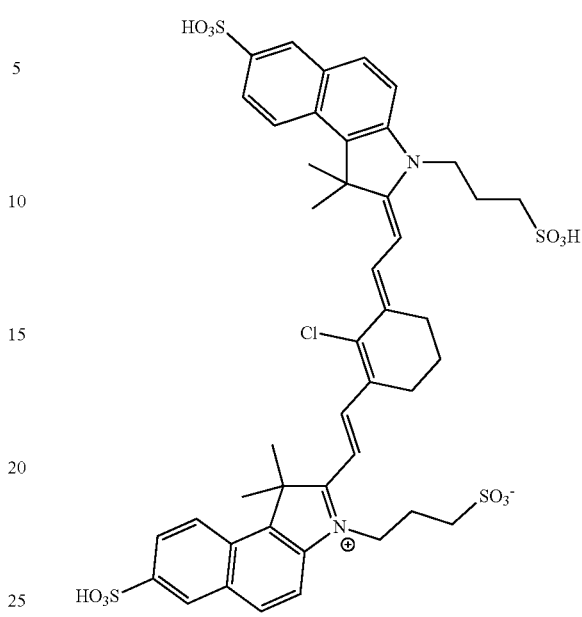

LS288, IR800, and derivatives thereof.

Further to this embodiment, the pterin derivative may be selected from a group consisting of folate and pteroic acid. The polar solvent may be dimethylformamide (DMF) or anhydrous dimethylsulfoxide (DMSO).

The method of this embodiment may further comprise an additional step of purifying the compound, comprising the steps of l) dissolving the precipitate amino add-fluorescent dye compound in water to resuspend the compound; m) filtering a resulting suspension through cotton; n) adding the filtered suspension as a steady stream to isopropyl alcohol (IPA); o) decanting a supernatant; p) diluting the residual suspension with isopropyl alcohol (IPA); q) filtered the diluent under high vacuum conditions; r) washing the solid with isopropyl alcohol (IPA) and acetone; and s) drying the purified amino acid-fluorescent dye compound. In an alternate embodiment, this method may further comprise a low-pressure purification of the compound, comprising the steps of l) dissolving the precipitate amino acid-fluorescent dye compound crude product into water buffered with a modifier at a pH range of about 5- to about 10; m) loading the buffered precipitate solution onto a column; n) eluting the column with a gradient comprising acetonitrile and a buffer including a range from about 0% to about 50% acetonitrile to equilibrate the column; o) removing the excess water buffer solution; and p) isolating a desired fraction of the compound. In another alternate embodiment, the modifier of step m) is selected from a group consisting of sodium acetate, ammonium acetate, sodium phosphate monobasic, and sodium phosphate dibasic. In yet another alternate embodiment, this method may further comprise a high-pressure purification of the compound, comprising the steps of l) dissolving the precipitate amino acid-fluorescent dye compound crude product in water; m) loading the precipitate solution onto a column; n) eluting the column with a gradient comprising a buffered water and acetonitrile; o) removing the excess water buffer solution; and p) isolating a desired fraction of the compound.

In a second embodiment of the invention, this disclosure provides a method of synthesizing a compound having the formula:

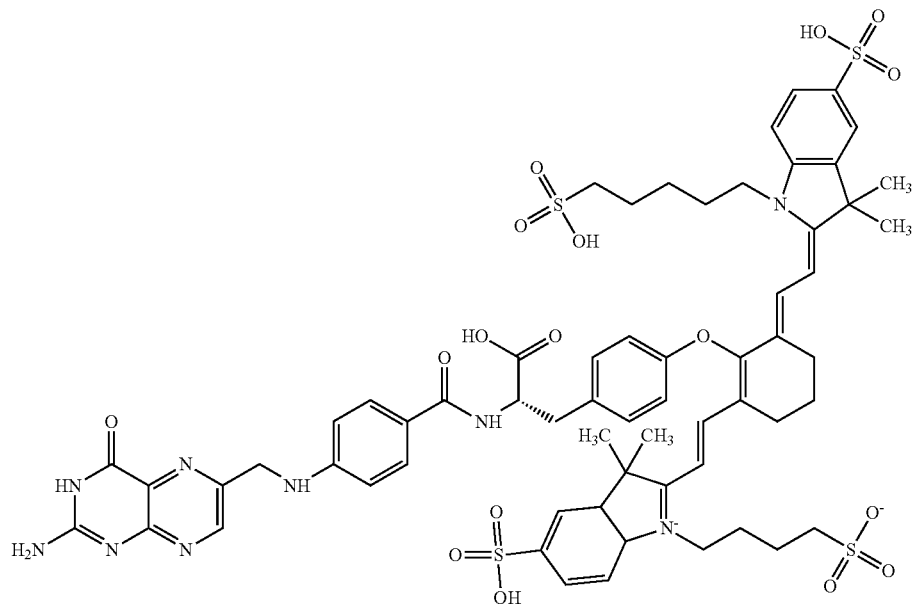

comprising the steps of: a) mixing pteroic acid and an amino acid in the presence of (-(7-azabenzotriazol-1-yl)-N,N,N',N'-tetramethyluronium hexafluorophosphate (HATU), Hunig's base (DIPEA) and a dimethylformamide (DMF); b1) adding strong acid to form a precipitate; b2) dissolving the resulting precipitate product to TFA:TIPS:$H_2O$ (95:2.5:2.5) solvent to form a suspension; c) transferring by cannula the suspension as a steady stream to Methyl tertiary-butyl ether (MTBE) to precipitate Pte_TFA_L_Tyr; d) filtering and washing Pte_T-FA_L_Tyr precipitate with Methyl tertiary-butyl ether (MTBE); e) drying the Pte_TFA_L_Tyr solution under high vacuum conditions; f) suspending the resulting Pte_TFA_L_Tyr with water; g) adding aqueous sodium hydroxide (NaOH) to adjust the pH; h) mixing the aqueous Pte_TFA_L_Tyr solution with S0456 fluorescent dye and water to obtain a resulting mixture in an oil bath; i) cooling the resulting mixture to room temperature; j) adding the resulting mixture to a stirred acetone to obtain a Pteroyl-Tyr-S0456 compound; j2) filtering the Pteroyl-Tyr-S0456 compound under aspirator vacuum on sintered funnel washed with acetone, and k) drying the Pteroyl-Tyr-S0456 compound with acetone under high vacuum conditions.

In this second embodiment of the invention, the amino acid of the compound is (L)-Tyr(-O$^t$Bu)-O$^t$Bu•HCl.

The steps in this embodiment may be carried out in chronological order. Additionally, steps f) and h) may be combined.

The method of this embodiment may further comprise an additional step of purifying the Pteroyl-Tyr-S0456 compound, comprising the steps of: l) dissolving the precipitate Pteroyl-Tyr-S0456 compound in water to resuspend the compound; m) filtering a resulting suspension through cotton; n) adding the filtered suspension as a steady stream to isopropyl alcohol (IPA); o) decanting a supernatant; p) diluting the residual suspension with isopropyl alcohol (IPA); q) filtered the diluent under high vacuum conditions; r) washing the solid with isopropyl alcohol (IPA) and acetone; and s) drying the purified Pteroyl-Tyr-S0456 compound. In an alternate embodiment, this method may further comprise a low-pressure purification of the compound, comprising the steps of l) dissolving the precipitate amino acid-fluorescent dye compound crude product into water buffered with a modifier at a pH range of about 5 to about 10; m) loading the buffered precipitate solution onto a column; n) eluting the column with a gradient comprising acetonitrile and a buffer of from about 0% to about 20% acetonitrile to equilibrate the column; o) removing the excess water buffer solution; and p) isolating a desired fraction of the compound. In another alternate embodiment, the modifier of step m) is selected from a group consisting of sodium acetate, ammonium acetate, sodium phosphate monobasic, and sodium phosphate dibasic. In yet another alternate embodiment, this method may further comprise a high-pressure purification of the compound, comprising the steps of l) dissolving the precipitate amino acid-fluorescent dye compound crude product in water; m) loading the precipitate solution onto a column; n) eluting the column with a gradient comprising a buffered water and acetonitrile; o) removing the excess water buffer solution; and p) isolating a desired fraction of the compound.

In a third embodiment of the invention, this disclosure provides a method for synthesizing a compound in a solid phase having the formula:

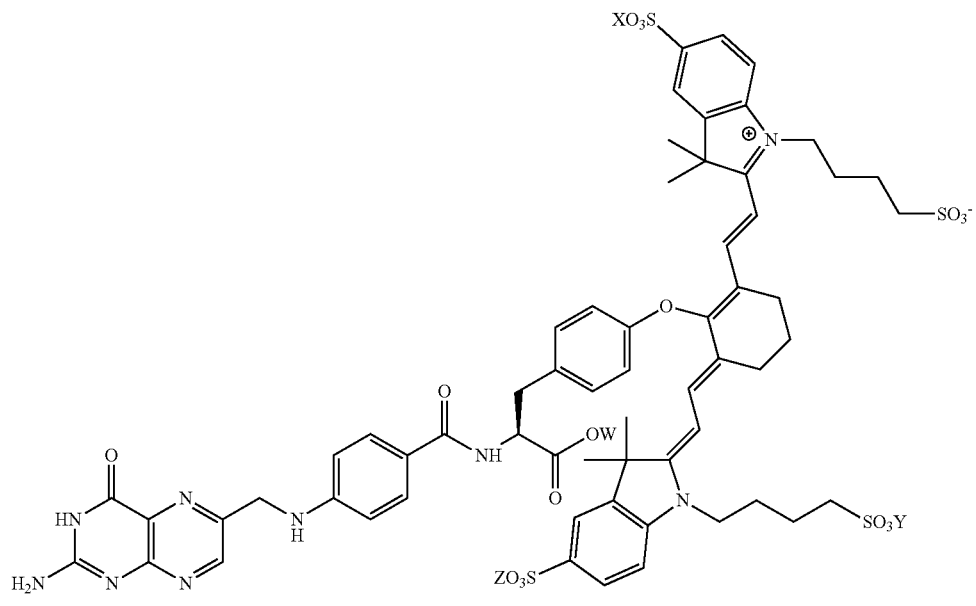

where W, X, Y, Z each are H, Na, K$^+$ or NH$_4^+$ comprising the steps of: a) swelling a Fmoc-Tyr($^t$Bu)-Wang Resin with piperidine, dichloromethane (DCM), and dimethylformamide (DMF) in a solid phase peptide synthesis vessel; b) adding a solution of N$^{10}$-(Trifluoroacetyl)pteroic acid in the presence of (-(7-azabenzotriazol-1-yl)-N,N,N',N'-tetramethyluronium hexafluorophosphate (HATU), Hunig's base (DIPEA) and dimethylformamide (DMF) to the resin; c) washing the resin with dimethylformamide (DMF) and isopropyl alcohol (IPA); d) swelling the resin with dichloromethane (DCM); e) drying the resin under argon; and f) cleaving a resulting TFA-Pteroyl_Tyr compound from the resin with TFA:H$_2$O:TIPS (95:2.5:2.5) under high vacuum conditions; g) mixing TFA-Pteroyl_Tyr precipitate with S0456 fluorescent dye and water to form a suspension; h) adding an aqueous sodium hydroxide (NaOH) to the suspension to adjust the pH of a resulting mixture; i) cooling the resulting mixture to room temperature; j) cannulating the resulting mixture to a stirred acetone to obtain a Pteroyl-Tyr-S0456 compound; and k) drying the a Pteroyl-Tyr-S0456 compound with acetone under high vacuum conditions.

The method of this embodiment may further comprise additional steps of purifying the Pteroyl-Tyr-S0456 compound, comprising the steps of: l) dissolving the precipitate Pteroyl-Tyr-S0456 compound in water to resuspend the compound; m) filtering a resulting suspension through cotton; n) adding the filtered suspension as a steady stream to isopropyl alcohol (IPA); o) decanting a supernatant; p) diluting the residual suspension with isopropyl alcohol (IPA); q) filtered the diluent under high vacuum conditions; r) washing the solid with isopropyl alcohol (IPA) and acetone; and s) drying the purified Pteroyl-Tyr-S0456 compound. In an alternate embodiment, this method may further comprise a low-pressure purification of the compound, comprising the steps of l) dissolving the precipitate amino acid-fluorescent dye compound crude product into water buffered with a modifier at a pH range of about 5 to about 10; m) loading the buffered precipitate solution onto a column; n) eluting the column with a gradient comprising acetonitrile and a buffer of from about 0% to about 20% acetonitrile to equilibrate the column; o) removing the excess water buffer solution; and p) isolating a desired fraction of the compound. In another alternate embodiment, the modifier of step m) is selected from a group consisting of sodium acetate, ammonium acetate, sodium phosphate monobasic, and sodium phosphate dibasic. In yet another alternate embodiment, this method may further comprise a high-pressure purification of the compound, comprising the steps of 1) dissolving the precipitate amino acid-fluorescent dye compound crude product in water; m) loading the precipitate solution onto a column; n) eluting the column with a gradient comprising a buffered water and acetonitrile; o) removing the excess water buffer solution; and p) isolating a desired fraction of the compound.

In another aspect of the invention, this disclosure provides a method of synthesizing a compound having the formula

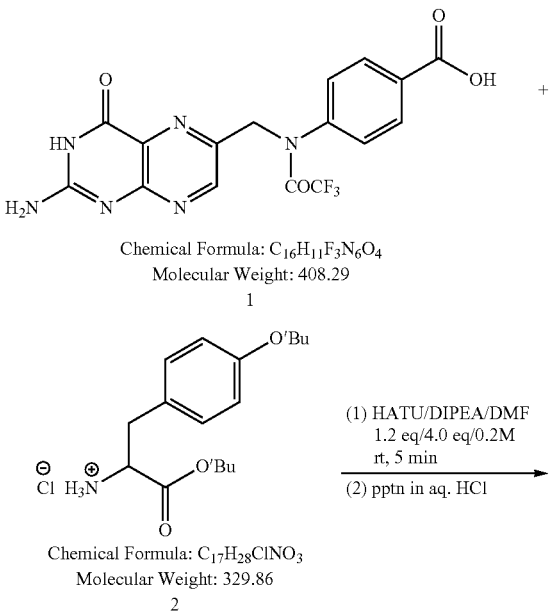

-continued
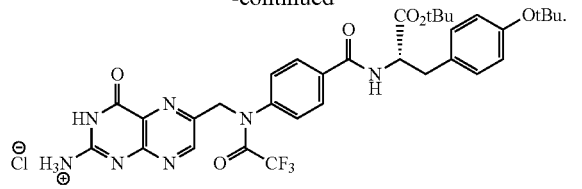
Chemical Formula: $C_{33}H_{37}ClF_3N_7O_6$
Molecular Weight: 720.14
3
In a fourth embodiment of the invention, this disclosure provides a method of synthesizing a compound having the formula

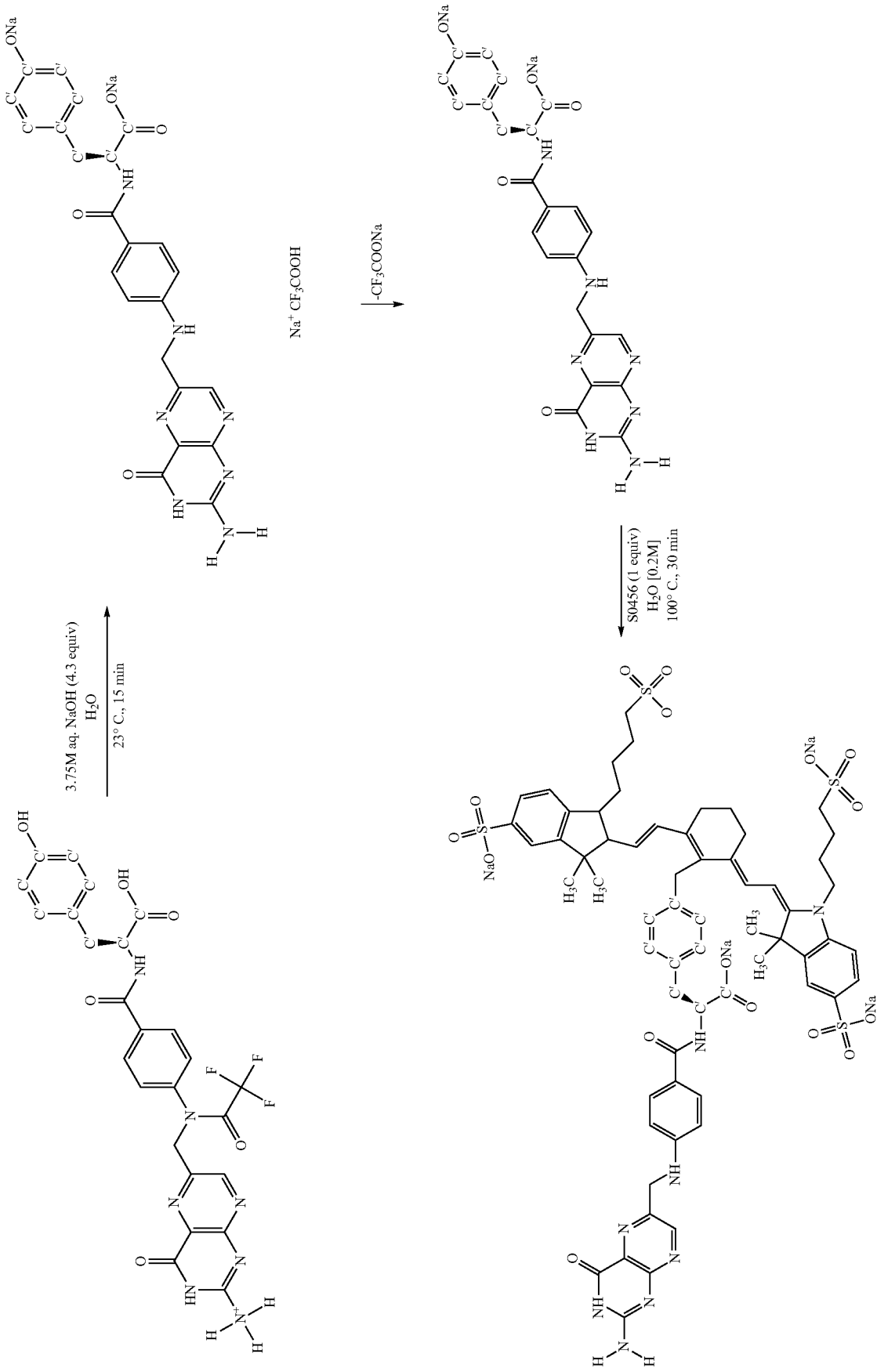

wherein C' is any carbon isotope.

In a fifth embodiment of the invention, this disclosure provides a method of synthesizing a compound having the formula

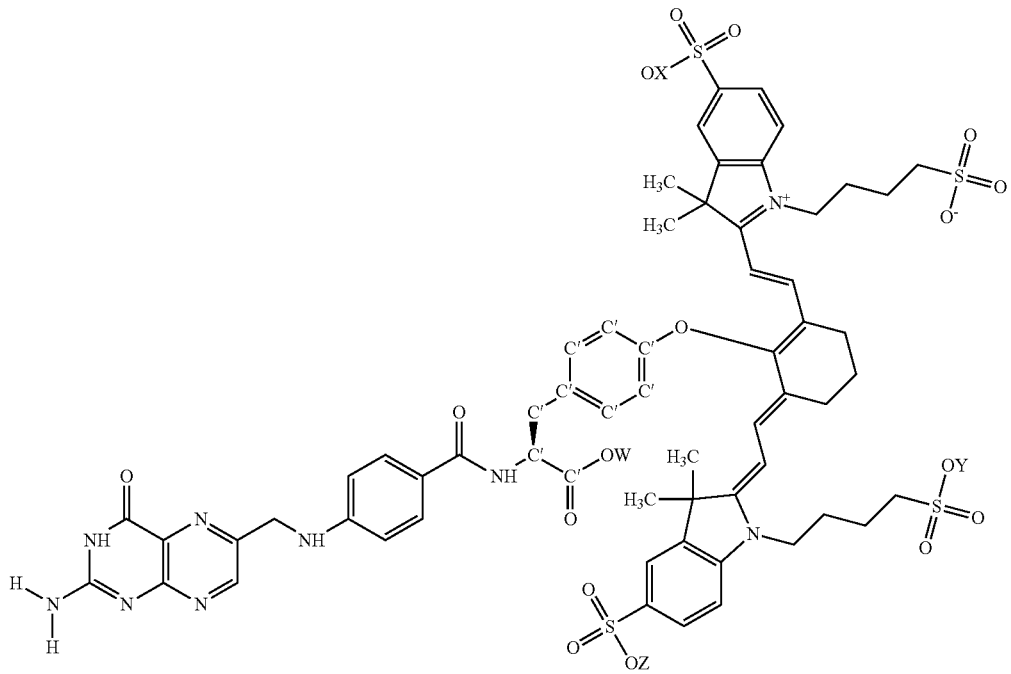

wherein C' is any carbon isotope. In this embodiment, the amino acid linker is selected from a group consisting of methyl 2-di-tert-butyl dicarbonate-amino-3-(4-phenyl) propanoate, 3-(4-hydroxyphenyl)-2-(di-tert-butyl-dicarbonate methylamino)propanoic acid, 2-amino-4-(4-hydroxyphenyl) butanoic acid, and Tert-butyl (2-di-tert-butyl dicarbonate-amino)-3-(4-hydroxyphenyl)propanoate. In a particular embodiment, the aqueous base is potassium hydroxide (KOH). The method of this embodiment may also further include purifying the compound by preparatory HPLC.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 2 depicts the relative binding affinity of OTL-0038, OTL-0039, and folic acid for folate receptors.

FIG. 2A is a plot which depicts the binding curve of each compound for folate receptors.

FIG. 2B is a table illustrating the binding affinity and relative binding affinity of all three compounds.

FIG. 3 shows whole body fluorescent images and ex vivo tissue biodistribution of mice injected 10 nmol of Pte-Tyr-S0456.

FIG. 4 shows head-to-head comparison of Pte-L-Try-S0456 (OTL-0038) with 2nd generation folate-NIR compounds.

FIG. 4B shows ex vivo tissue biodistribution illustrating head-to-head comparison of Pte-L-Try-S0456 (OTL-0038) with folate-ethylene diamine bridged-NIR conjugates. Dissected (sliced) tumors showed homogeneous uptake of the targeted imaging agents in the tumors.

FIG. 9 depicts a two step reaction schematic for solid phase synthesis of imaging compounds.

FIG. 11 displays a chromatogram and a mass spectrum from an LC/MS and a UV profile of purified OTL-0038.

FIG. 12 illustrates monitoring of reaction progress of (A) Pte-Tyr-S0456 (OTL-0038) and (B) folate-EDA-IR800CW by LC/MS.

FIG. 12A illustrates monitoring of reaction progress of Pte-Tyr-S0456 (OTL-0038) by LC/MS.

DETAILED DESCRIPTION OF THE DISCLOSURE

Figure 1:
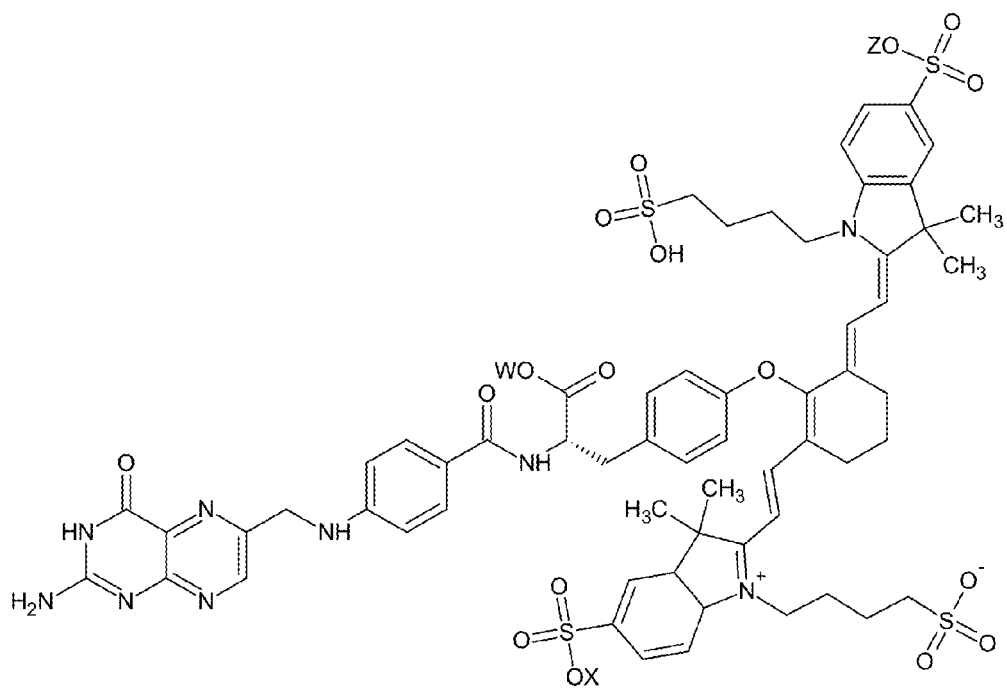
FIG. 1 Rational of Pte-L-Tyr-S0456 NIR dye (OTL-0038) compound. Chemical structure of Pteroyl-Tyr-S0456 with four beneficial functionalities: a=pterin derivative as a targeting molecule; b=tyrosine to improve binding affinity for folate receptor; c=phenolic moiety from tyrosine to enhance (brightness) fluorescence intensity; d=near-IR fluorescent probe. Therefore, tyrosine acts as part of ligand, linker, and near-IR dye. In other words, tyrosine is a linker that improves the binding affinity and specificity of ligand (pterin derivative). It also enhances the brightness of the NIR dye.
Figure 3A:
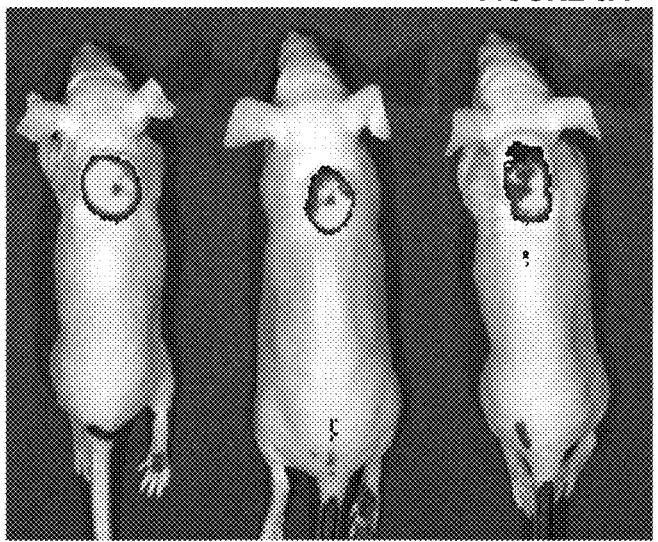
FIG. 3A illustrates fluorescent images of nude mice with KB tumor xenografts 2 hours following intravenous injection of 10 nmol folate receptor targeted-NIR compounds (overlay of Fluorescent and white light images).
Figure 3B:
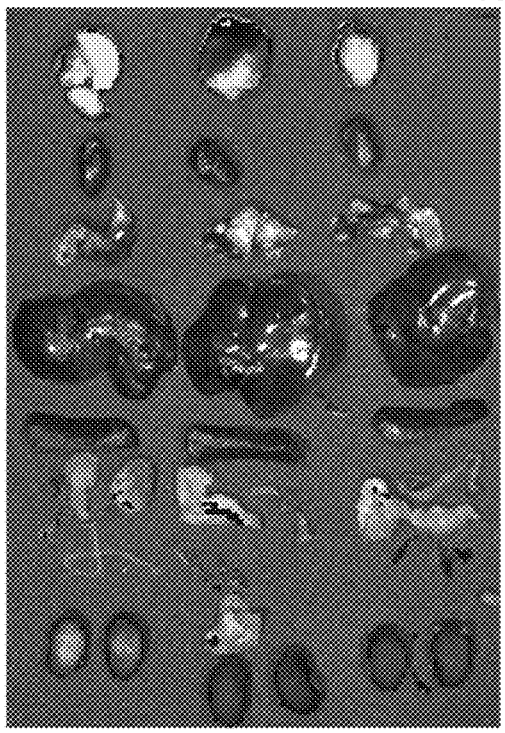
FIG. 3B illustrates ex vivo tissue biodistribution of compounds following harvesting tissues from previously imaged mice of FIG. 3A.
Figure 4A:
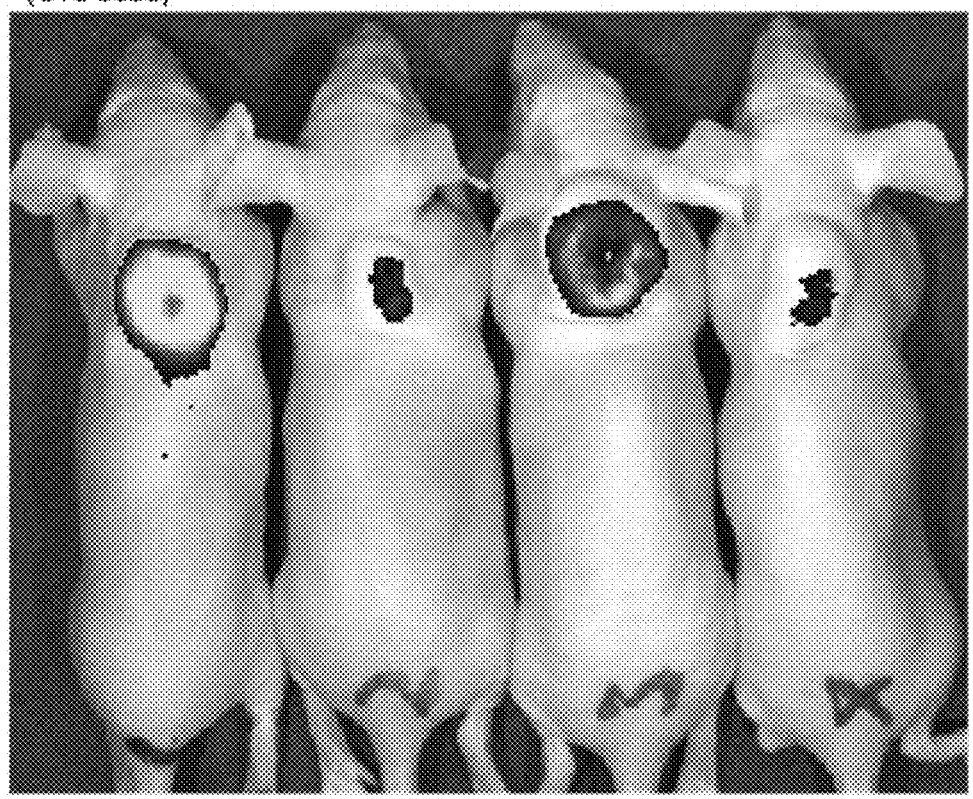
FIG. 4A illustrates whole body fluorescent images of head-to-head comparison of Pte-L-Try-S0456 (OTL-0038) with 2nd generation folate-NIR compounds.
Figure 4C:
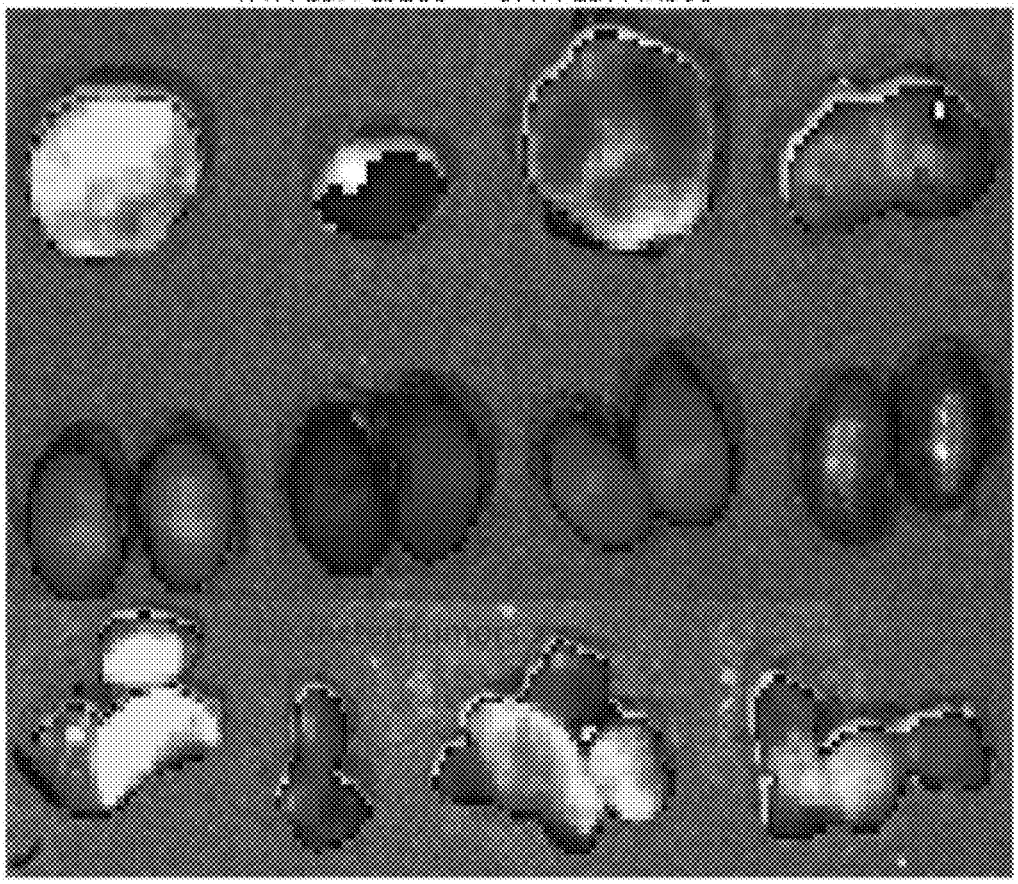
FIG. 4C shows Tumor and kidney images 2 h after administering conjugates (10 nmol) to nude mice illustrating head-to-head comparison of Pte-L-Try-S0456 (OTL-0038) with folate-ethylene diamine bridged-NIR conjugates. Dissected (sliced) tumors showed homogeneous uptake of the targeted imaging agents in the tumors.
Figure 4D:
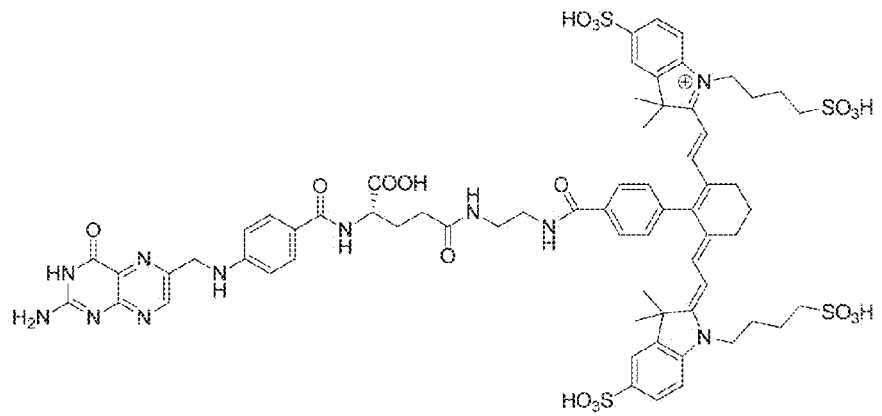
FIG. 4D illustrates Folate-EDA-LS288 (OTL-0001).
Figure 4E:
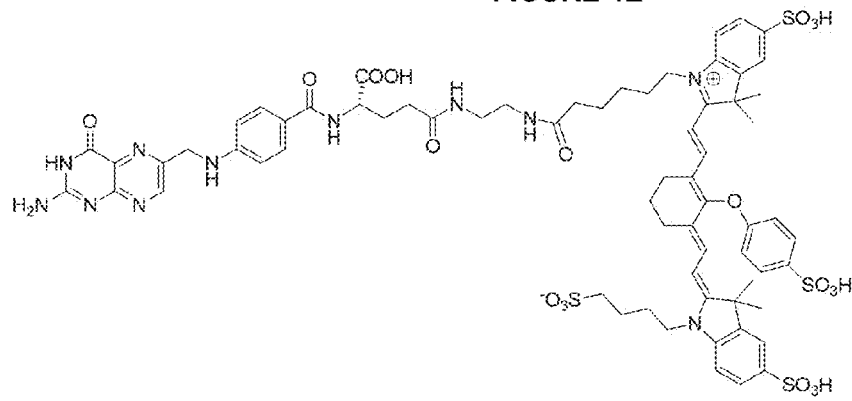
FIG. 4E illustrates Folate-EDA-IR800 (OTL-0002).
Figure 4F:
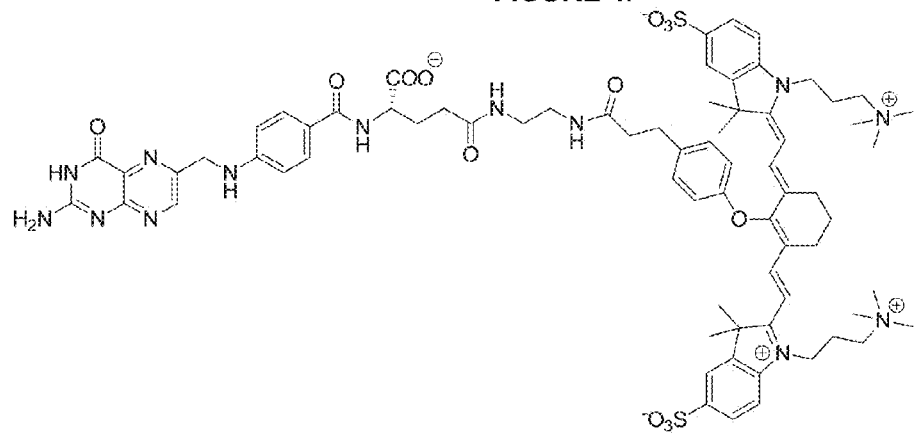
FIG. 4F illustrates Folate-EDA-ZW800 (OTL-0003).

Several criteria were considered in preparation of compounds including near infrared dyes. Ease of synthesis and chemical stability were primary chemical attributes. Spectral properties, such as absorption and emission spectra and quantum yield, were considered. Several biological properties were evaluated, such as binding affinity in cell studies, whole body animal imaging using mice with tumors, and biodistribution. Specifically for biodistribution several aspects were considered including dead mice after 2 hours per oral distribution, live mice imaging and dose escalation. Finally, safety considerations were taken including Maximum Tolerance Dose (MTD), ImmunoHistoChemical (IHC) analysis, and general clinical pathology analysis.

The present disclosure provides pteroyl compounds of near infrared dyes that are stable, fluoresce in the infrared range, and penetrate deep within targeted tissue to produce a specific and bright identification of areas of tissue that express folate receptor. More specifically, the pteroyl compounds are linked to the near infrared dyes through an amino acid linker. Even more specifically, it has been found that where the amino acid linker is tyrosine or a derivative of tyrosine, the intensity of the fluorescence of the dye is maintained or even enhanced.

In preferred embodiments, it is shown herein that such pteroyl compounds specifically target to tumor cells within a tissue. Moreover, the intensity of the fluorescence in greater than the intensity of previously observed with other near infrared dyes that are targeted with folate for folate receptor positive tumors. This increased intensity allows the targeting and clear identification of smaller areas of biological samples (e.g., smaller tumors) from a tissue being monitored. In addition, the increased intensity of the compounds of the present disclosure provides the added advantage that lower doses/quantities of the dye can be administered and still produces meaningful results. Thus, the compounds of the present disclosure lead to more economical imaging techniques. Moreover, there is an added advantaged that a lower dose of the compounds of the disclosure as compared to conventional imaging compounds minimizes the toxicity and other side effects that are attendant with administration of foreign materials to a body.

Furthermore, identification of small tumors will lead to a more accurate and more effective resection of the primary tumor to produce negative margins, as well as accurate identification and removal of the lymph nodes harboring metastatic cancer cells and identification of satellite disease. Each of these advantages positively correlates with a better clinical outcome for the patient being treated.

In specific experiments, it was found that use of amino acids other than tyrosine as the linker resulted in loss of near infrared fluorescence. For example, see discussion of Scheme I. Specifically note the synthetic pathway lead to undesired by-product 4 as major product that does not have NIR properties However, it is contemplated that in addition to tyrosine and tyrosine derivatives, a pteroyl compound of a near infrared dye with cysteine or cysteine derivatives also may be useful. Furthermore, it is contemplated that a direct linkage of the pteroyl or folate moiety to the dye or linkage of the dye to pteroic acid or folic acid through an amine linker also produces a loss of intensity of the fluorescence from the compound whereas the presence of the tyrosine or tyrosine derivative as the linking moiety between the pteroyl (targeting moiety) and the near infrared dye (the fluorescing moiety) is beneficial to maintain or enhance the fluorescence of the conjugated compound. Tyrosine-based compounds of the disclosure do not require an extra amine linker to compound the S0456 and further because conjugation through the phenol moiety of the tyrosine leads to enhanced fluorescence.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can be used for deep tissue three dimensional imaging, targeted surgery, and methods for quantifying the amount of a target cell type in a biological sample.

In an aspect the disclosure relates to compounds comprising the formula, Formula (I):

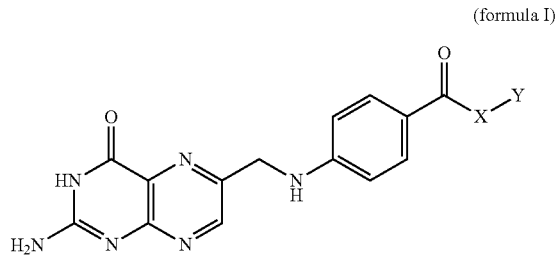

(formula I)

wherein:

X is an amino acid or a derivative thereof, and

Y is a dye that has a fluorescence excitation and emission spectra in the near infra red range, and said compound maintains or enhances the fluorescence of Y.

In some embodiments, the amino acid or amino acid derivative induces a shift in the electronic emission spectrum, the electronic absorption spectrum, or both the electronic emission and absorption spectrum, relative to the electronic spectra of the unmodified dye molecule. Suitably, the shift in the electronic spectrum is a bathochromic shift (i.e., shift to longer wavelength/lower frequency) that helps to improve the detection of the compound in the near infrared (NIR) spectral window and/or reduce the amount of background signal, autofluorescence, interferences from the tissue surrounding the area being visualized. More specifically, this shift in electronic spectrum is particularly observed with NIR dyes that comprise electronegative atoms that are incorporated into the 6-membered ring. Thus, in certain embodiments the amino acid or amino acid (X) derivative comprises an electron-rich moiety such as, for example, oxygen, sulfur, or nitrogen. Non-limiting examples of such amino acids can include cysteine, methionine, threonine, serine, tyrosine, phenylalanine, tryptophan, histidine, lysine, arginine, aspartic acid, glutamic acid, asparagine, and glutamine, or derivatives thereof.

In embodiments of this aspect, the disclosure provides compounds of Formulas I(a), I(b), I(c), and I(d):

wherein the Tyr, Cys, Ser, and Lys groups indicate a tyrosine, a cysteine, a serine, and a lysine amino acid residue, respectively, or derivatives thereof, and L is preferably a pteroyl or folate and Rx each comprises an independently selected solubilizing group that is optionally absent.

In embodiments of this aspect, the disclosure provides compounds of Formulas I(a1), I(b1), I(c1), and I(d1):

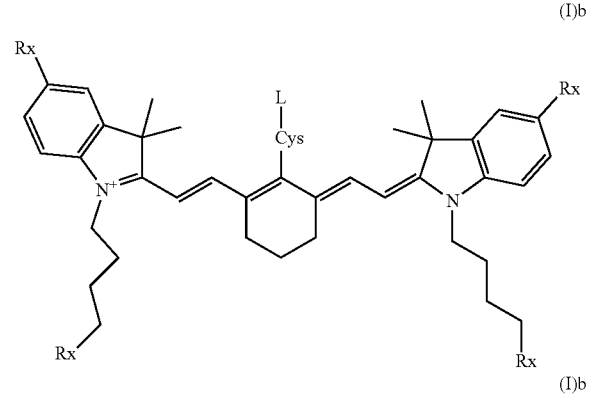

(I)b

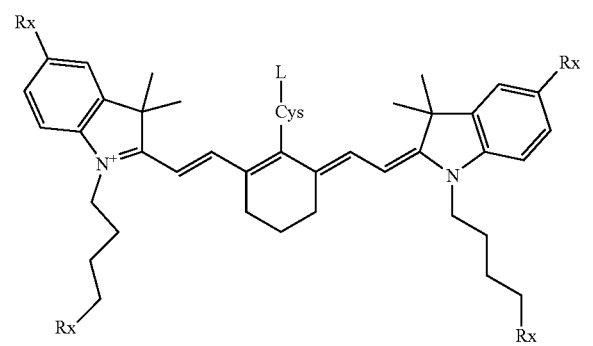

(I)b

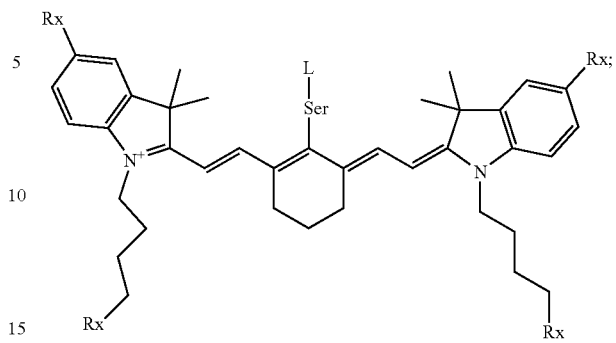

(I)c and

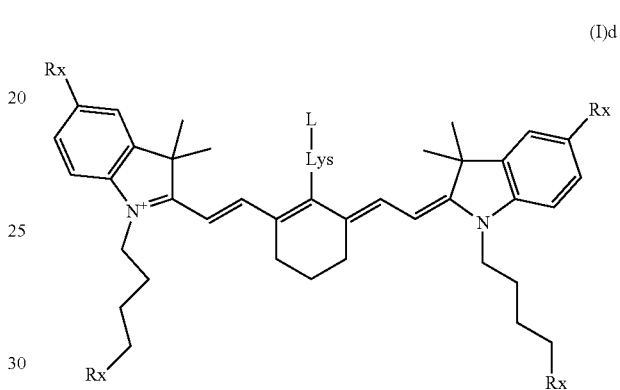

(I)d wherein the Tyr, Cys, Ser, and Lys groups indicate a tyrosine, a cysteine, a serine, and a lysine amino acid residue, respectively, or derivatives thereof, and L is preferably a pteroyl or folate. Preferably, L is pteroyl.

In specific preferred embodiments the disclosure provides a compound of Formula I(a), wherein Tyr is selected from the group consisting of:

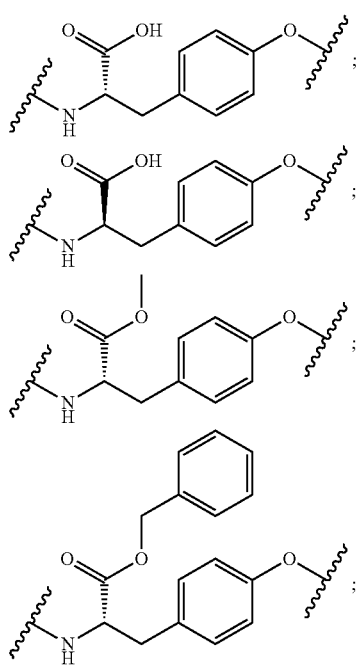

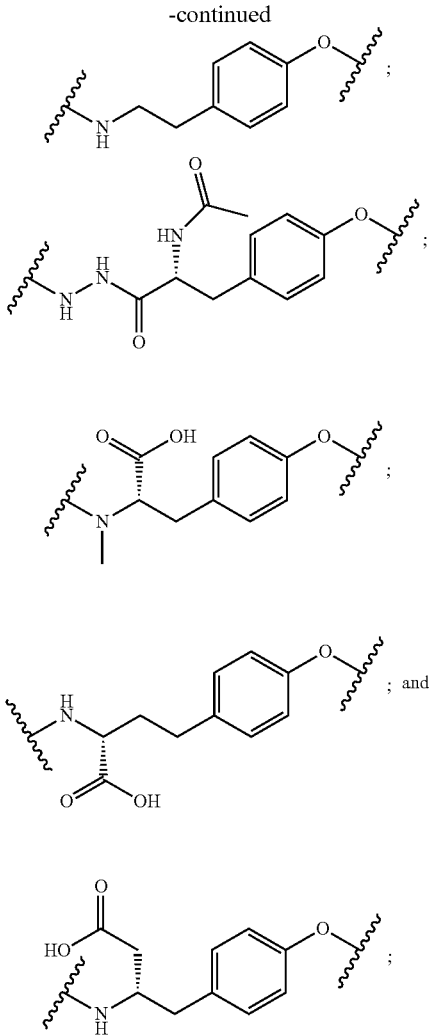

and derivatives thereof.

Suitably, the compounds disclosed herein have a maximum light absorption wavelengths in the near infrared region of between about 650 nm and 1000 nm, for example and preferably, at approximately 800 nm.

In specific preferred embodiments, the compounds disclosed herein include a ligand (L) that is effective to target the compound to a particular cell or tissue type and allow for imaging of that targeted cell or tissue. It is preferable the L is either pteroyl moiety or folate moiety and more preferable that L is pteroyl moiety. However, it is contemplated that the skilled person may use some other ligand L to target the compounds to a particular cell surface protein or receptor protein of interest. In specific and preferred embodiments, the ligand comprises pteroyl:

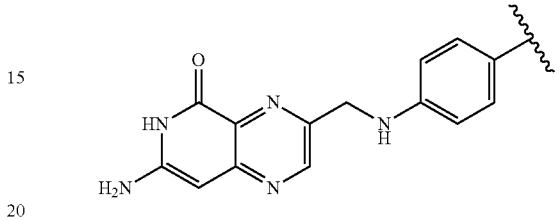

Synthesis of Compounds

The compounds disclosed herein can be made using conventional methods known in the literature. See for example, the dye compounds were synthesized as previously reported.

However, in specific preferred embodiments, the present disclosure provides more efficient synthetic methods for generating the compounds described herein (i.e., Compounds of Formula I). For example, the compounds having formulae I(a)-I(d) can be prepared in accordance to the general schemes outlined in each of Schemes I, II, and III below.

Scheme I, illustrates a synthetic scheme previously used to generate compounds of Formula I where the target ligand comprises a pterin derivative, such as folate or pteroic acid. The compounds of Formula I where the target ligand comprises folate linked through an amino acid (lysine) to the dye molecule are particularly illustrated by Scheme I. Briefly, the folate ligand modified by attachment to the amino group of the amino acid is reacted with a bridged ether derivative of the dye under conditions to yield products (3) and (4). However, it is notable that compound 3 is the preferred desirably compound but the synthetic pathway lead to presence of undesired by-product 4 as major product that does not have NIR properties. Moreover, its spectral properties are pH dependant. Thus, this scheme demonstrates the major drawback of ether bridged dyes. In the conventional production of these dyes, 30-60% of the yield is of the desired product and whereas 40-70% of the yield is of the undesired byproduct.

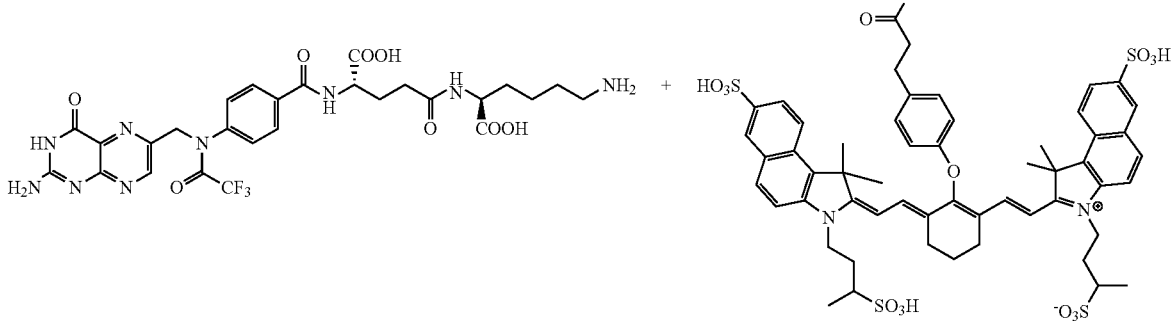

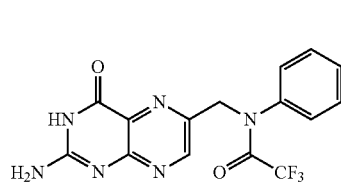
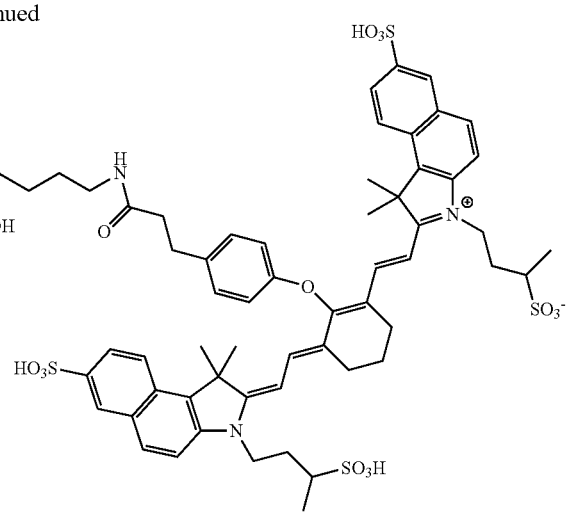

(3)

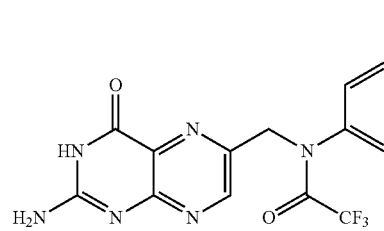
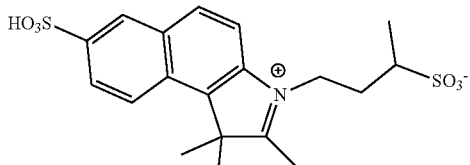
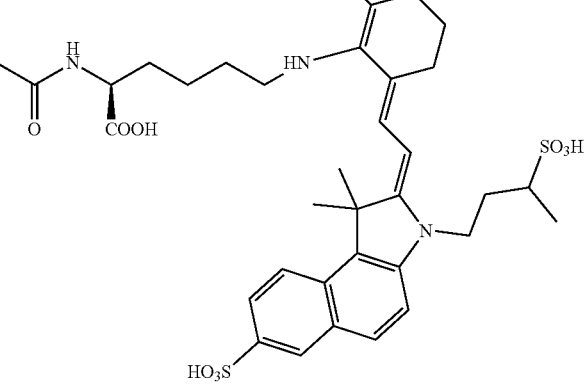

(4)

Scheme II provides a synthetic route that includes only three reaction steps and provides the product compound (5) in high yields (above 98%). Briefly, the targeting ligand (1) (illustrated in Scheme II with a pteroyl group) and an amino acid or amino acid derivative (2) that optionally includes protecting groups to avoid undesired reactivity with groups other than the amino group of the amino acid are mixed in a HATU[(O-(7-azabenzotriazol-1-yl)-N,N,N',N'-tetramethyluronium hexafluorophosphate)]/DIPEA (Diisopropylethylamine)/DMF (dimethylformamide) solvent system and reacted at a room temperature and for a sufficient time (5 minutes) to allow coupling of (2) through the amino functionality to ligand (1) to provide (3). Compound (3) can be advantageously precipitated by adding dilute acid to the reaction mixture, including other solvents such as dimethylsulfoxide (DMSO). More specifically, Compound 3 was precipitated in 1N HCl (hydrochloric acid) to get final compound over 98% purity, in these embodiments, the costly HPLC or column chromatography steps are avoided. Compound (3) is reacted to remove the protecting groups on the amino acid portion of the compound by reacting the compound at room temperature in TFA (trifluoroacetic acid):water:TIPS (triisopropylsilane) solvent system for provide compound (4). The compound 4 was purified by precipitation with diethyl ether or methyl-t-butyl ether to yield over 98% purity without HPLC (High performance liquid chromatography) or column chromatography. Compound (4) is reacted in a basic aqueous system (e.g., NaOH, sodium hydroxide) in order to remove the protecting group functionalities and is subsequently reacted, in slight molar excess, with the dye (S0456) in water for a time of 15 minutes and at a temperature of 80-100° C. that allows for coupling between the dye and (4), to yield final compound (5). Compound 5 was precipitated with acetone to give over 98% pure Pte-Tyr-S0456. When NaOH is used the sodium salt of Pte-Tyr-S0456 is produced.

Scheme 11:
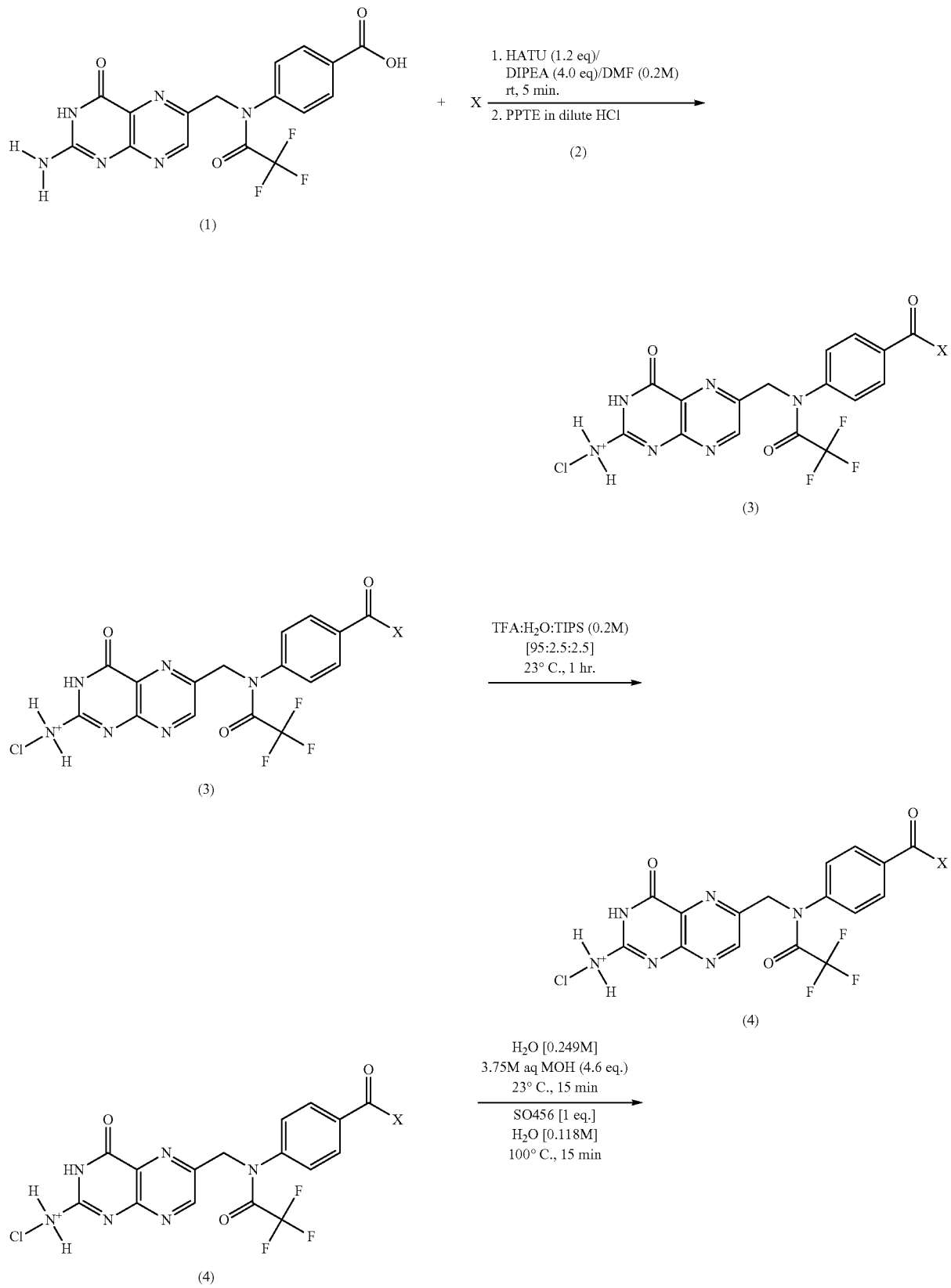

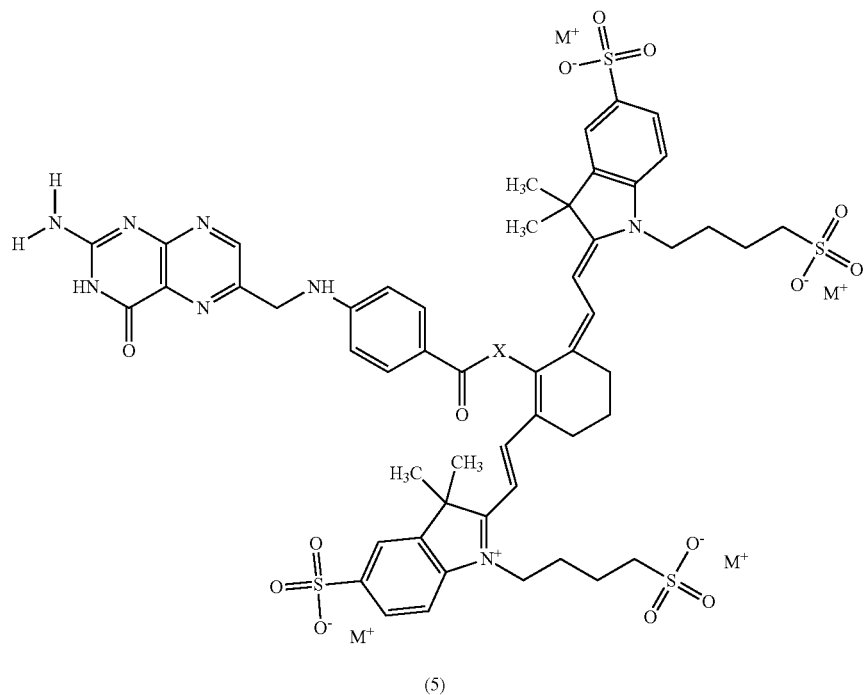

(5)

Scheme III provides an alternative solid phase synthetic route to produce the compounds disclosed herein and provide similar yields as described in Scheme II. Briefly, an amino acid bound to a substrate (1) (illustrated in Scheme III below as protected tyrosine attached to a resin bead) is reacted to remove the Fmoc (Fluorenylmethyloxycarbonyl) protecting group in 20% piperidine in DMF, and is subsequently reacted with the targeting ligand (again illustrated by pteroyl below) in HATU/DIPEA/DMF for a time and at a temperature sufficient to allow coupling of the ligand to the amine functional group of the amino acid to provide (2). Compound (2) is reacted to remove the substrate and any protecting groups on the amino acid in a series of reactions in a TFA:Water:TIPS solvent system to provide (3). Following a similar final step as described in Scheme II, compound (3) is reacted in a basic aqueous system in order to remove the protecting group functionalities and is subsequently reacted, in slight molar excess, with the dye (S0456) in water for a time and at a temperature that allows for coupling between the dye and (3), to yield final compound (4).

Scheme III:

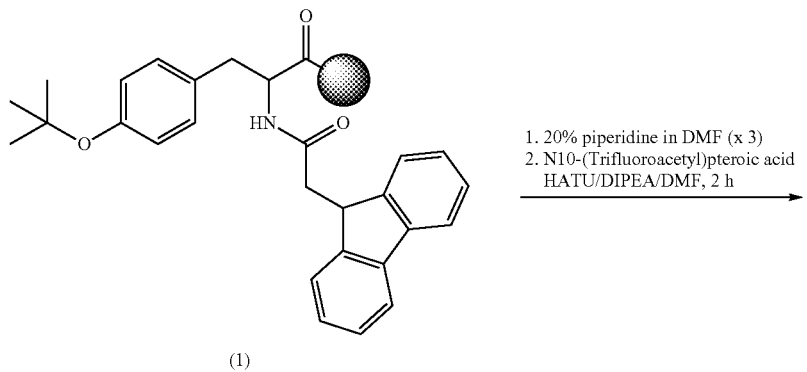

1. 20% piperidine in DMF (x 3)
2. N10-(Trifluoroacetyl)pteroic acid
   HATU/DIPEA/DMF, 2 h (1)

-continued
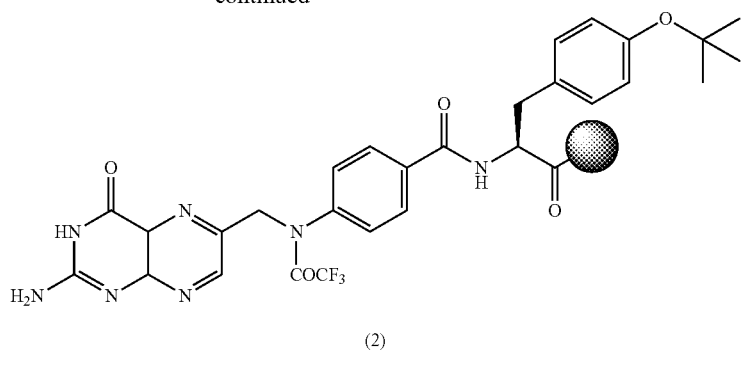
(2)
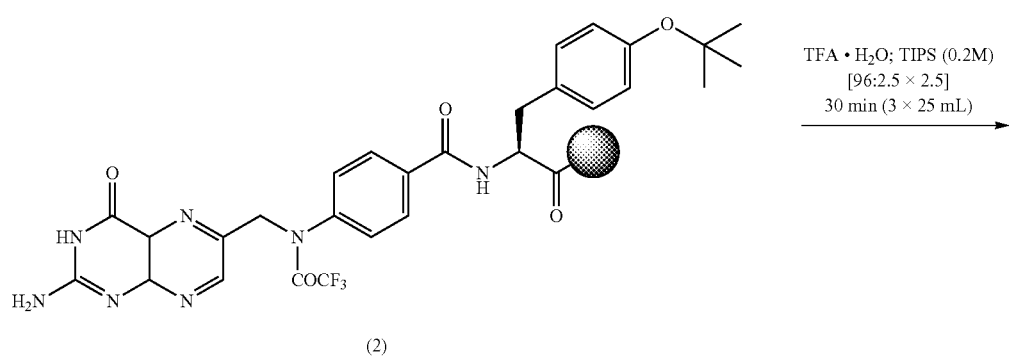
(2)
TFA • H₂O; TIPS (0.2M)
[96:2.5 × 2.5]
30 min (3 × 25 mL)
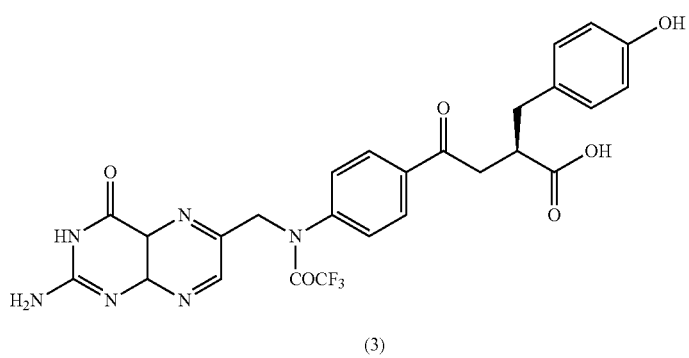
(3)
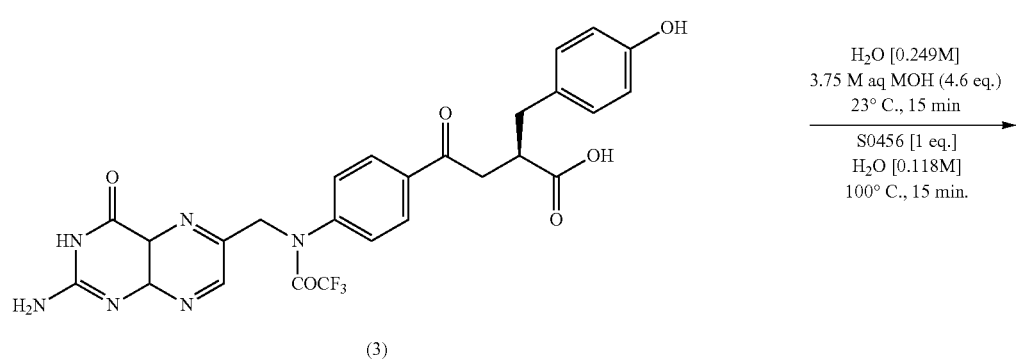
(3)
H₂O [0.249M]
3.75 M aq MOH (4.6 eq.)
23° C., 15 min
S0456 [1 eq.]
H₂O [0.118M]
100° C., 15 min.

-continued
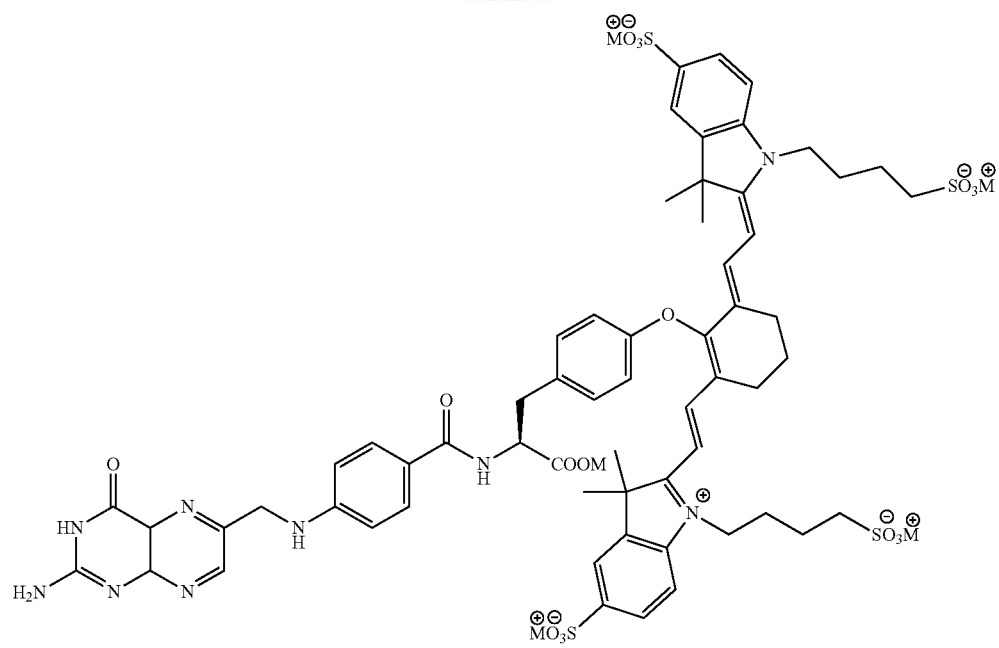
(4)
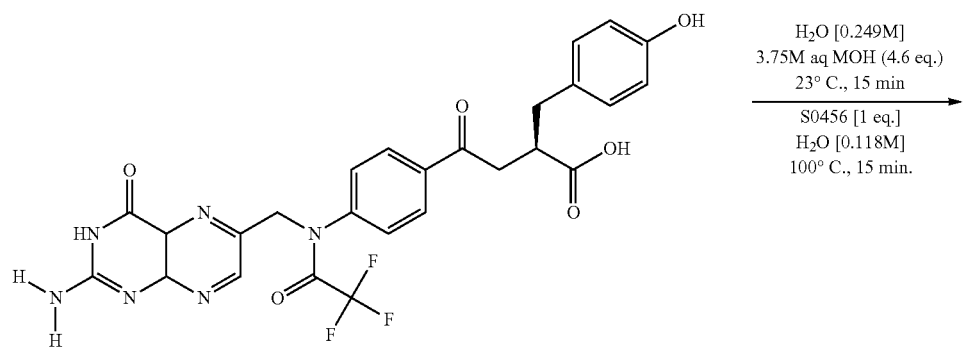

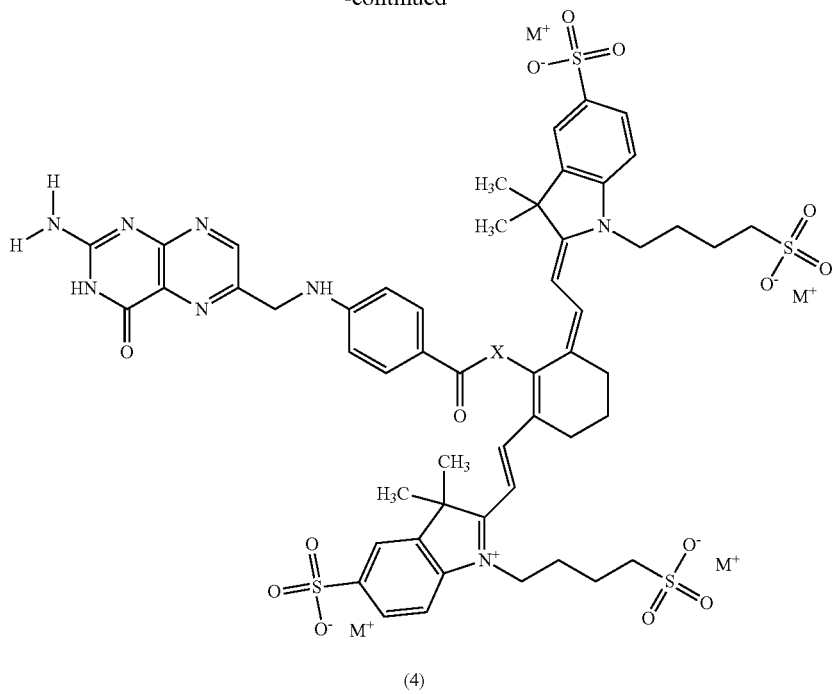

(4)

Figure 6:
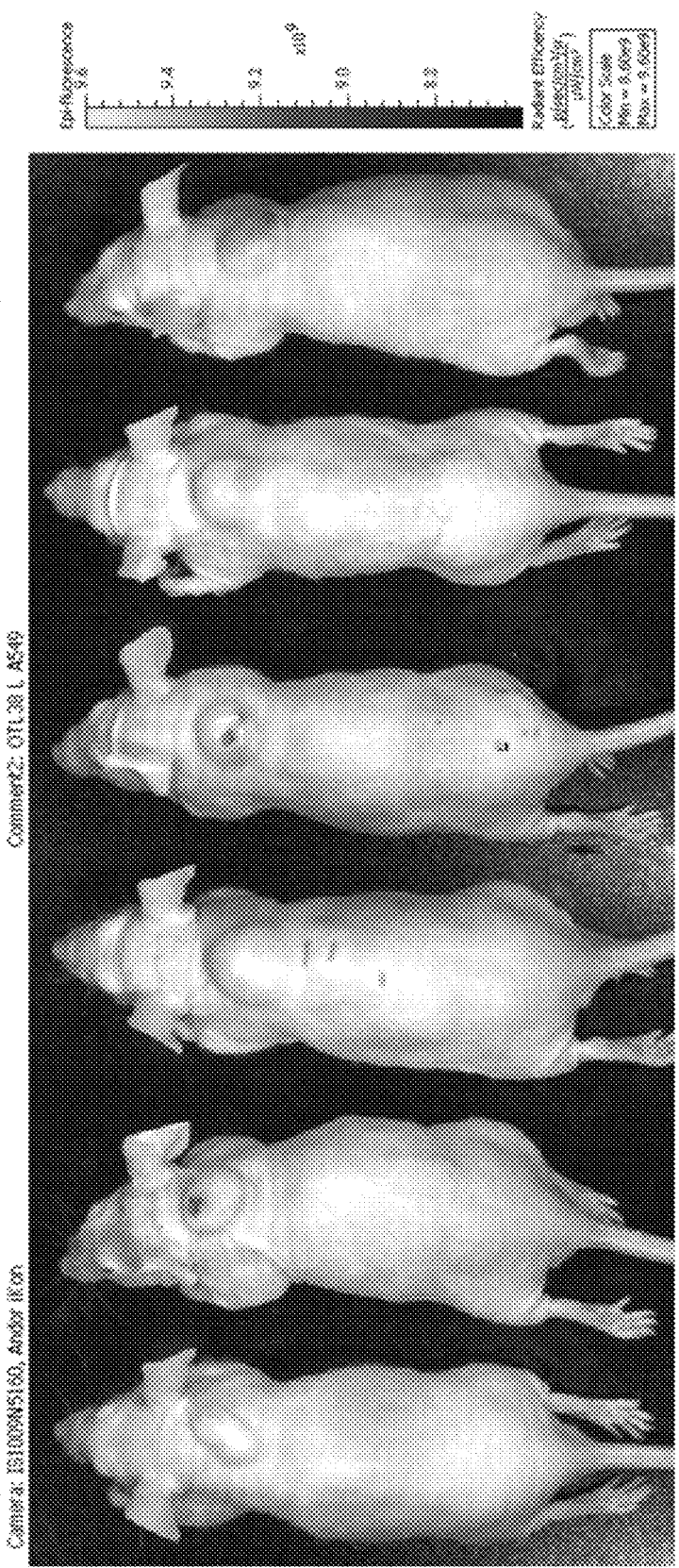
FIG. 6 depicts the whole body fluorescence image of mice bearing tumor xenografts negative for folate receptors (A549 tumor xenografts). Whole body imaging was performed 2.5 hours after administration of 10 nmol of OTL-0038.

The above schemes merely illustrate several non-limiting synthetic approaches by which the compounds disclosed herein may be prepared. It will be appreciated that one of skill in the art will be able to identify and incorporate modifications to the above schemes that would provide other compounds having the physical properties that are within the scope of the disclosure. For example, while the above Schemes illustrates folate and pteroyl groups as the targeting ligands of the compounds disclosed herein, one of skill will appreciate that other targeting ligands can be readily incorporated into the synthetic scheme and generate alternative compounds of the Formula I, such as PTE-L-Tyr-S0456 (OTL-0038) as shown in FIGS. 1 and 6. As another example, a one of skill will appreciate that the absorption/emission wavelengths of the dye portion of the compounds can be modulated by adjusting the length of the polymethine chain and selecting the appropriate aryl or heteroaryl groups (e.g., indole vs. benzoindole) as well as linking amino acid groups. In a further example, one of skill in the art will recognize that the extinction coefficient and fluorescence intensity of the dye can be varied by adjusting the rigidity of the polymethine chain (e.g., by introducing a ring system into the polymethine chain such as cyclohexene, cyclobutanone, among others) as is generally known in the art. Accordingly, one of skill in the art will be able to modify the synthesis by selecting the appropriate reagents to make any of the compounds disclosed herein and optionally being able to vary particular physical properties of the compounds.

It will be apparent to those skilled in the art that various changes may be made in the disclosure without departing from the spirit and scope thereof, and therefore, the disclosure encompasses embodiments in addition to those specifically disclosed in the specification, but only as indicated in the appended claims.

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

EXAMPLES

Example 1

General Synthesis of Pte-L Tyrosine-S0456 (OTL-0038)

Scheme:

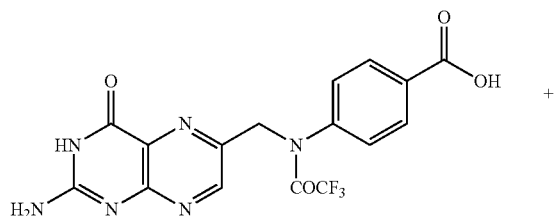

1

-continued

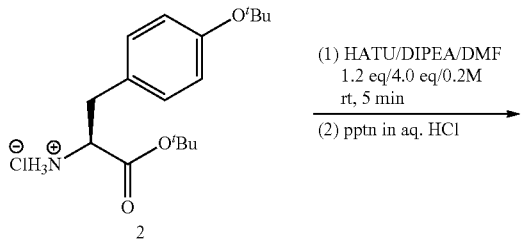

(1) HATU/DIPEA/DMF
1.2 eq/4.0 eq/0.2M
rt, 5 min (2) pptn in aq. HCl

-continued

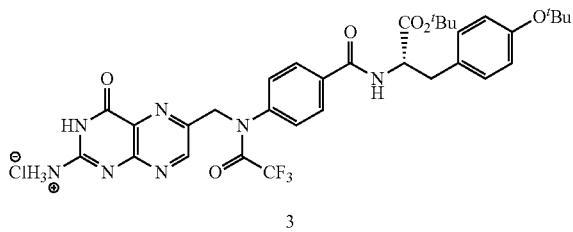

3

Reactants for Step I:

| Chemicals | Purity (%) | M.W. (g/mol) | Density (g/mL) | Equiv | Qty (g) | Qty (mL) | Mmol |
|---|---|---|---|---|---|---|---|
| Pteroic acid (1) | | 408.08 | | 1.0 | 12.00 | | 29.40 |
| (L)-Tyr(—O'Bu)—O'Bu•HCl (2) | 99 | 329.8 | | 1.2 | 11.63 | | 35.28 |
| HATU | | 381.3 | | 1.2 | 13.45 | | 35.28 |
| DIPEA | | 129.24 | 0.742 | 4.0 | | 20.48 | 117.62 |
| DMF | | | | 0.2 M | | 147 | |

A 500 mL round bottom flask was charged with a stirring bar, pteroic acid (12.0 g, 29.40 mmol, 1 equiv), (L)-Tyr(-O'Bu)-O'Bu.HCl (11.63 g, 35.28 mmol, 1.2 equiv) and HATU (13.45 g, 35.28 mmol, 1.2 equiv) then DMF (147 mL) was added to give a brown suspension [suspension A]. DIPEA (20.48 mL, 117.62 mmol, 4.0 equiv) was added slowly to suspension A at 23° C., over 5 minutes. The suspension turned in to a clear brown solution within 10 minutes of addition of DIPEA. The reaction was stirred at 23° C. for 2.5 h. Reaction was essentially complete in 30 minutes as judged by LC/MS but was stirred further for 2.5 h. The formation of Pte_N[10](TFA)_L_Tyr(-O'Bu)-O'Bu.HCl (FIG. 12) was confirmed by LC/MS showing m/z 409→m/z 684. LC/MS method: 0-50% acetonitrile in 20 mM aqueous NH$_4$OAc for 5 min using Aquity UPLC-BEH C18, 1.7 μm 2.1×50 mm column. The reaction mixture was cannulated as a steady stream to a stirred solution of aq. HCl (2.0 L, 0.28 M) over the period of 30 minutes to give light yellow precipitate of Pte_N[10](TFA)_L_Tyr(O'Bu)-O'Bu.HCl. The precipitated Pte_N[10](TFA)_L_Tyr(-O'Bu)-O'Bu.HCl was filtered using sintered funnel under aspirator vacuum, washed with water (8×300 mL) until the pH of the filtrate is between 3 and 4. The wet solid was allowed to dry under high vacuum for 12 hours on the sintered funnel. In a separate batch, where this wet solid (3) was dried under vacuum for 48 hours and then this solid was stored at −20° C. for 48 h. However, this brief storage led to partial decomposition of 3. The wet cake (58 g) was transferred to a 500 mL round bottom flask and was submitted to the next step without further drying or purification.

Reactants for Step II:

| Chemicals | Purity (%) | M.W. (g/mole) | Density (g/mL) | Equiv | Qty (g) | Qty (mL) | mMol |
|---|---|---|---|---|---|---|---|
| Pte_N[10](TFA)_L_Tyr(—O'Bu)—O'Bu•HCl (3) | | 720.14 | | 1.0 | 58 g | | 29.40 |
| TFA:TIPS:H$_2$O 95:2.5:2.5 | | | | Exss | | 200 | |

The wet solid (58 g) was assumed to contain 29.40 mmol of the desired compound (3) (i.e. quantitative yield for the step I).

A 500 mL round bottom flask was charged with a stirring bar, Pte_N[10](TFA)_L_Tyr(-O'Bu)-O'Bu.HCl as a wet cake (58 g, 29.40 mmol, 1 equiv). A solution of TFA:TIPS:H$_2$O (95:2.5:2.5, 200 mL) was added at once to give a light brown suspension. The reaction content was stirred at 23° C. for 1.5 hours and was monitored by LC/MS. The suspension became clear dull brown solution after stirring for 5 minutes. LC/MS method: 0-50% acetonitrile in 20 mM aqueous NH$_4$OAc for 5 min using Aquity UPLC-BEH C18, 1.7 μm 2.1×50 mm column. The formation of Pte_TFA_L Tyr (FIG. 12) was confirmed by showing m/z 684→m/z 572. Reaction time varies from 30 min to 1.5 hours depending on the water content of Pte_N[10](TFA)_L_Tyr(-O'Bu)-O'Bu.HCl. The reaction mixture was cannulated as a steady stream to a stirred MTBE (1.8 L) at 23° C. or 100° C. to give light yellow precipitate of Pte_TFA_L_Tyr. The precipitated Pte_TFA_L_Tyr was filtered using sintered funnel under aspirator vacuum, washed with MTBE (6×300 mL) and dried under high vacuum for 8 hours to obtain Pte_TFA_L_Tyr (14.98 g, 83.98% over two steps) as a pale yellow solid. The MTBE washing was tested for absence of residual TFA utilizing wet pH paper (pH between 3-4). The yield of the reaction was between 80-85% in different batches. The deacylated side product was detected in 3.6% as judged by LC/MS. For the different batches this impurity was never more than 5%.

Reactants for Step III:

| Chemicals | Purity (%) | M. W. (g/mole) | Density (g/mL) | Equiv | Qty (g) | Qty (mL) | mMol |
|---|---|---|---|---|---|---|---|
| Pte_TFA_L_Tyr-HCl (4) | | 607.93 | | 1.000 | 13.85 | | 22.78 |
| S0456 | | 953.44 | | 0.950 | 20.63 | | 21.64 |
| NaOH (aq. 3.75 M) | 88 | 40.00 | | 4.300 | | 26.12 | 97.96 |
| H$_2$O | | | | | | 275 | |

A 200 mL round bottom flask was charged with a stirring bar and Pte_TFA_L_Tyr (13.85 g, 22.78 mmol, 1 equiv), then water (95 mL) was added to give a yellow suspension [suspension B]. A freshly prepared solution of aqueous 3.75 M NaOH (26.12 mL, 97.96 mmol, 4.30 equiv), or an equivalent base at a corresponding temperature using dimethylsulfoxide (DMSO) as a solvent (as shown in Table 1), was added dropwise to suspension B at 23° C., giving a clear dull yellow solution over 15 minutes [solution B]. The equivalence of NaOH varied from 3.3 to 5.0 depending on the source of 4 (solid or liquid phase synthesis) and the residual TFA. Trianion 5 (FIG. 12) formation was confirmed by LC/MS showing m/z 572→m/z 476 while the solution pH was 9-10 utilizing wet pH paper. The pH of the reaction mixture was in the range of 9-10. This pH is crucial for the overall reaction completion.

solution phase synthesis provides Pte_N$^{10}$(TFA)_Tyr-OH•HCl salt and desires approximately 4.1 to approximately 4.8 equiv base as a source to hydrolyze the product. Particularly, precipitation of Pte_Tyr_S0456 was best achieved when 1 mL of reaction mixture is added dropwise to the stirred acetone (20 mL). Filtration of the precipitate and washing with acetone (3×10 mL) gave the highest purity as judged from LC/MS chromatogram.

During experimentation of this solution-phase synthesis of Pte-L Tyrosine-S0456 (OTL-0038) at different stages, some optimized conditions were observed:

Mode of Addition:

Separate TFA deprotection via trianion formation; S0456 @ 23° C.; reflux.

| Source | Purity | Linker | S0456 | Base | Solvent | Duration | % Conversion |
|---|---|---|---|---|---|---|---|
| Solution phase | 67.3% | 1 equiv | 1 equiv | 3 equiv + 2 equiv | H$_2$O [0.0875 M] | 30 min | 100% |
| Solution phase | 67.3% | 1 equiv | 1 equiv | 3 equiv + 1 equiv | H$_2$O [0.02 M] | 2 h | 100% |

Notably, pH more than 10 leads to hydrolysis of S0456. Excess base will efficiently drive reaction forward with potential hydrolysis of S0456. The presence of hydrolysis by product can be visibly detected by the persistent opaque purple/blue to red/brown color.

Mode of Addition:

Separate TFA deprotection via trianion formation; S0456 @ 100° C., addition of trianion at 100° C., reflux.

| Source | Purity | Linker | S0456 | Base | Solvent | Duration | % Conversion |
|---|---|---|---|---|---|---|---|
| Solution phase | 95% | 1 equiv | 0.95 equiv | 4.3-4.6 equiv KOH | H$_2$O | 15 min | 100% |
| Solution phase | 95% | 1 equiv | 0.95 equiv | 4.3 equiv K$_2$CO$_3$ | H$_2$O | 15 min | 100% |

TABLE 1

Separate TFA deprotection via Manion formation; S0456 @ ° C.

| Base | Equiv | Temp (° C.) | t (h) | Conversion (%) |
|---|---|---|---|---|
| KOH/25 uL H$_2$O | 3 | 23 | 2 | 85 |
| | 4.3 | 23 | 1.5 | 100 |
| | 4.3 | 80 | 0.45 | 100 |
| K$_2$CO$_3$ | 3.3 | 23 | 2 | 50 |
| | 5 | 80 | 2 | 100 |
| NaOtBu | 3.3 | 23 | 2 | 10 |
| | 6.6 | 23 | 2 | 15 |
| | 6.6 | 100 | 4 | <98 |
| NaOAc | 3.3 | 23 | 12 | >5 |
| | 13.3 | 23 | 12 | >5 |
| | 13.3 | 100 | 8 | <98 |

The precipitated OTL-0038 product could also be crashed out by adding the reaction solution steady dropwise to acetone, acetonitrile, isopropanol or ethyl acetate/acetone mixture. Acetone yields optimal results. However, viscous reactions could be slower due to partial insolubility and/or crashing out of S0456. In this reaction, the equivalence of the aqueous base is significant. Excess base will efficiently drive reaction forward with potential hydrolysis of S0456. This Stability data of Pte-L Tyrosine-S0456 (OTL-0038):

| | Liquid 5 mg per ml, 2 ml fill, PBS | | | |
|---|---|---|---|---|
| | −20 Achiral HPLC | 5 Achiral HPLC | 25 Achiral HPLC | 40 Achiral HPLC |
| 1 month (270 nm) | 95.80% | 95.88% | 94.43% | 87.17% |
| 1 month (774 nm) | 94.59% | 94.29% | 94.05% | 93.56% |

Liquid Analysis:

At 40° C. the liquid lost 8.6% at 270 nm and 1% at 774 nm. At room temperature the liquid lost about 1.4% at 270 nm and 0.5% at 774 nm. At 5° C. the 270 nm seems stable and the 774 nm reasonably stable with a small degradation in purity.

| Source | Purity | Linker | S0456 | Base | Solvent | Duration | % Conversion |
|---|---|---|---|---|---|---|---|
| Solution phase | 95% | 1 equiv | 0.95 equiv | 4.3-4.6 equiv $K_2CO_3$ | $H_2O$ | 15 min | 100% |

Example 4

Solid-Phase Synthesis of TFA-Pteroyl_Tyr

Scheme:

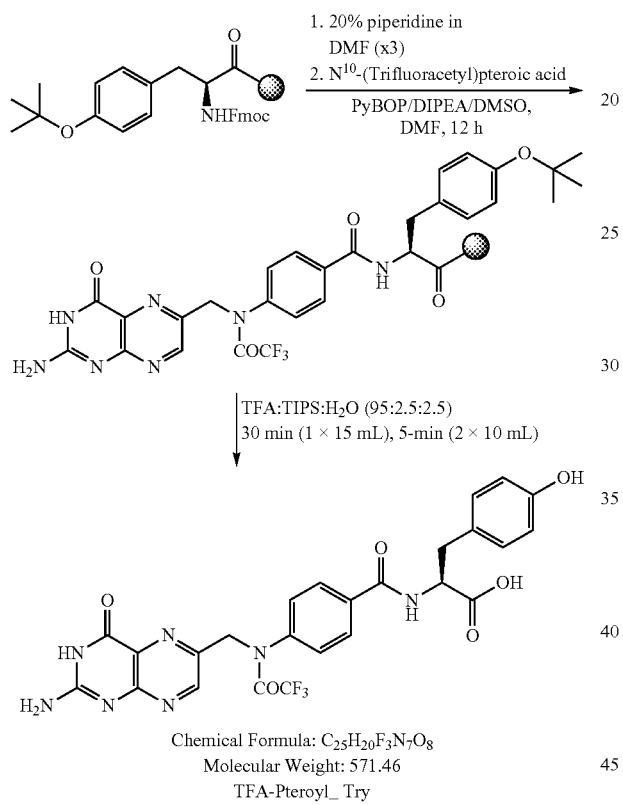

Chemical Formula: $C_{25}H_{20}F_3N_7O_8$
Molecular Weight: 571.46
TFA-Pteroyl_ Try Raw Materials:

| Reagents | Resin Loading (mmole/g) | Weight used (g's) | M.W. (g/mol) | Moles | Equivalents | Weight for addition (g) | Volume for addition (mL) |
|---|---|---|---|---|---|---|---|
| Fmoc-Tyr($^t$Bu)-Wang Resin | 0.56 | 1.000 | | 0.00056 | | 5 | |
| DIPEA (d = 0.742 g/ml) | | | 129.5 | 0.000875 | 4.0 | | 1.95 |
| HATU | | | 380.23 | 0.000875 | 1.2 | 2.129 | |
| $N^{10}$-(Trifluoroacetyl)pteroic Acid | | | 408.29 | 0.000525 | 1.2 | 1.371 | |
| TFA:$H_2O$:TIPS | | | | | | | 25 mL × 3 |

Operations:

The solid-phase synthesis of TFA-Pteroyl_Tyr was conducted on 1 g and 5 g scale of resin (loading 0.56 meq/g). The reaction was optimized with respect to various parameters such as washing time, washing volumes, volume of the wash solutions, and presence or absence of isopropanol wash equivalence of reagents, and the amount and/or temperature of the ether for precipitation.

Swell Fmoc-Tyr($^t$Bu)-Wang Resin (5 g) with DCM (50 mL) using a solid phase peptide synthesis vessel. After decanting, repeat swelling procedure with DMF (50 mL). Add 5 mL of 20% piperidine in DMF (50 mL) to the resign and bubble $Ar_2$ gas for 5 min. Repeat 2 times and then wash the resin with DMF (3×50 mL) and i-PrOH (2×50 mL). Assess formation of free amine by the Kaiser Test (test should be blue color).

Swell the resin again in DMF. Add a solution of $N^{10}$TFA-pteroic acid (1.371 g, 1.2 equiv), HATU (2.129 g, 2 equiv), and DIPEA (1.95 ml, 4 equiv) in DMF. Bubble $N_2$ gas for 4 hours and wash the resin with DMF (3×50 ml) and i-PrOH (2×50 mL). Assess coupling efficiency using the Kaiser Test (No blue color means complete loading of $N^{10}$TFA-pteroic acid). Swell the resin with DCM (50 mL) and dried under argon.

Cleave the final compound from the resin using 3 mL TFA:$H_2O$:TIPS (95:2.5:2.5) cocktail (3×25 mL, 45 min) and concentrate under vacuum. Purification and coupling to S0456 may be done as similar to the Step III in Example 15. The yield of the TFA-Pteroyl_Tyr for various batches was in the range of 68-83% and the purity was 63-91%.

Example 5

Synthesis of Pte-L Tyrosine-S0456 (OTL-0038) Using TFA-Pteroyl_Tyr Solid-Phase Precipitate A 500 mL round bottom flask was charged with a stirring bar, Pte_$N^{10}$(TFA)_Tyr-OH from solid phase synthesis (5 g, 1.2 equiv), S0456 (20.63 g, 21.64 mmol, 1.0 equiv), then water (180 mL, 0.03 M) was added to give a suspension. The S0456 fluorescent dye can be added to the Pte_$N^{10}$(TFA)_Tyr-OH either before or after deprotection via separate trianion formation with the aqueous base and still result in an equally viable product. A freshly prepared solution of aqueous 3.75 M NaOH (26.12 mL, 97.96 mmol, 3.0 equiv), or an equivalent base at a corresponding temperature (as shown in Table 1), was added dropwise to the suspension at 80° C., giving a clear dull yellow solution over 3 h. The pH of the reaction mixture was in the range of 9-10. This pH is crucial for the overall reaction completion. Notably, pH more than 10 leads to hydrolysis of S0456. The presence of hydrolysis by product can be visibly detected by the persistent opaque purple/blue to red/brown color. The reaction was monitored by LC/MS. LC/MS method: 0-50% acetonitrile in 20 mM aqueous $NH_4OAc$ for 5 min using Aquity UPLC-BEH C18, 1.7 μm 2.1×50 mm column. Formation of OTL-0038 was confirmed by LC/MS showing m/z 476→m/z 1326 and m/z 664 (FIG. 16A). The reaction mixture was cooled to room temperature then was transferred via cannula as a steady stream to a stirred acetone (5.5 L) to give green precipitate. The precipitated OTL-0038 was filtered under aspirator vacuum on sintered funnel washed with acetone (3×10 mL). The green powdery solid was dried under high vacuum for 12 hours to obtain OTL-0038 (31 g) quantitatively with 92.8% purity. The additional mass in the final product can be attributed to residual NaCl, $CF_3COONa$, NaOH and water. These salts can be removed by using desalting column. Alternatively, the Pte-L Tyrosine-S0456 (OTL-0038) product was purified and collected by reverse phase-high pressure liquid chromatography (RP-HPLC) methods (yielding a 87% conversion). Purification may be done as similar to the method in Example 15.

The precipitated OTL-0038 product could also be crashed out by adding the reaction solution steady dropwise to acetone, acetonitrile, isopropanol or ethyl acetate/acetone mixture (wherein acetone will yield the best results). However, viscous reactions could be slower due to partial insolubility and/or crashing out of S0456. In this reaction, the equivalence of the aqueous base is crucial. Excess base will efficiently drive reaction forward with potential hydrolysis of S0456. Normally 3.3 equiv base is enough for a clean reaction without side products. This solid phase synthesis provides Pte_$N^{10}$(TFA)_Tyr-OH (needs 3.3 equiv base as a crucial source to hydrolyze the product). Particularly, precipitation of Pte_Tyr_S0456 was best achieved when 1 mL of reaction mixture is added dropwise to the stirred acetone (20 mL). Filtration of the precipitate and washing with acetone (3×10 mL) gave the highest purity as judged from LC/MS chromatogram.

During experimentation of this solid-phase synthesis of Pte-L Tyrosine-S0456 (OTL-0038) at different stages, some optimized conditions were observed:

Mode of Addition:
Separate TFA deprotection via trianion formation; S0456 @ 23° C.; reflux.

| Source | Purity | Linker | S0456 | Base | Solvent | Duration | % Conversion |
|---|---|---|---|---|---|---|---|
| Solid phase | 63% | 1 equiv | 1 equiv | 3 equiv + 3 equiv | $H_2O$ [0.125 M] | 28 h | 50% |

Mode of Addition:
Mixing linker and S0456; then base @ 23° C. for 15 minutes; reflux.

| Source | Purity | Linker | S0456 | Base | Solvent | Duration | % Conversion |
|---|---|---|---|---|---|---|---|
| Solid phase | 63% | 1 equiv | 1 equiv | 3 equiv | $H_2O$ [0.0625 M] | 15 h | 59% |

Stability data of Pte-L Tyrosine-S0456 (OTL-0038):

| | Lyophilization 5 mg per ml, 2 ml fill, Water | | | |
|---|---|---|---|---|
| | −20 Achiral HPLC | 5 Achiral HPLC | 25 Achiral HPLC | 40 Achiral HPLC |
| 1 month (270 nm) | 95.80% | 95.88% | 94.43% | 87.17% |
| 1 month (774 nm) | 94.59% | 94.29% | 94.05% | 93.56% |

Lyophilization Analysis:
At 40° C. the lyophilized product lost 4.5% at 270 nm and 1.1% at 774 nm; at room temperature the lyophilized product was stable at the first month and was stable at less than room temperature for the first month.

The following examples illustrate the syntheses of several analog amino acid linkers to Pte-L Tyrosine-S0456.

Example 6

Synthesis of $^{13}C$ Analog of Pte-L Tyrosine-S0456 (OTL-0040)

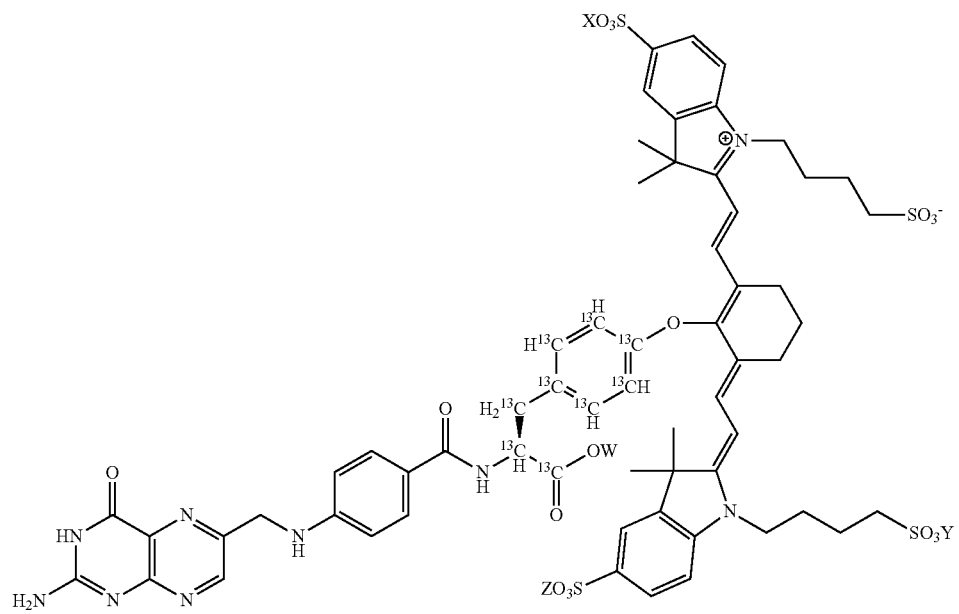
Step I: Preparation of Pte_N[10]-TFA__[13]C9_L-Tyr(O[t]Bu)-O[t]Bu (8)
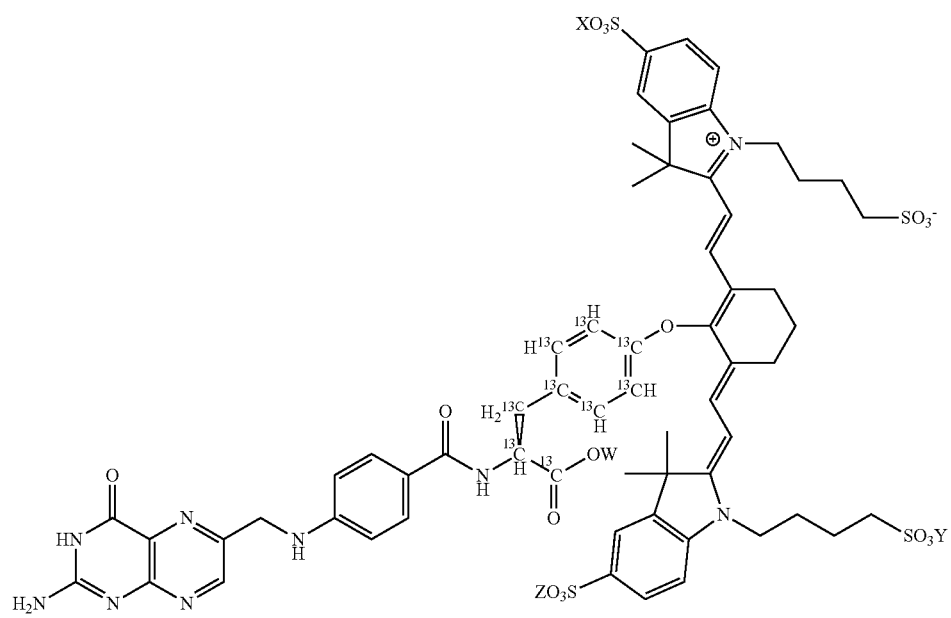

Step II: Preparation of Pte_$^{13}$C9-L-Tyr-OH (9)
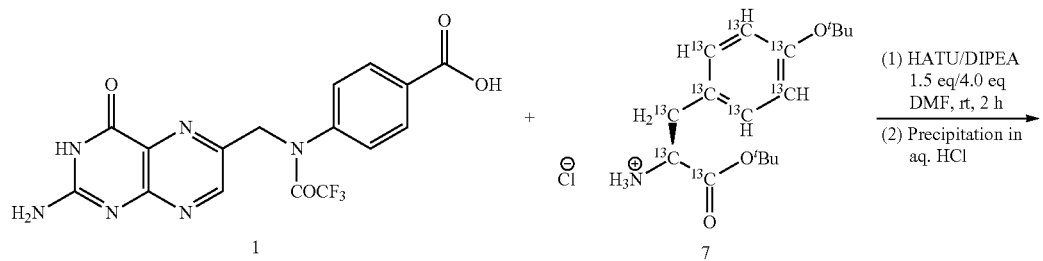
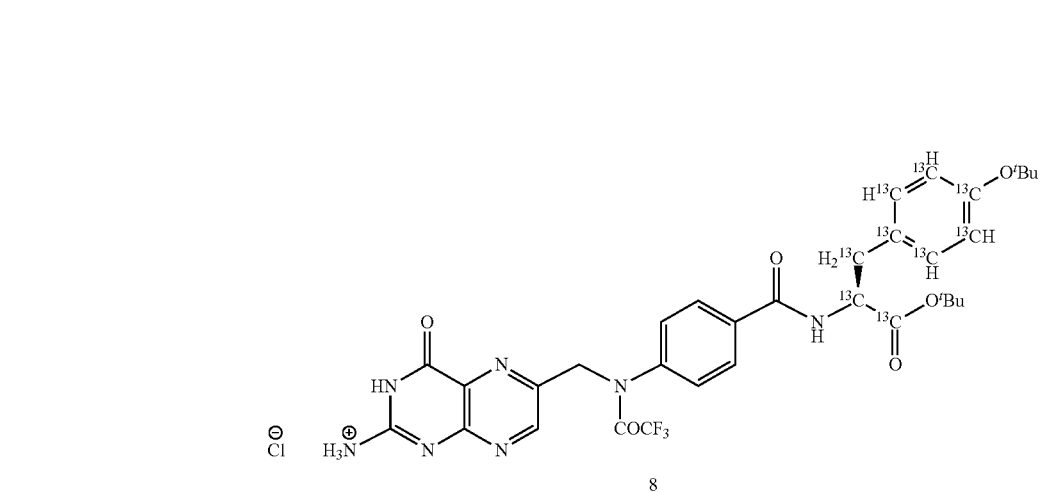
Step III: Preparation of $^{13}$C analog of Pte-L Tyrosine-S0456 (OTL-0040) (11)
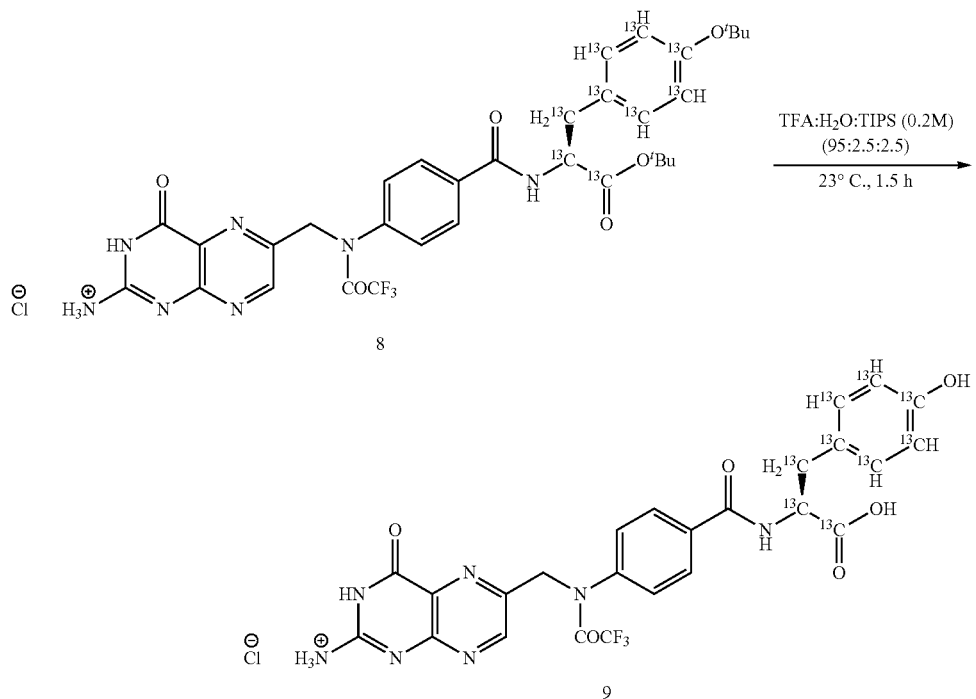
Example 7

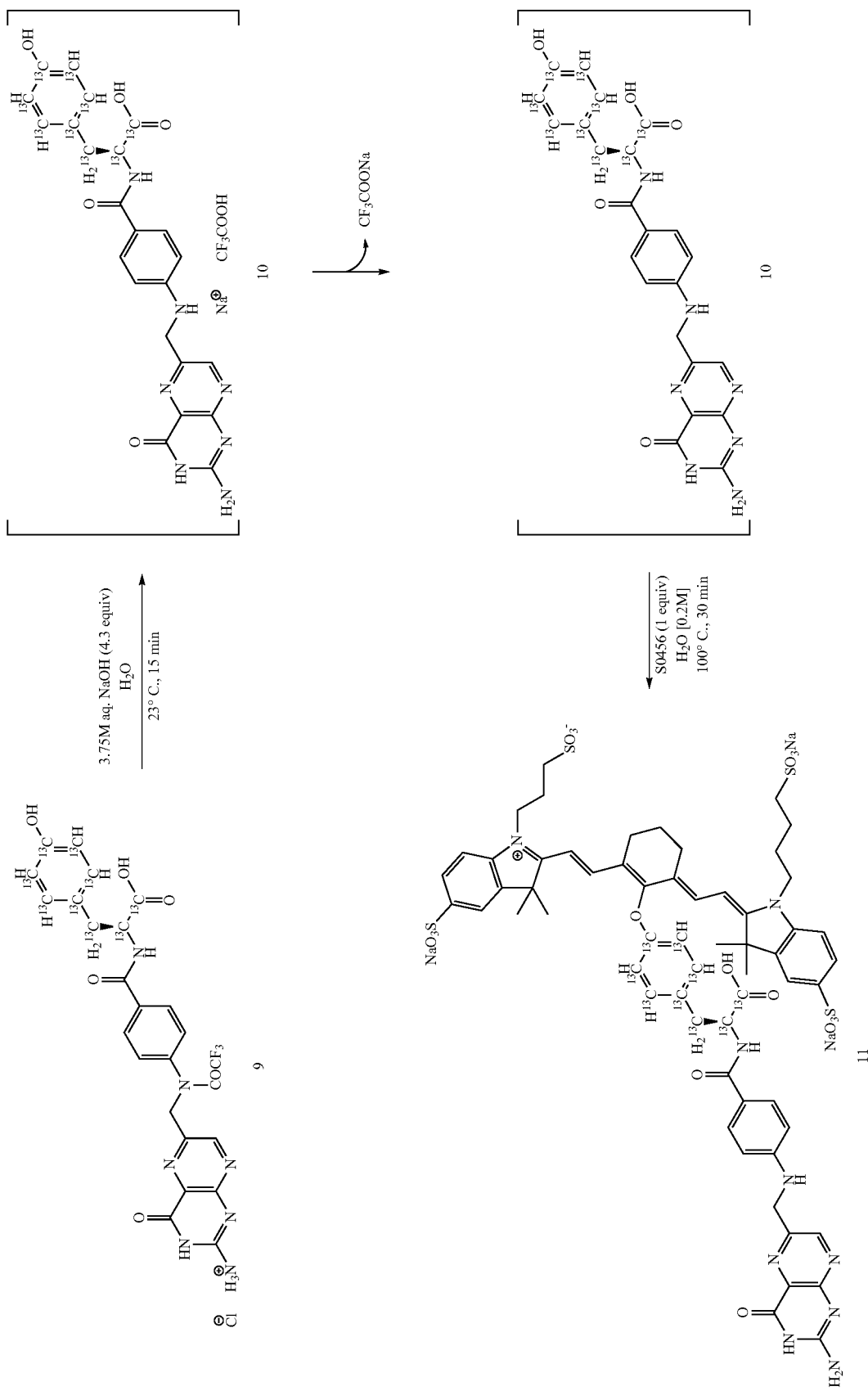

Synthesis of $^{14}$C Analog of Pte-L Tyrosine-S0456 (OTL-0041)
Step I: Preparation of Pte_N$^{10}$-TFA__$^{14}$C9-L-Tyr(O$^t$Bu)-O$^t$Bu (13)
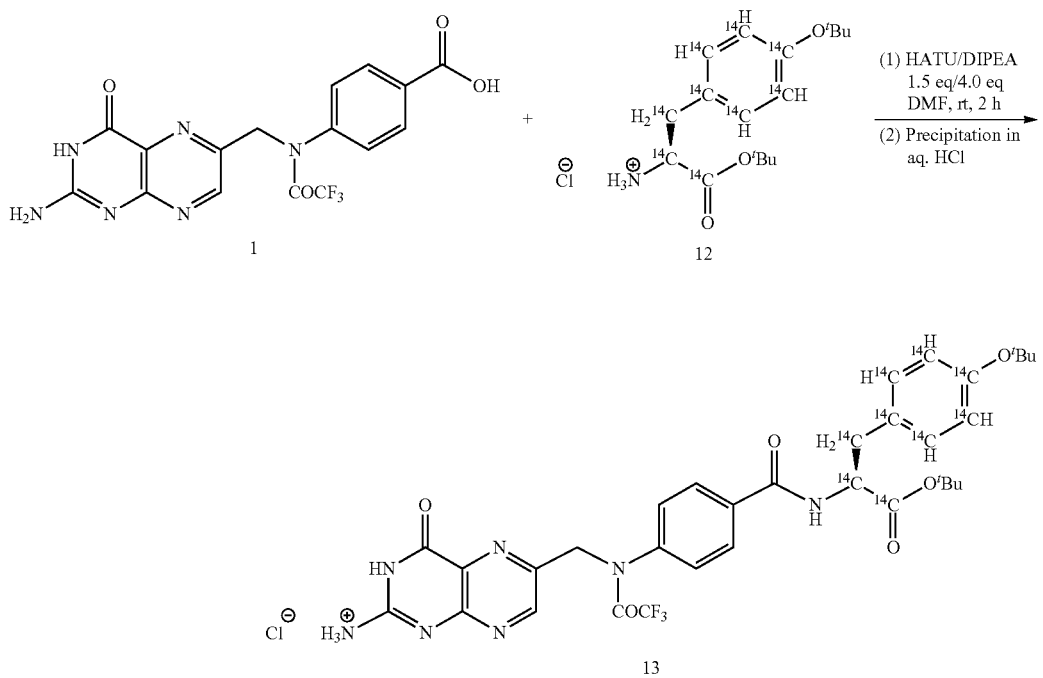
Step II: Preparation of Pte__$^{14}$C9-L-Tyr-OH (14)
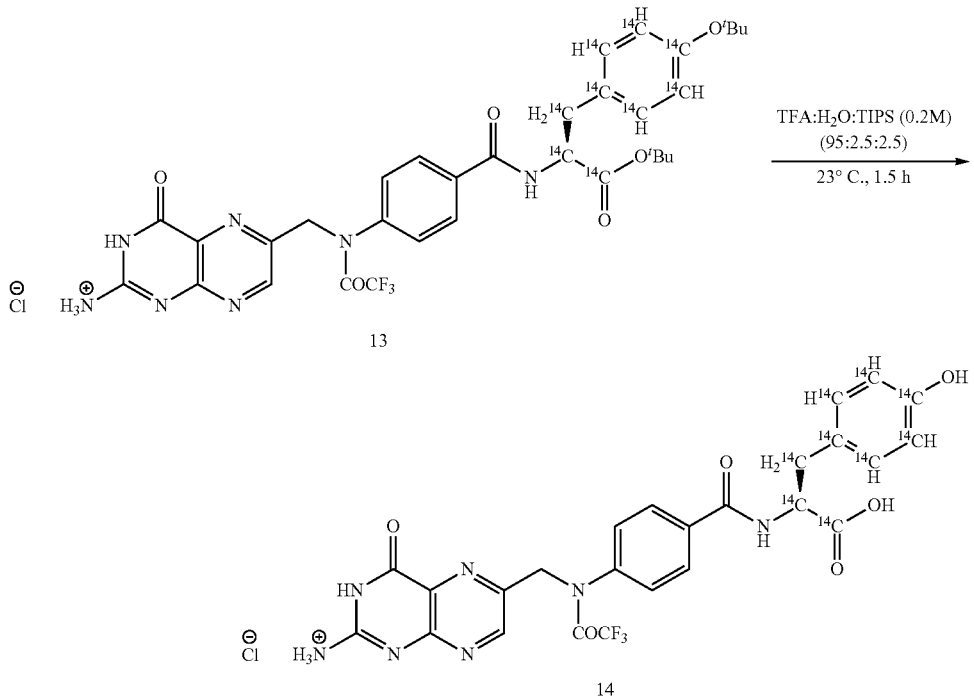
Step III: Preparation of $^{14}$C analog of Pte-L Tyrosine-S0456 (OTL-0041) (16)

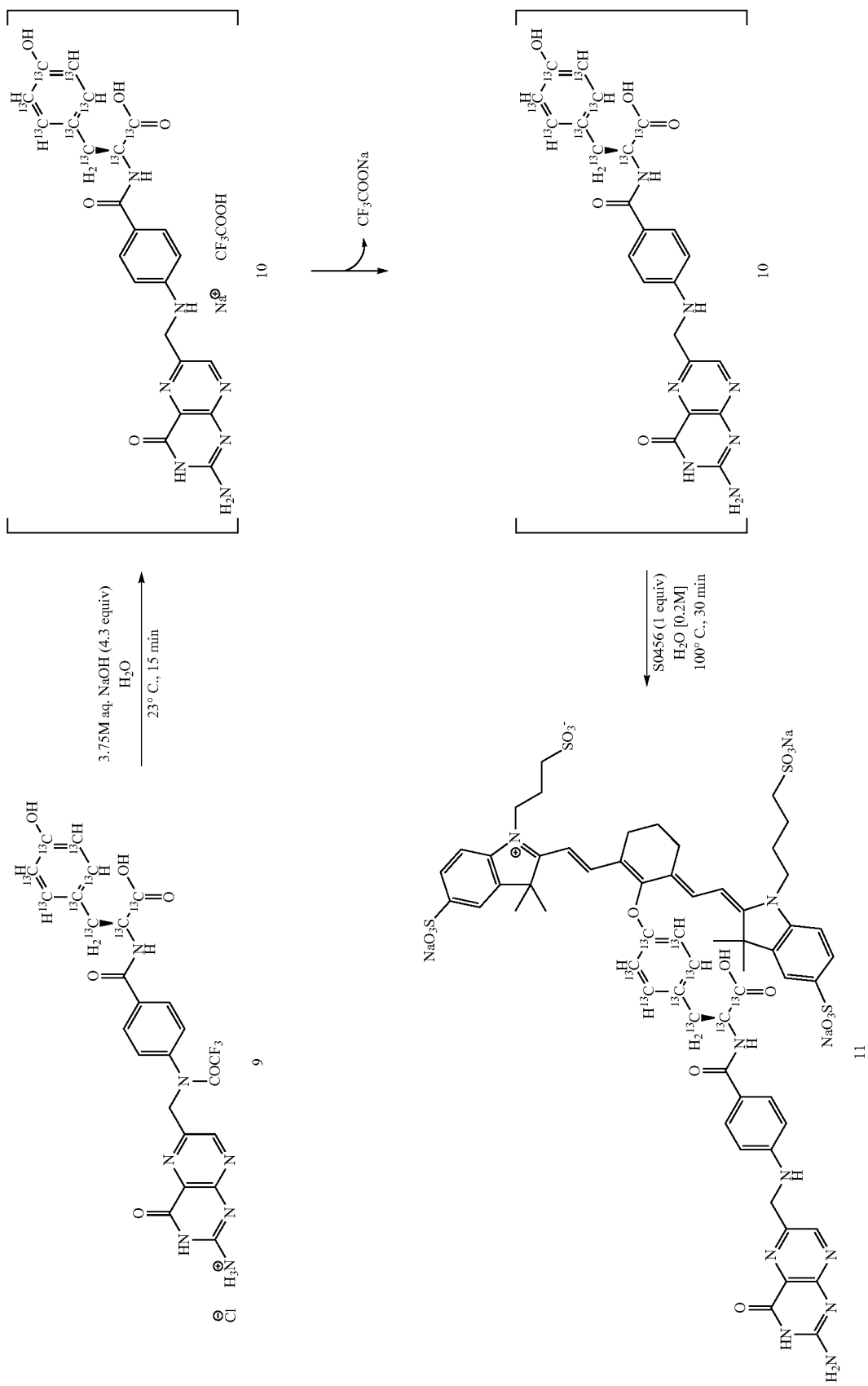

Example 8

Synthesis of $^2$H Analog of Pte-L Tyrosine-S0456 (OTL-0042)

Step I: Preparation of (S)-6-((N-(4-((1-(tert-butoxy)-1-oxo-3-(2,3,5,6-tetradeutero-4-(tert-butoxy)phenyl)propan-2-yl)carbamoyl)phenyl)-2,2,2-trifluoroacetamido)methyl)-4-oxo-3,4-dihydropteridin-2-aminium chloride (3)

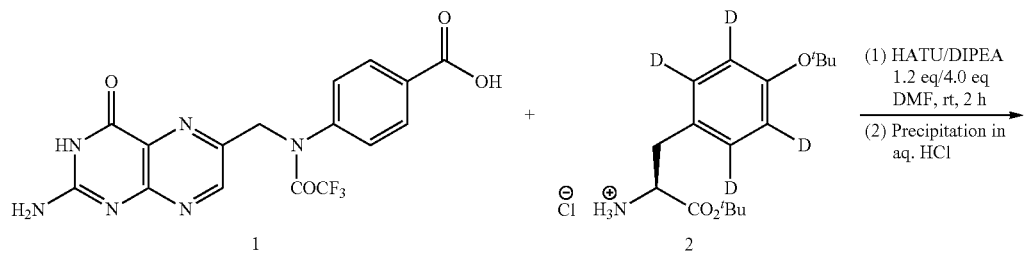

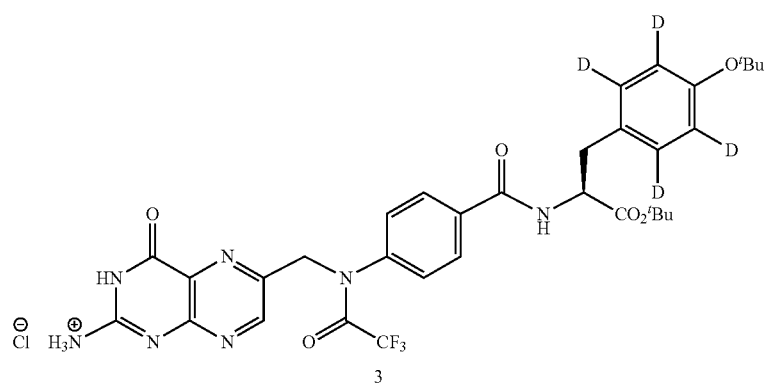

Step II: Preparation of (S)-6-((N-(4-((1-(hydroxy)-1-oxo-3-(2,3,5,6-tetradeutero-4-(hydroxy)pheny-l)propan-2-yl)carbamoyl)phenyl)-2,2,2-trifluoroacetamido)methyl)-4-oxo-3,4-dihydropteridin-2-aminium chloride (4)

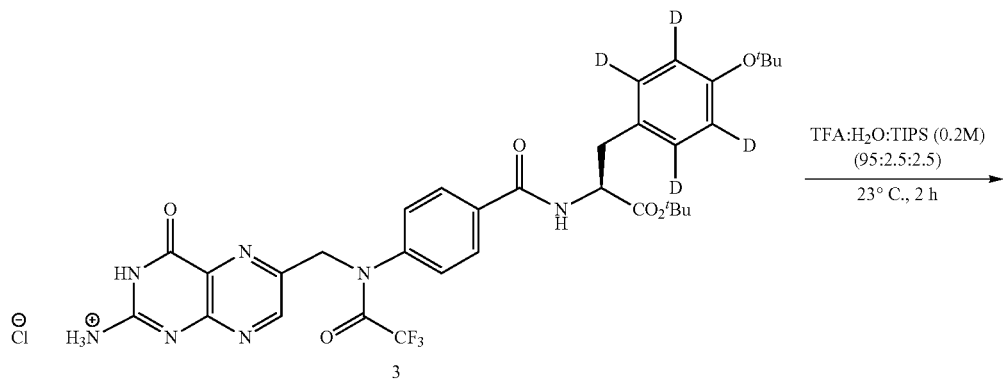

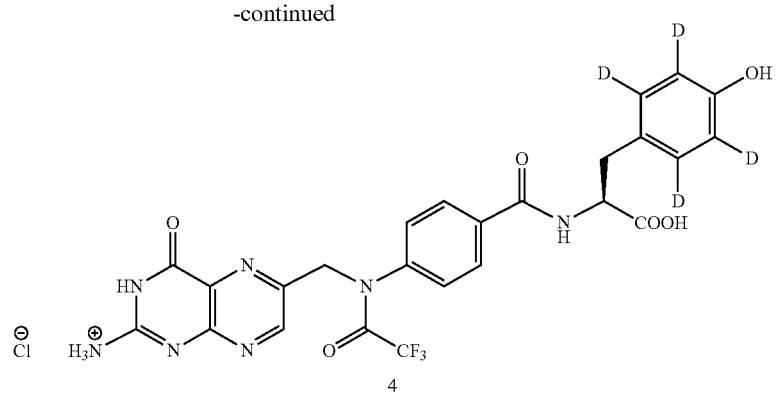
Step III: Preparation of OTL-0042 (6)

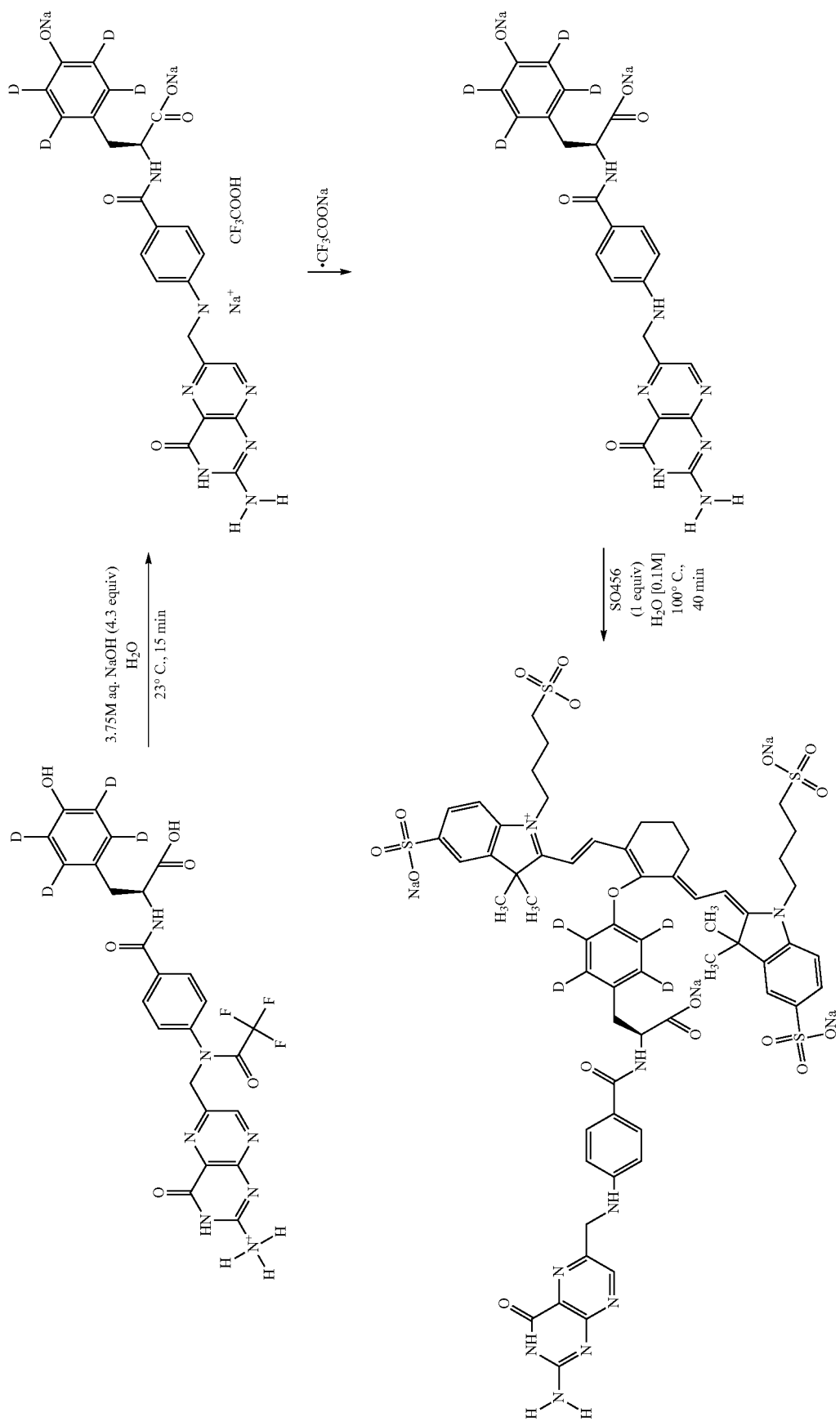

A 10 mL round bottom flask was charged with a stirring bar and (4) (346 mg, 0.601 mmol, 1 equiv), then water (6 mL) was added to give a yellow suspension [suspension A]. A freshly prepared solution of aqueous 3.75 M NaOH (0.689 mL, 2.584 mmol, 4.30 equiv) was added dropwise to suspension A at 23° C., giving a clear dull yellow solution over 15 minutes [solution B]. Trianion 5 formation was confirmed by LC/MS while the solution pH was 9-10 utilizing wet pH paper. A 25 mL round bottom flask was charged with a stirring bar and S0456 (573 mg, 0.601 mmol, 1.0 equiv), then water (3 mL) was added to give an opaque green solution

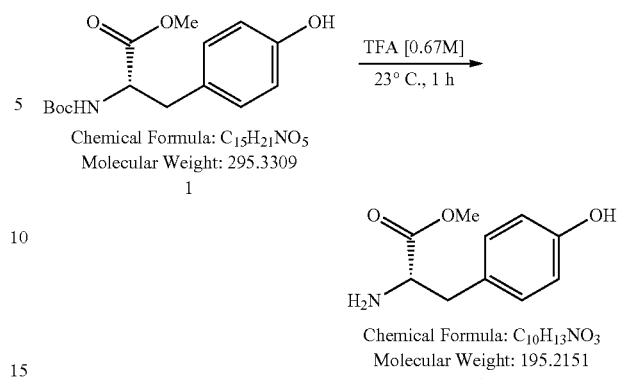

Example 9

Synthesis of Pte_Tyr(OMe)_S0456

Step I: Preparation and Boc deprotection of methyl 2-di-tert-butyl dicarbonate-amino-3-(4-phenyl)propanoate (1) as shown in the following schematic Step II: Conjugation methyl 2-di-tert-butyl dicarbonate-amino-3-(4-phenyl)propanoate to Pteroic acid

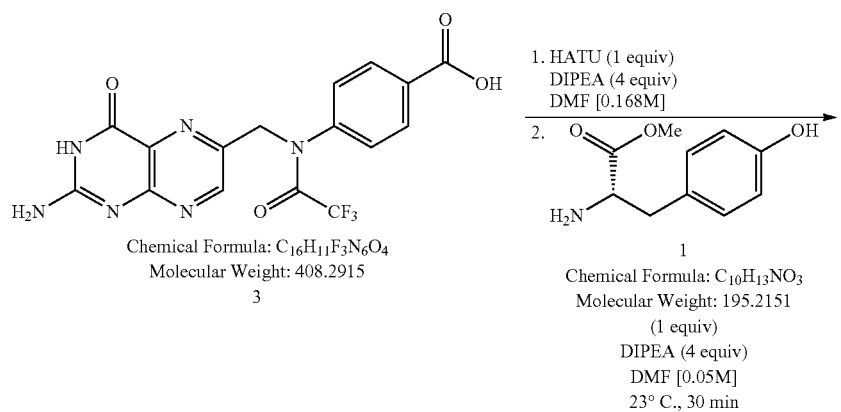

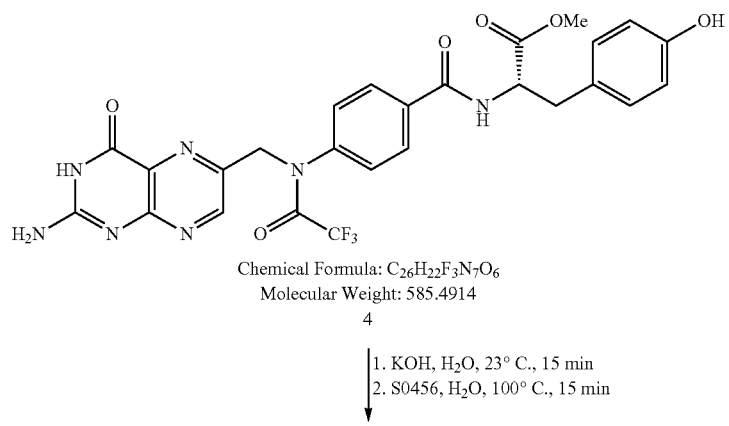

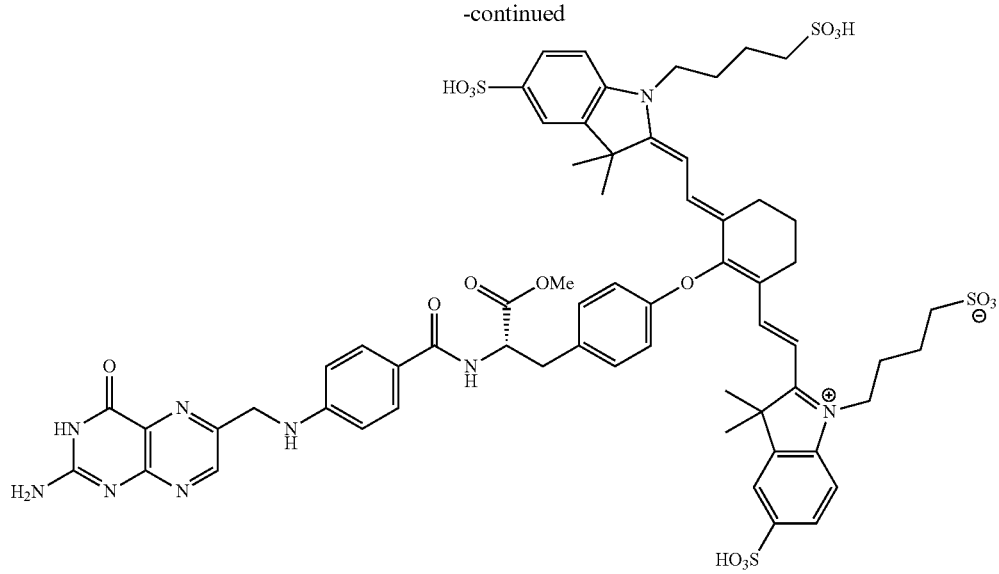
Chemical Formula: $C_{62}H_{69}N_9O_{17}S_4$
Molecular Weight: 1340.5214
5
Step III: Synthesis of Pte_Tyr(OMe)_S0456
Example 10
Synthesis of Pte_N(Me)Tyr_S0456
Step I: Preparation and Boc deprotection of Tyr(BocNMe) (6)
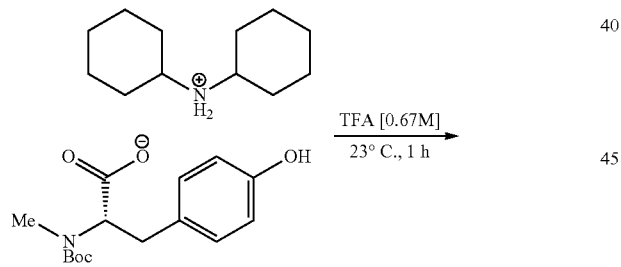
Chemical Formula: $C_{27}H_{44}N_2O_6$
Molecular Weight: 476.6487
6
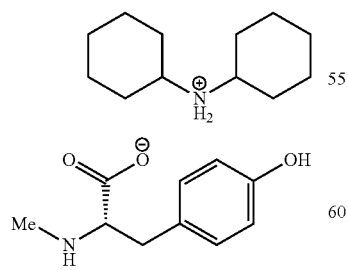
Chemical Formula: $C_{22}H_{36}N_2O_3$
Molecular Weight: 376.5328
7

Step II: Conjugation of Tyr(NMe) to Pteroic acid

3
Chemical Formula: C₁₆H₁₁F₃N₆O₄
Molecular Weight: 408.2915

1. HATU (1 equiv)
   DIPEA (4 equiv)
   DMF [0.168M]
2.

7
Chemical Formula: C₁₀H₁₃NO₃
Molecular Weight: 195.2151
(1 equiv)
DIPEA (4 equiv)
DMF [0.05M]
23° C., 1 h

8
Chemical Formula: C₂₆H₂₂F₃N₇O₆
Molecular Weight: 585.4914

1. KOH, H₂O, 23° C., 15 min
2. S0456, H₂O, 100° C., 15 min

9
Chemical Formula: C₆₂H₆₉N₉O₁₇S₄
Molecular Weight: 1340.5214

Step III: Synthesis of Pte_Tyr(NMe)_S0456

Example 11

Synthesis of Pte_(Homo)Tyr_S0456
Step I: Preparation and Boc deprotection of Tyr(HNBoc) (6)

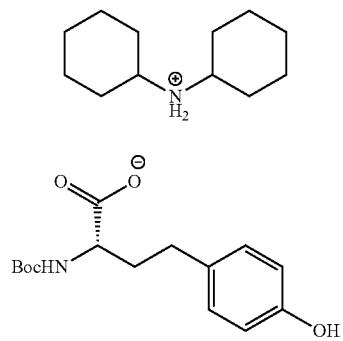

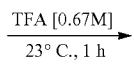 TFA [0.67M]
23° C., 1 h

Chemical Formula: $C_{27}H_{44}N_2O_5$
Molecular Weight: 476.6487
10

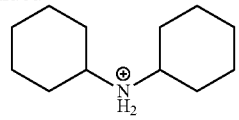

Chemical Formula: $C_{22}H_{36}N_2O_3$
Molecular Weight: 376.5328
11

Step II: Conjugation of 2-amino-4-(4-hydroxyphenyl)butanoic acid to Pteroic acid

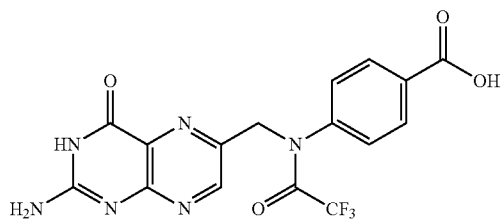

Chemical Formula: $C_{16}H_{11}F_5N_6O_4$
Molecular Weight: 408.2915
3

1. HATU (1 equiv)
   DIPEA (4 equiv)
   DMF [0.168M]

2. 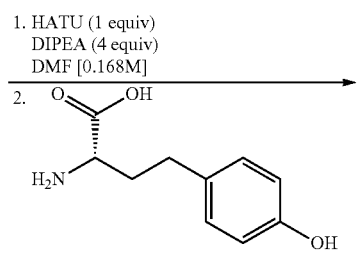

11
(1 equiv)
DIPEA (4 equiv)
DMF [0.05M]
23° C., 1 h

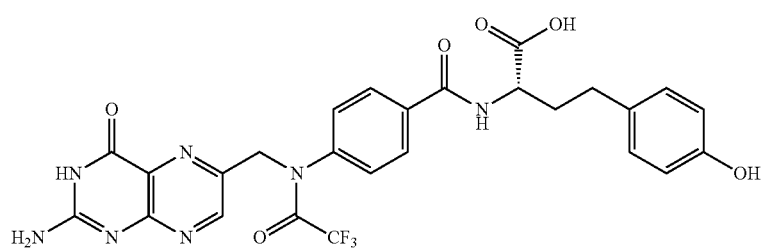

Chemical Formula: $C_{26}H_{22}F_3N_2O_6$
Molecular Weight: 585.4914
12

1. KOH, H₂O, 23° C., 15 min
2. S0456, H₂O, 100° C., 15 min

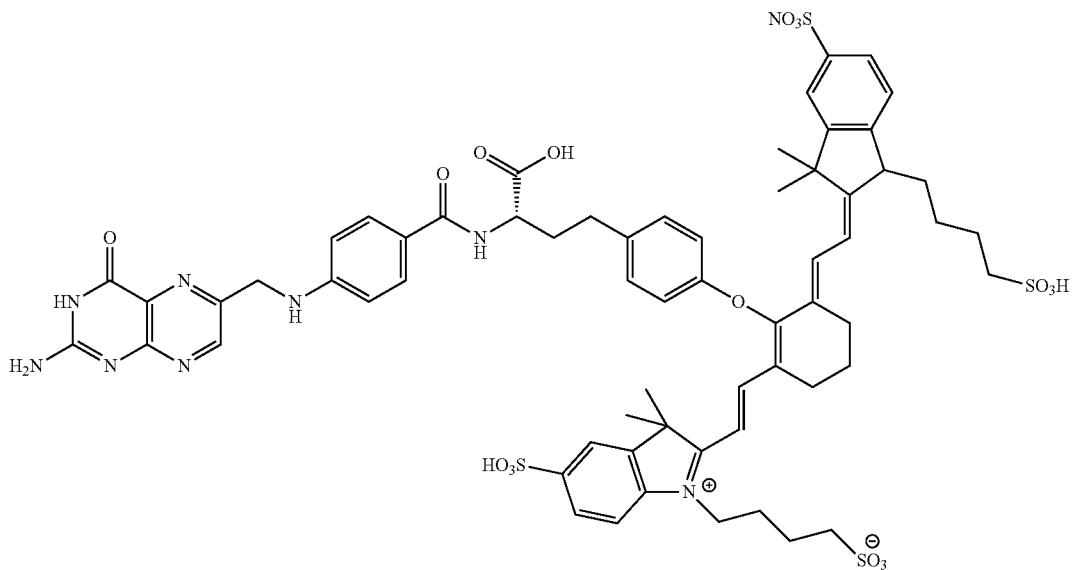
Chemical Formula:
$C_{62}H_{69}N_9O_{17}S_4$
Molecular Weight: 1340.5214
13
Step III: Synthesis of Pte_(Homo)Tyr_S0456
Example 12
Synthesis of Pteroyl-L Tyr-S0456 (OTL-0045)
Step II: Conjugation of Tyr(NNH$_2$)—NHOCH$_3$ to Pteroic acid
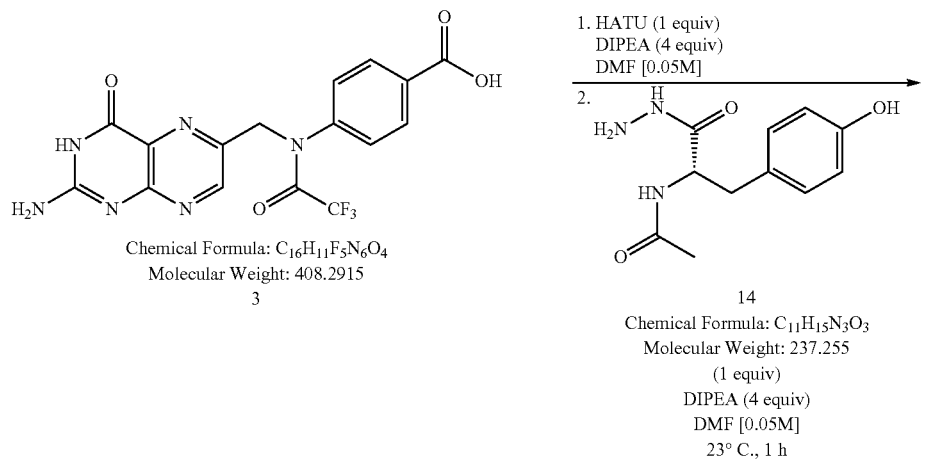

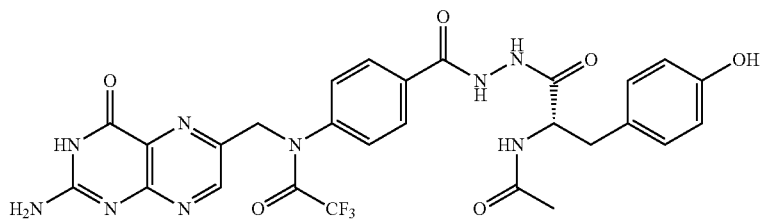
Chemical Formula: $C_{27}H_{24}F_3N_9O_6$
Molecular Weight: 627.5314
15
1. KOH, $H_2O$, 23° C., 15 min
2. S0456, $H_2O$, 100° C., 15 min
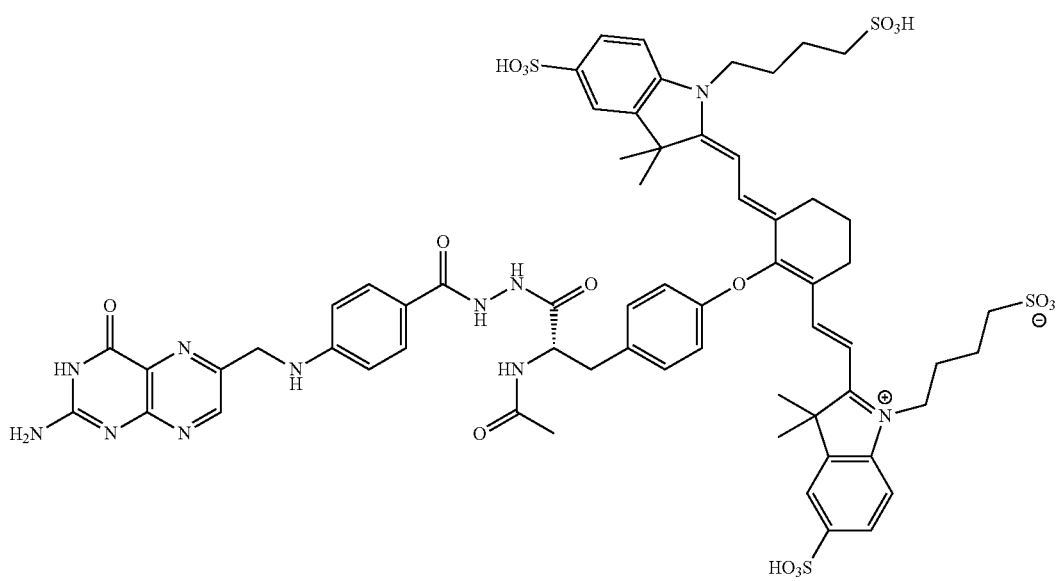
Chemical Formula:
$C_{63}H_{71}N_{11}O_{17}S_4$
Molecular Weight: 1382.5613
16
Step III: Synthesis of Pte_(Homo)Tyr(NHNH)_S0456
Example 13
Synthesis of Pte_Tyr(OBn)_S0456
Step I: Preparation and Boc deprotection of Tert-butyl (2-di-tert-butyl dicarbonate-amino)-3-(4-hydroxyphenyl) propanoate (17)
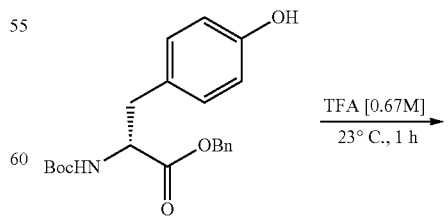
Chemical Formula: $C_{21}H_{23}NO_5$
Molecular Weight: 371.4269
17

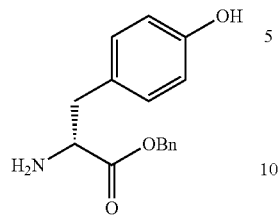
Chemical Formula: C₁₆H₁₇NO₃
Molecular Weight: 271.3111
18
Step II: Conjugation of Tert-butyl (2-di-tert-butyl dicarbonate-amino)-3-(4-hydroxyphenyl)propanoate to Pteroic acid
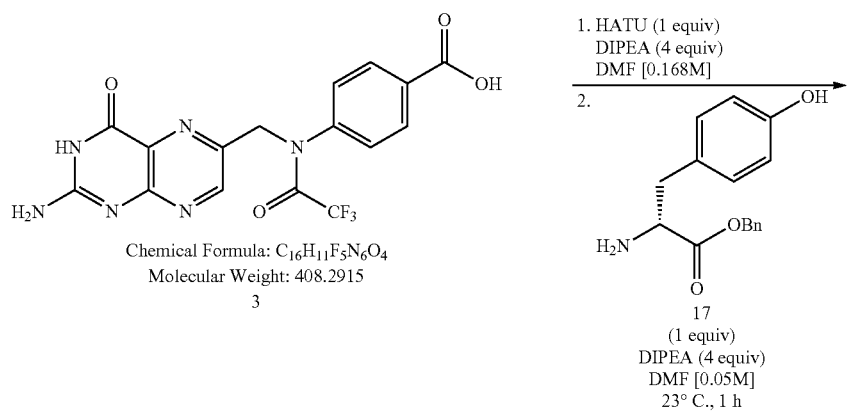
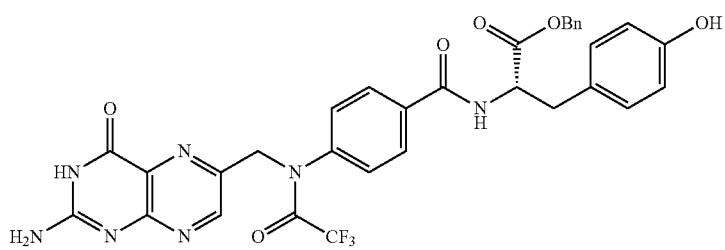
Chemical Formula: C₃₂H₂₆F₃N₇O₆
Molecular Weight: 661.5873
18
1. KOH, H₂O, 23° C., 15 min
2. S0456, H₂O, 100° C., 15 min

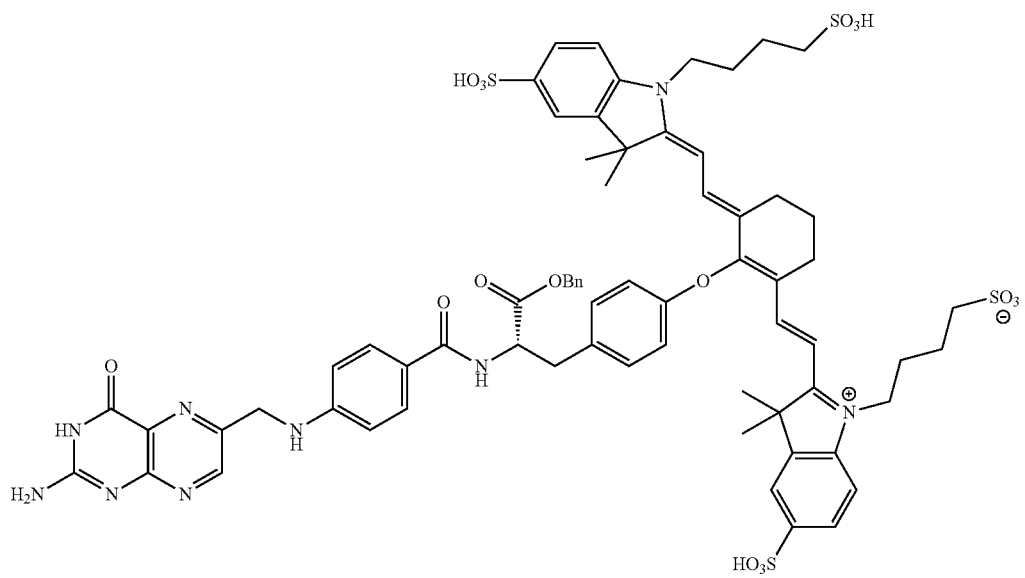
Chemical Formula: $C_{68}H_{73}N_9O_{17}S_1$
Molecular Weight: 1416.6713
19
Step III: Synthesis of Pte_Tyr(OBn)_S0456
Example 14
Synthesis of Pte_Tyr(OBn)_S0456 from Pte_Tyr(ONa)_S0456
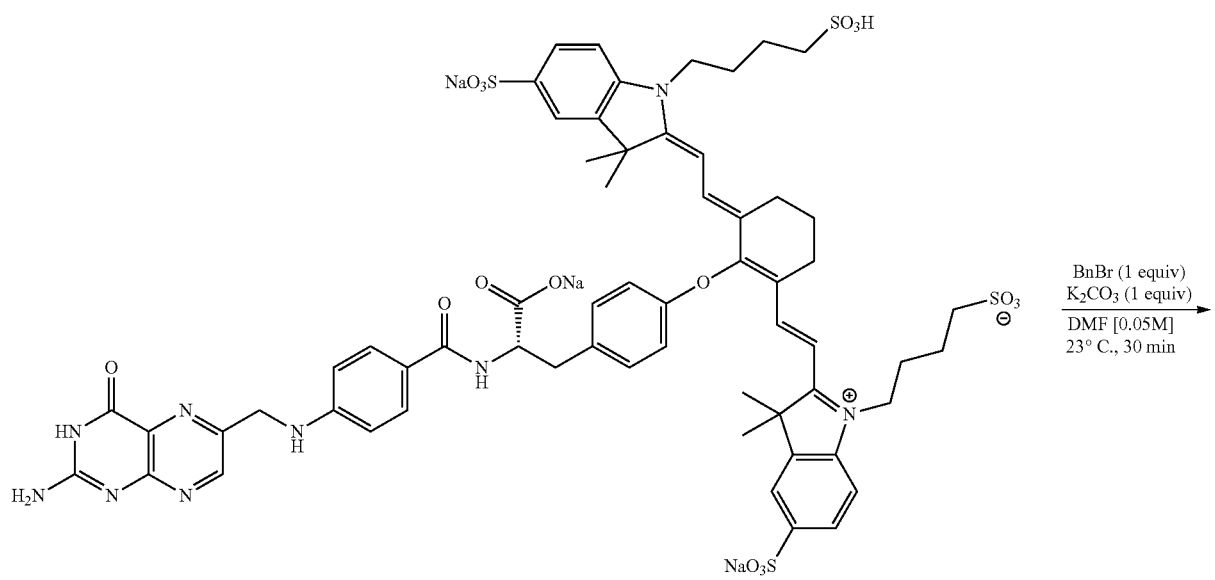
Chemical Formula: $C_{61}H_{63}N_9O_{17}S_4$
Molecular Weight: 1414.4221
20

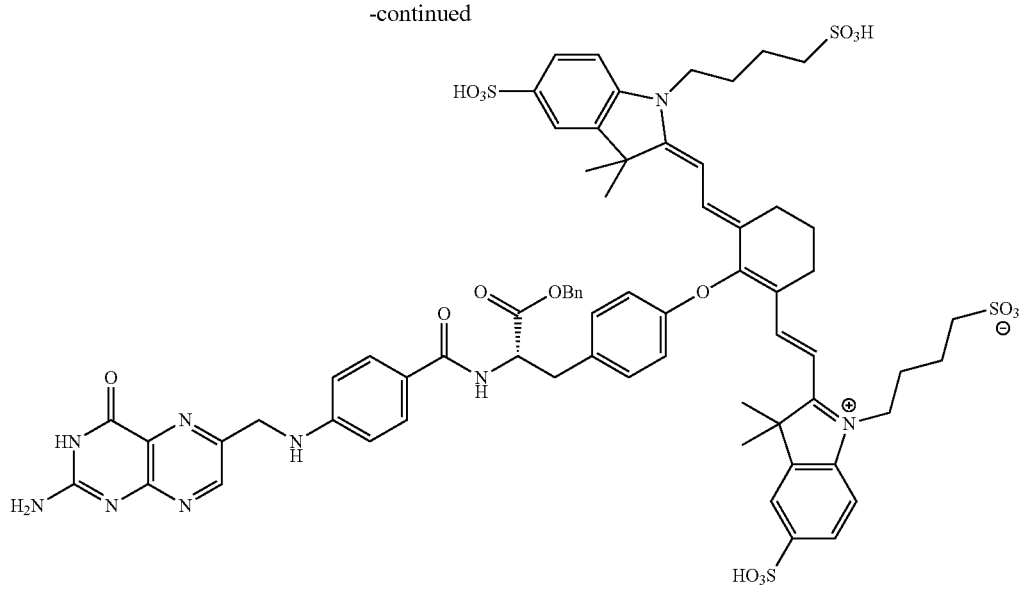

Chemical Formula: $C_{68}H_{73}N_9O_{17}S_4$
Molecular Weight: 1416.6173
21

Example 15

Purification of Pte_L_Tyr S0456 (OTL-0038)

Figure 12B:
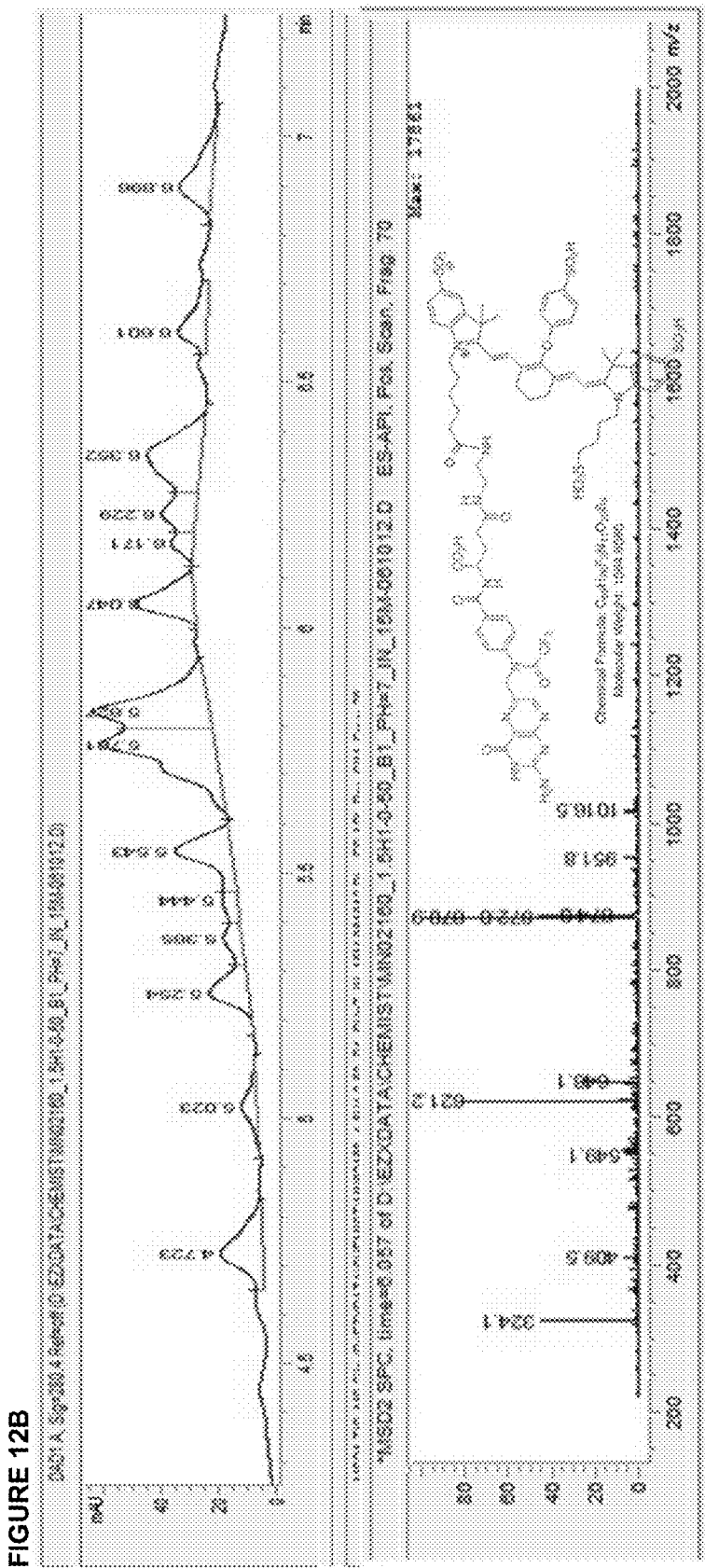
FIG. 12B illustrates monitoring of reaction progress of folate-EDA-IR800CW by LC/MS.

Pte_L_Tyr_S0456 (OTL-0038) (31 g) was dissolved in water (250 mL) and stirred for 30 minutes. This dark green opaque solution was filtered through cotton and rinsed the flask and cotton with water (50 mL). This solution was then added as a steady stream to stirred IPA (3.0 L) over the period of 30 min. The precipitated green solid was allowed to settle for 1 h. The colored (orange/brown) supernatant was decanted (.about.2.5 L) and the residual suspension was diluted with 300 mL) of IPA, filtered through the sintered funnel under aspirator vacuum. Washed the solid with IPA (2×300 mL) and acetone (2×300 mL). The partially dried solid was transferred to 250 mL RB flask and dried under high vacuum for 24 hours to obtain 30.3 g Pte_L_Tyr_S0456 (OTL-0038) in 92.98% purity. (FIG. 12).

Example 16

Repurification of Pte_L_Tyr_S0456 (OTL-0038)

Figure 5:
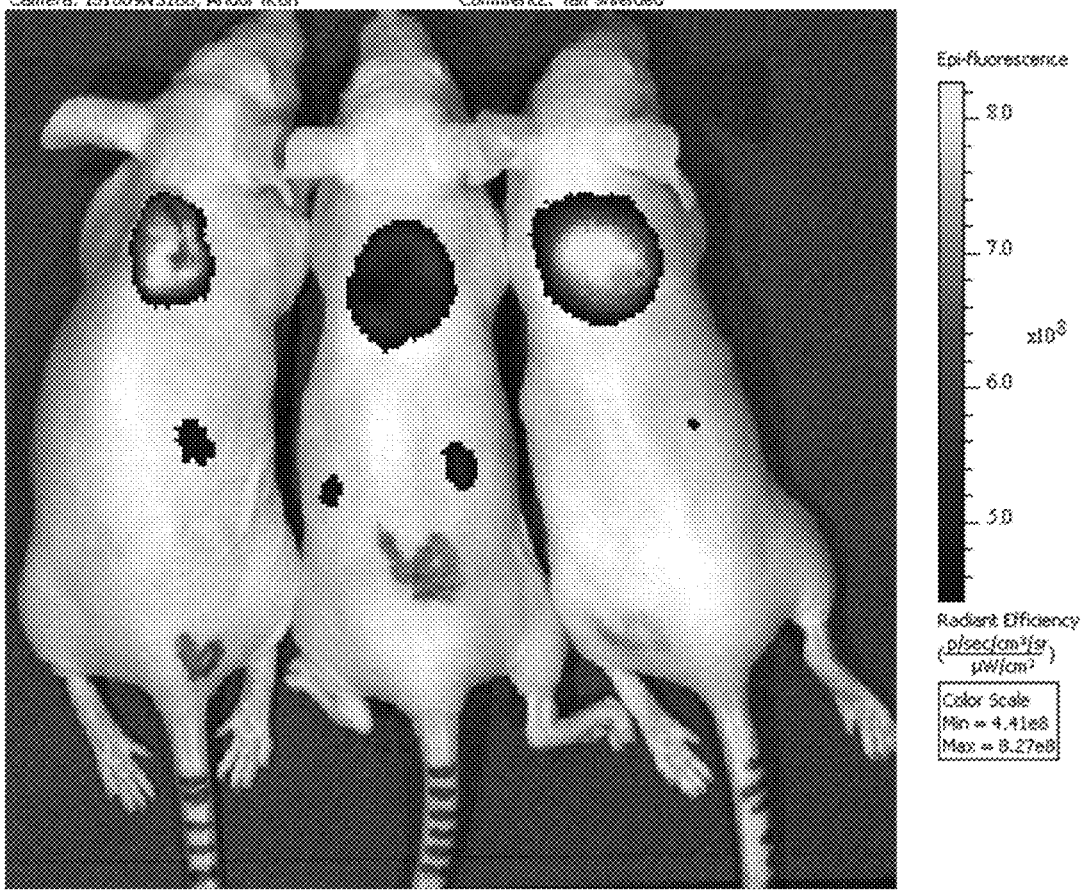
FIG. 5 illustrates the whole body fluorescence imaging of nude mice with KB tumor xenografts injected with 1 nmol of OTL-0038 (1/10 of normal dose). After 2.5 hours, animals were euthanized by $CO^2$ asphyxiation. Whole body imaging experiments were then performed using a Caliper IVIS Lumina II Imaging Station with Living Image 4.0 software.

Pte_L_Tyr_S0456 (OTL-0038) (30.3 g) was dissolved in water (250 mL) and stirred for 30 minutes. This dark green opaque solution was filtered through cotton and rinsed the flask and cotton with water (50 mL). This solution was then added as a steady stream to stirred IPA (3.7 L) over the period of 30 min. The precipitated green solid was allowed to settle for 2 h. No settling of precipitated solid was observed at this point. Acetone (1 L) was added and stored the solution was stored at −20° C. for 15 h. The dark green supernatant was decanted (~4 L) and the residual suspension was diluted with acetone (500 mL) and filtered through sintered funnel under aspirator vacuum. Filtration was very slow due the fine particle size of the precipitated solid. Washed the solid with acetone (3×300 mL). Partially dried solid was transferred to 250 mL RB flask and dried under high vacuum for 18 hours to obtain 26.3 g Pte_L_Tyr_S0456 (OTL-0038) in 96.9% purity. The supernatant decanted earlier was filtered separately under aspirator vacuum, washed with acetone (3×80 mL) and dried under high vacuum for 15 hours to obtain 3.5 g Pte_L_Tyr_S0456 (OTL-0038). (FIGS. 1, 5 and 21)

Example 17

Low-Pressure Purification of Pte_L_Tyr_S0456 (OTL-0038)

Crude product as described above, such as Example 1, is dissolved into water buffered with a modifier such as sodium acetate, ammonium acetate, sodium phosphate monobasic, or sodium phosphate dibasic at a pH range of about 5- to about 10. The solution is loaded onto a column and is eluted with a gradient comprised of acetonitrile and buffer including a proportion of 0% acetonitrile to 20% acetonitrile. When completed the column is equilibrated with buffer solution.

The crude product may also be loaded in a buffered water solution and then eluted with water, water/acetonitrile 0%-20% followed by equilibration with water and buffer following the elution of the product.

Desired fractions are isolated via removal of excess water by usual techniques including but not limited to rotary evaporation, lyophilization and falling film evaporation. Fractions not meeting acceptance criteria may be recycled using the above purification.

Example 18

High-Pressure Purification of Pte_L_Tyr_S0456 (OTL-0038)

The crude product is dissolved in water (9:1) and is injected (i.e., approximately 5 to approximately 10 grams) onto a 1.4 kg C4 10 micron (or a bonded phase up to C18) column. The product is eluted using a gradient 0-50% comprising a buffered water (10 .mu.m sodium phosphate at pH 6.5) and acetonitrile. Desired fractions are isolated via removal of excess water by techniques well developed in the art, including but not limited to rotary evaporation, lyophilization and falling film evaporation. Fractions not meeting acceptance criteria may be recycled using the same purification method. Isolated fractions may be desalted per the low pressure purification technique outlined above.

Example 19

In Vitro Pharmacology Studies of OTL-0038 and OTL-0039 (D-isomer of OTL-0038)

Two ligand-NIR compounds were developed and designated OTL-0038 and OTL-0039. OTL-0038 compound refers to PTE-L-Tyr-S0456, where pteroyl, the ligand is conjugated to L-tyrosine, which is linked to S0456. OTL-0039 is the D-isomer of OTL-0038. The binding affinity and binding specificity of both compounds for folate receptors were examined in comparison to folic acid, the compound ligand for folate receptors.

A. Material and Methods

KB cells (a human nasopharyngeal cell line) were obtained from American type culture collection (Rockville, Md.) and grown as a monolayer using folate free 1640 RPMI medium containing (Gibco, N.Y.) 10% heat-inactivated fetal bovine serum (Atlanta Biological, Ga.) and 1% penicillin streptomycin (Gibco, N.Y.) in a 5% carbon dioxide: 95% air-humidified atmosphere at 37° C. for at least six passages before they were used for the assays.

KB cells that overexpress FR-.alpha. were seeded in 24-well (100,000 cells/well) Falcon plates (BD Biosciences, Calif.) and allowed to form monolayers over a period of 12 hours. Spent medium in each well was combined with 10 nM of [$^3$H] folic acid (tritiated folic acid) in the presence of increasing concentration (0.1 nM-1 .mu.M) of the OTL-0039 (D-isomer) and OTL-0038 (L-isomer), or folic acid (Sigma-Aldrich, Mo.) in fresh medium (0.5 mL). After incubating for 1 hour at 37° C., cells were rinsed with PBS (3×0.5 mL, Gibco, N.Y.) to remove any unbound radioactive materials. After adding 0.25 M sodium hydroxide (0.5 mL) and incubating for 12 hours at 4° C., cells were transferred into individual scintillation vials containing Ecolite scintillation cocktail (3.0 mL, MP Biomedicals, Ohio) and counted in a liquid scintillation analyzer (Packard). The relative binding affinities were calculated using a plot of % cell bound radioactivity versus the log concentration of the test article using GraphPad Prism 4.

B. Results

The dissociation constants ($K_d$) derived from the studies was calculated to be 81.8 nM, 10.4 nM, and 7.4 nM for OTL-0039, OTL-0038, or folic acid respectively. Relative binding affinities were calculated to be 0.09, 0.71, and 1 for OTL-0039, OTL-0038, and folic acid respectively. All three test articles competed quantitatively with [$^3$H] folic acid.

Relative binding affinity is defined as the molar ratio of the compound required to displace 50% of [$^3$H] folic acid bound to folate receptor on cells; relative affinity of folic acid=1; relative affinity<1 indicates weaker affinity for folate receptor; relative affinity>1 indicates stronger binding to folate receptor.

C. Conclusion

OTL-0038 has affinity for folate receptor and it compares well with the binding affinity of folic acid (10.4 nM Vs 7.4 nM). On the other hand, OTL-0039 has lower affinity for folate receptor when compared to folic acid and OTL-0038. OTL-0038 competed well with [$^3$H] folic acid indicating that folate receptor constitutes the sole OTL-0038 binding site on cancer cells and it is highly specific for folate receptor.

Example 21

Whole Body Imaging and Biodistribution of OTL-0038 And OTL-0039 (D-Isomer of OTL-0038) in Mice Bearing Folate Receptor-Positive Tumor Xenografts The folate receptor positive tumor uptake of OTL-0038 (PTE-L-Tyr-S0456) and OTL-0039 (PTE-D-Tyr-S0456) was examined to determine how well both compounds were taken up by target receptors on tumors. The tissue biodistribution of the compounds were also examined. Both properties were examined in mice two and a half hours following intravenous administration of the compounds.

A. Material and Methods

Cell Culturing and Animal Preparation

KB cells (a human nasopharyngeal cell line) were obtained from American type culture collection (Rockville, Md.) and grown as a monolayer using folate free 1640 RPMI medium containing (Gibco, N.Y.) 10% heat-inactivated fetal bovine serum (Atlanta Biological, Ga.) and 1% penicillin streptomycin (Gibco, N.Y.) in a 5% carbon dioxide: 95% air-humidified atmosphere at 37° C. for at least six passages before they were used for the assays.

Athymic female nude (nu/nu) mice (5 weeks old, 18-20 g) were purchased from Harlan Laboratories (Indianapolis, Ind.) and maintained on gamma-irradiated folate-deficient special diet (Teklad, Wis.) for at least 2 weeks before the start of the study. Animals were housed 5/cage in a barrier, pathogen-free cloaked rack. Autoclaved tap water and food were given as needed. The animals were housed in a sterile environment on a standard 12 hour light-dark cycle for the duration of the study. Mice were identified individually by ear punch. All animal procedures were approved by Purdue Animal Care and Use Committee. Animal care and studies were performed according to national and international guidelines for the humane treatment of animals.

Whole Body Imaging

Seven-week-old female nu/nu mice were inoculated subcutaneously with KB cells (1.0×10$^6$/mouse in folate free RPMI 1640 medium) on the shoulder. Growth of the tumors was measured in perpendicular directions every 2 days using a caliper (body weights were monitored on the same schedule), and the volumes of the tumors were calculated as 0.5× L×W.sup.2 (L=longest axis and W=axis perpendicular to L in millimeters). Once tumors reached between 400 and 500 mm$^3$ in volume, animals (5 mice/group) were intravenously injected with 10 nmol of OTL-0038 or OTL-0039 in phosphate buffered saline (100 μL). After 2.5 hours, animals were euthanized by CO$_2$ asphyxiation. Whole body imaging (intact tumor) experiments were then performed using a Caliper IVIS Lumina II Imaging Station with Living Image 4.0 software (PerkinElmer Inc, Mass.). Settings for imaging:-lamp level: medium; excitation: 745 nm; emission: ICG (indocyanine green); epi illumination; binning: 4 (M), FOV=12.5; f-stop=2; acquisition time=1 s.

Tissue Biodistribution

Following whole body imaging, animals were dissected and selected tissues (heart, lung, liver, spleen, kidneys, stomach, small intestine, large intestine, muscle, skin, tumor) were analyzed for fluorescence activity using IVIS imager as before. Settings for imaging:-lamp level: medium; excitation: 745 nm; emission: ICG; epi illumination; binning: 4 (M), FOV=12.5; f-stop=2; acquisition time=1 s.

B. Results

Whole Body Imaging

OTL-0038 accumulated predominantly in the folate receptor positive tumors, with no substantial fluorescence activity in the other tissues.

Tissue Biodistribution

Analysis of tissue biodistribution was performed on the same animals that were subjected to whole body imaging by euthanizing each mouse, removing their organs and imaging using IVIS imager. The highest fluorescence intensity was observed in FR-positive tumors with no accumulation in the other tissues except the kidneys. Uptake of OTL-0038 in the kidneys was anticipated, since the apical membrane of the proximal tubule of the kidney has been known to express high levels of folate receptor. Moreover, it is possible that the probes are excreted through the kidneys due to their low molecular weights and half-life (most of the folate compounds have <30 min half-life).

C. Conclusion

OTL-0038 mainly accumulated in folate receptor positive tumor xenografts and kidneys. All the other normal tissues displayed minimal levels or no uptake, resulting in excellent tumor-to-normal tissue fluorescence ratios.

Example 23

Comparative Analysis of OTL-0038 (L-isomer) with Folate Derived Near IR Agents

The whole body imaging and tissue biodistribution of OTL-0038 was compared to folate-LS288, folate-IR800, and folate-ZW800. These compounds were conjugated to folate and commercially available near-infrared dyes, LS288, IR800, and ZW800.

A. Material and Methods

Cell Culture and Mouse Preparation

KB cells (a human nasopharyngeal cell line) were obtained from American type culture collection (Rockville, Md.) and grown as a monolayer using folate free 1640 RPMI medium containing (Gibco, N.Y.) 10% heat-inactivated fetal bovine serum (Atlanta Biological, Ga.) and 1% penicillin streptomycin (Gibco, N.Y.) in a 5% carbon dioxide: 95% air-humidified atmosphere at 37° C. for at least six passages before they were used for the assays.

Athymic female nude mice (5 weeks old, 18-20 g) were purchased from Harlan Laboratories (Indianapolis, Ind.) and maintained on gamma-irradiated folate-deficient special diet (Teklad, Wis.) for at least 2 weeks before the start of the study. Animals were housed 5/cage in a barrier, pathogen-free cloaked rack. Autoclaved tap water and food were given as needed. The animals were housed in a sterile environment on a standard 12 hour light-dark cycle for the duration of the study. Mice were identified individually by ear punch. All animal procedures were approved by Purdue Animal Care and Use Committee. Animal care and studies were performed according to national and international guidelines for the humane treatment of animals.

Whole Body Imaging

Seven-week-old female nu/nu mice were inoculated subcutaneously with KB cells ($1.0 \times 10^6$/mouse in folate free RPMI 1640 medium) on the shoulder. Growth of the tumors was measured In perpendicular directions every 2 days using a caliper (body weights were monitored on the same schedule), and the volumes of the tumors were calculated as 0.5× L×W (L=longest axis and W=axis perpendicular to L in millimeters). Once tumors reached between 400 and 500 mm$^3$ in volume, animals (5 mice/group) were intravenously injected with 10 nmol of OTL-0038 or OTL-0039 in phosphate buffered saline (100 µL). After 2.5 hours, animals were euthanized by $CO_2$ asphyxiation. Whole body imaging (intact tumor) experiments were then performed using a Caliper IVIS Lumina II Imaging Station with Living Image 4.0 software (PerkinElmer Inc, Mass.). Settings for imaging:-lamp level: medium; excitation: 745 nm; emission: ICG(indocyanine green); epi illumination; binning: 4 (M), FOV=12.5; f-stop=2; acquisition time=1 s.

Tissue Biodistribution

Following whole body imaging, animals were dissected and selected tissues (heart, lung, liver, spleen, kidneys, stomach, small intestine, large intestine, muscle, skin, tumor) were analyzed for fluorescence activity using IVIS imager as before. Settings for imaging:-lamp level: medium; excitation: 745 nm; emission: ICG; epi illumination; binning: 4 (M), FOV=12.5; f-stop=2; acquisition time=1 s.

B. Results

Whole Body Imaging

As seen in the FIG. 5, OTL-0038 (L-isomer), folate-LS288, folate-IR800, folate-ZW800 accumulated predominantly in the folate receptor positive tumors, with no substantial fluorescence activity in the other tissues. Moreover, direct comparison demonstrated that tumor fluorescence intensity OTL-0038 injected mice were brighter (higher) than the mice treated with the other folate-conjugated near IR dyes (FIG. 6).

Tissue Biodistribution

Figure 7:
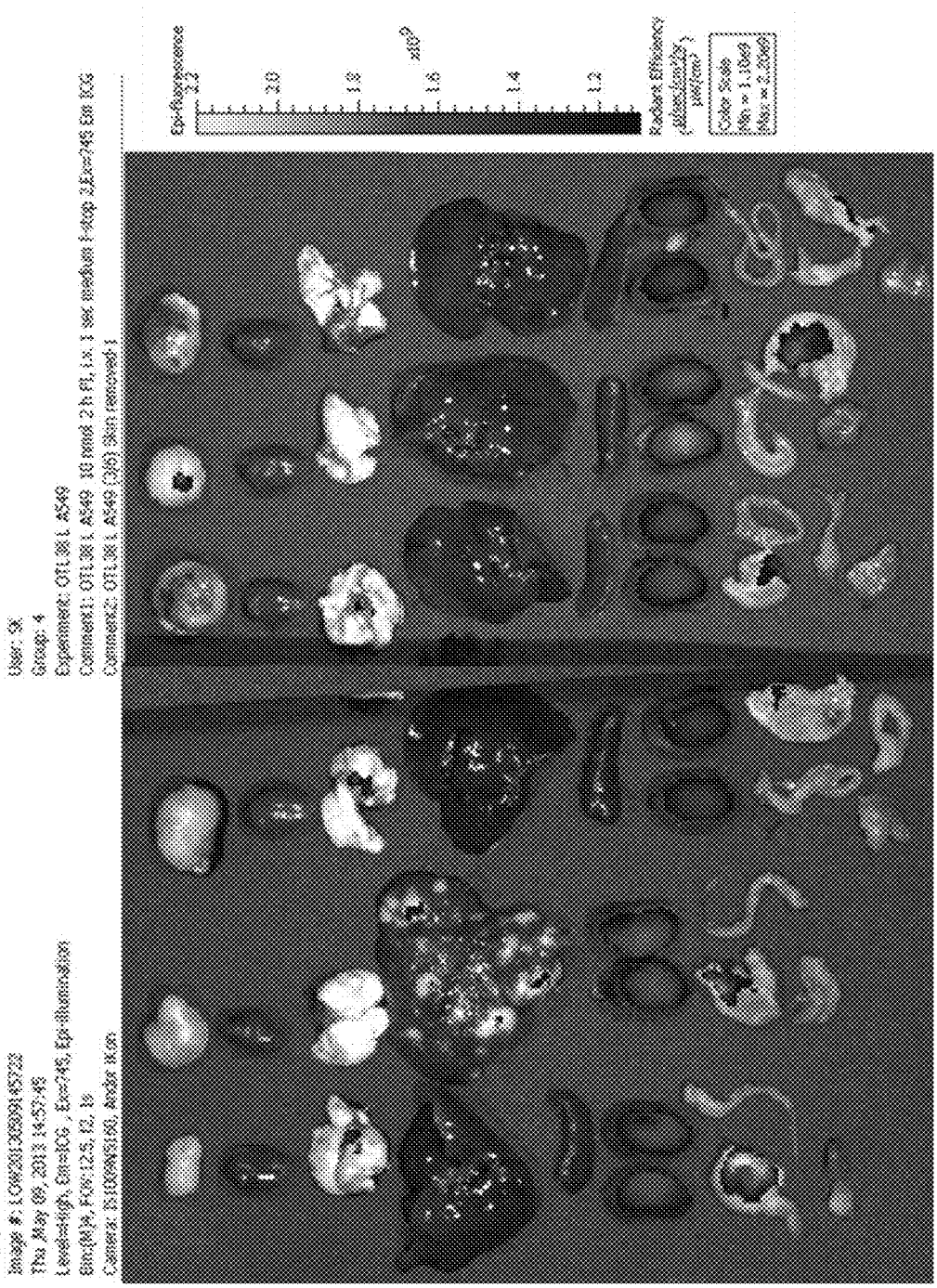
FIG. 7 illustrates invasive tumor and kidney uptake of OTL-0038, by folate receptor-negative tumor xenografts (A549 tumor xenografts) and folate receptor-positive kidneys. Data analysis was performed 2.5 hours post injection.
Figure 8A:
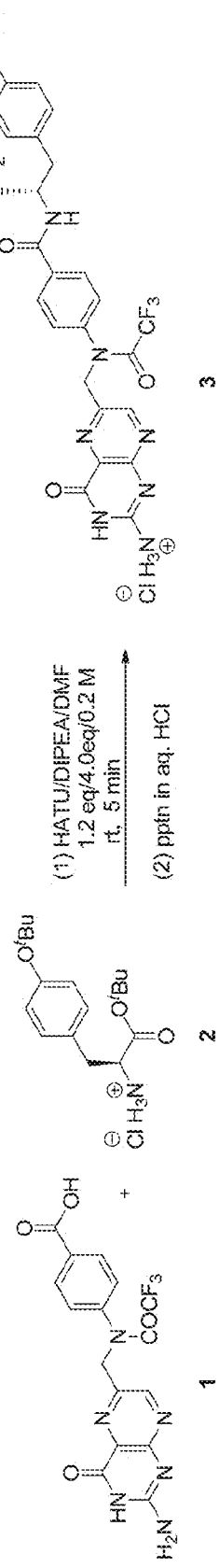
FIG. 8 illustrates a solid-phase synthesis of TFA-Pteroyl-Tyr LCMS of the crude TFA-Pteroyl_Tyr (0-50B pH 7).
Figure 8B:
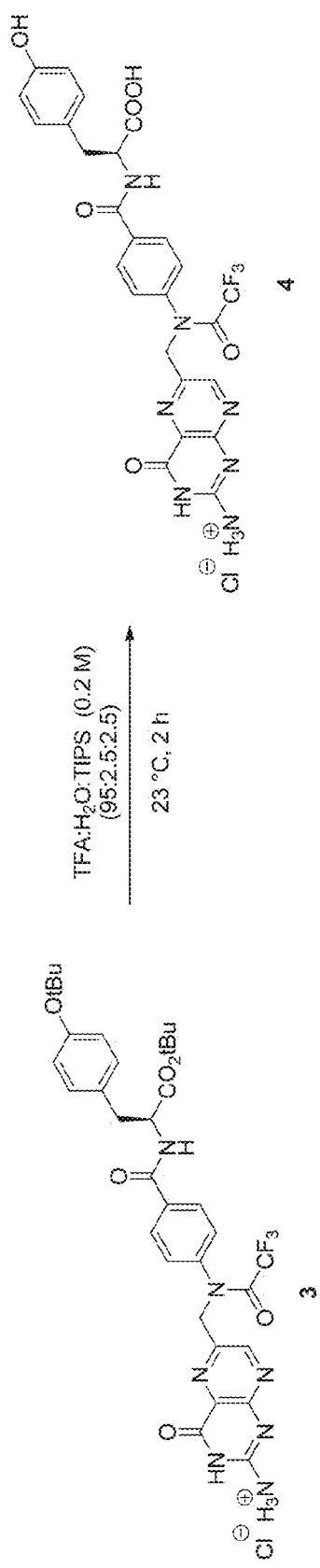
Figure 10:
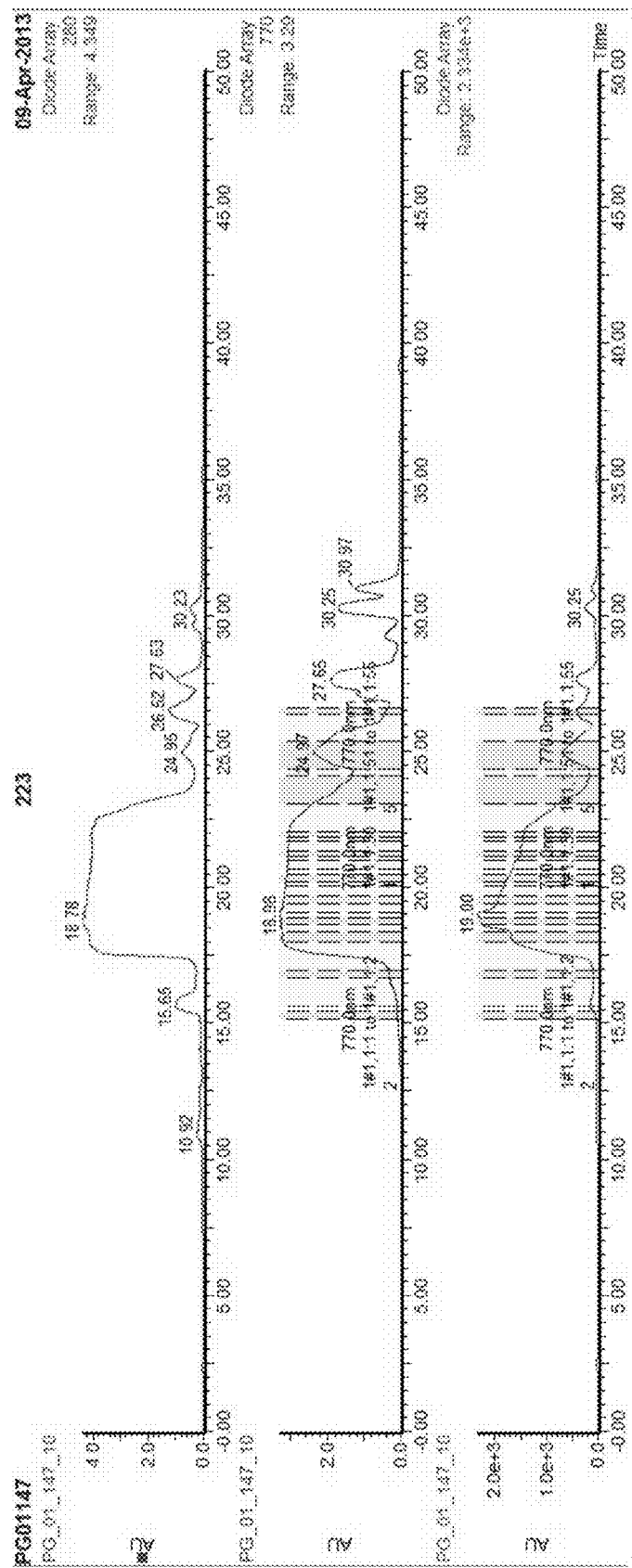
FIG. 10 displays a preparative chromatogram profile of coupling reaction for OTL-0038.

Analysis of tissue biodistribution was performed on the same animals that were subjected to whole body imaging by euthanizing each mouse, removing their organs and imaging them using an IVIS imager. As seen in the FIG. 7, the highest fluorescence intensity was observed in FR-positive tumors and the kidneys. The kidney uptake was anticipated since the apical membrane of the proximal tubule of the kidney has been known to express high levels of folate receptor. Moreover, it's possible that the probes are excreted through the kidneys due to their low molecular weights and half-life (most of the folate compounds have <30 min half-life).

C. Conclusion

OTL-0038 has beneficial aspects relative to folate-LS288, folate-IR800, and folate-ZW800 in tumor accumulated fluorescence intensity. OTL-0038 may be brighter than other commercially available near IR dyes such as LS288, IR800, and ZW800.

Example 24

Whole Body Imaging and Biodistribution of OTL-0038 in Mice Bearing Folate Receptor-Negative Tumor Xenografts Whole body imaging and tissue biodistribution was performed to determine the in vivo specificity of OTL-0038 for folate receptors. Experiments used mice harboring a tumor that is negative for folate receptors to characterize the specificity of OTL-038 compound for folate receptors.

A. Material and Methods

Cell Culture and Mouse Preparation

A549 cells (a alveolar basal epithelial carcinoma cell line) were obtained from American type culture collection (Rockville, Md.) and grown as a monolayer using 1640 RPMI medium containing (Gibco, N.Y.) 10% heat-inactivated fetal bovine serum (Atlanta Biological, Ga.) and 1% penicillin streptomycin (Gibco, N.Y.) in a 5% carbon dioxide: 95% air-humidified atmosphere at 37° C. for at least six passages before they were used for the assays.

Athymic female nude (nu/nu) mice (6 weeks old, 18-20 g) were purchased from Harlan Laboratories (Indianapolis, Ind.) and maintained on normal diet (Teklad, Wis.). Animals were housed 5/cage in a barrier, pathogen-free cloaked rack. Autoclaved tap water and food were given as needed. The animals were housed in a sterile environment on a standard 12 hours light-dark cycle for the duration of the study. Mice were identified individually by ear punch. All animal procedures were approved by Purdue Animal Care and Use Committee. Animal care and studies were performed according to national and international guidelines for the humane treatment of animals.

Whole Body Imaging

Seven-week-old female nu/nu mice were inoculated subcutaneously with A549 cells ($1.0 \times 10^6$/mouse in RPMI 1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm³ in volume, animals (6 mice/group) were intravenously injected with 10 nmol of OTL-0038 in phosphate buffered saline (100 µL). After 2.5 h, animals were sacrificed by $CO_2$ asphyxiation. Whole body imaging (intact tumor) experiments were then performed using a Caliper IVIS Lumina II Imaging Station with Living Image 4.0 software (PerkinElmer Inc, Mass.). Settings for imaging:-lamp level: medium; excitation: 745 nm; emission: ICG (indocyanine green); epi illumination; binning: 4 (M), FOV=12.5; f-stop=2; acquisition time=1 s.

Tissue Biodistribution

Following whole body imaging, animals were dissected and selected tissues (heart, lung, liver, spleen, kidneys, stomach, small intestine, large intestine, muscle, skin, tumor) were analyzed for fluorescence activity using IVIS imager as before. Settings for imaging:-lamp level: medium; excitation: 745 nm; emission: ICG; epi illumination; binning: 4 (M), FOV=12.5; f-stop=2; acquisition time=1 s.

B. Results

Whole Body Imaging

As seen in the FIG. 5, OTL-0038 did not accumulated in the folate receptor negative tumors and there was no substantial fluorescence activity in the other tissues except kidneys.

Invasive Tumor and Kidney Uptake

Analysis of tumor and kidney accumulation was performed on the same animals that were subjected whole body imaging by euthanizing each mouse, removing their organs and imaging using IVIS imager. As we anticipated, no fluorescence was observed in folate receptor negative tumors there was high kidney uptake. Since the apical membrane of the proximal tubule of the kidney has been known to express high levels of FR, kidney uptake is expected. Moreover, it's possible that the probes are excreted through the kidneys due to their low molecular weights and half-life (most of the folate compounds have <30 min half-life).

C. Conclusion

OTL-0038 is highly specific for folate receptor.

The invention claimed is:
1. A method for synthesizing a compound of the formula:

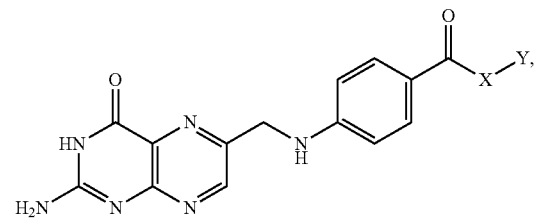

or a racemic mixture thereof, wherein:
X is selected from the group consisting of:

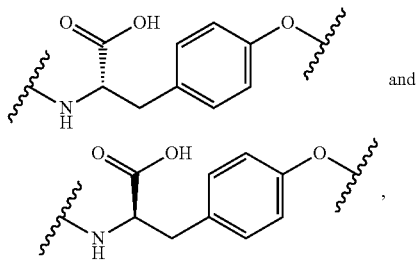

or a racemic mixture thereof; and
Y is represented by the formula:

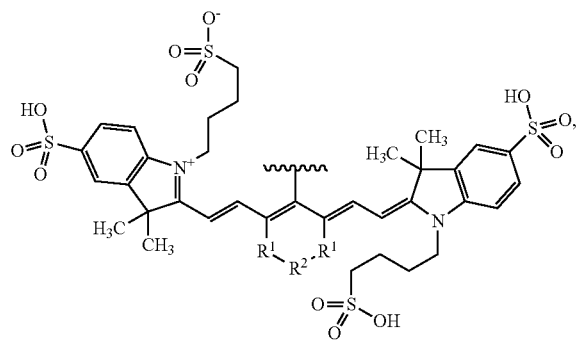

wherein:
$R^1$ is independently selected from the group consisting of O, S, NH, $CH_2$ and $CH_2CH_2$; and
$R^2$ is independently selected from the group consisting of $CH_2$ and $CH_2CH_2$;
comprising the steps of:
(a) reacting a compound of the formula 1:

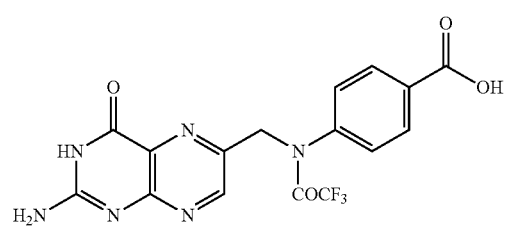

with a compound of the formula:

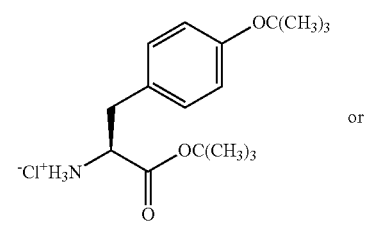

-continued

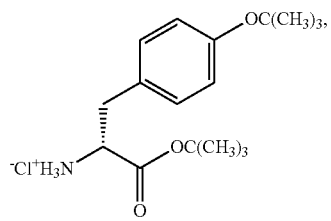

or a racemic mixture thereof, in the presence of a polar solvent and trifluoroacetic acid to provide a compound of the formula:

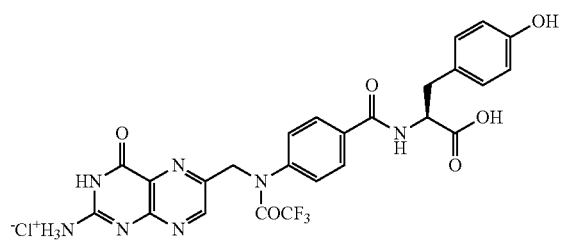

or

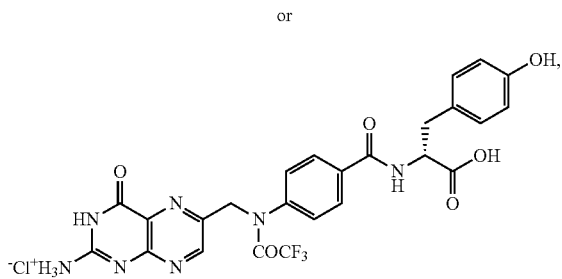

or a racemic mixture thereof;

(b) reacting the compound of the formula:

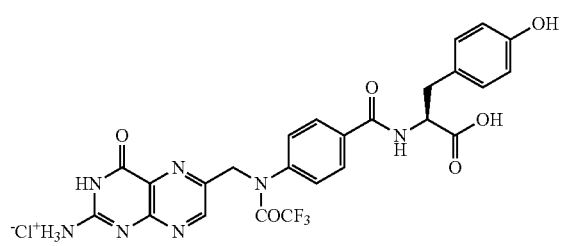

or

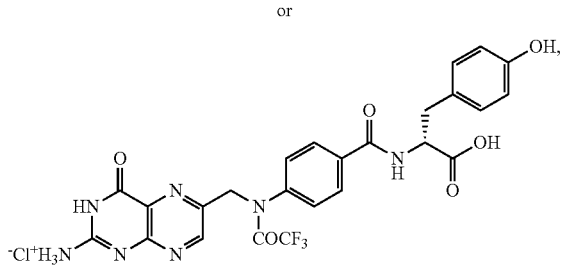

or a racemic mixture thereof;

with sodium hydroxide and a dye compound of the formula:

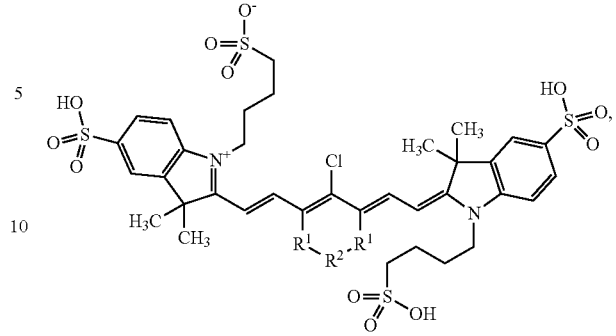

wherein:
R$^1$ is independently selected from the group consisting of O, S, NH, CH$_2$ and CH$_2$CH$_2$; and
R$^2$ is independently selected from the group consisting of CH$_2$ and CH$_2$CH$_2$; and (c) isolating the compound of the formula:

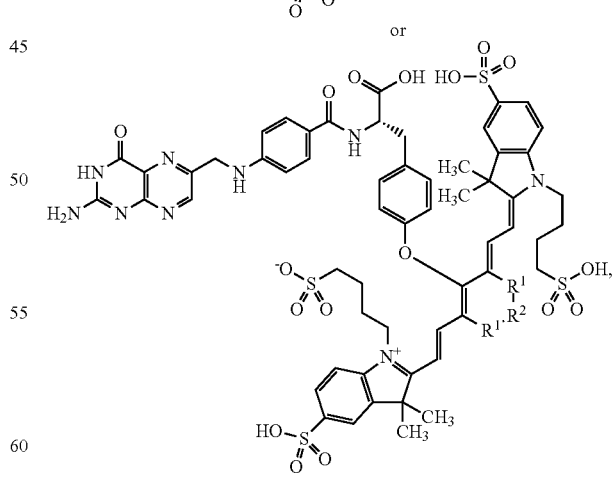

or a racemic mixture thereof, wherein:
R$^1$ is independently selected from the group consisting of O, S, NH, CH$_2$ and CH$_2$CH$_2$; and R[2] is independently selected from the group consisting of $CH_2$ and $CH_2CH_2$.

2. The method of claim 1, wherein the dye compound in step (b) is selected from the group consisting of:

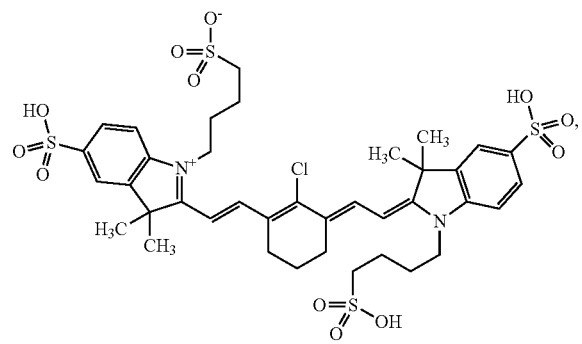

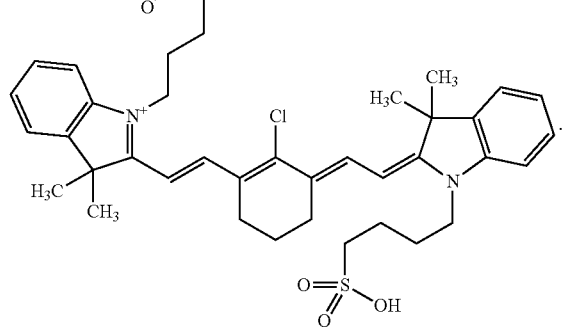

3. The method of claim 1, wherein the polar solvent is selected from the group consisting of dimethylformamide, dimethylsulfoxide and water.

4. A method for synthesizing a compound of the formula:

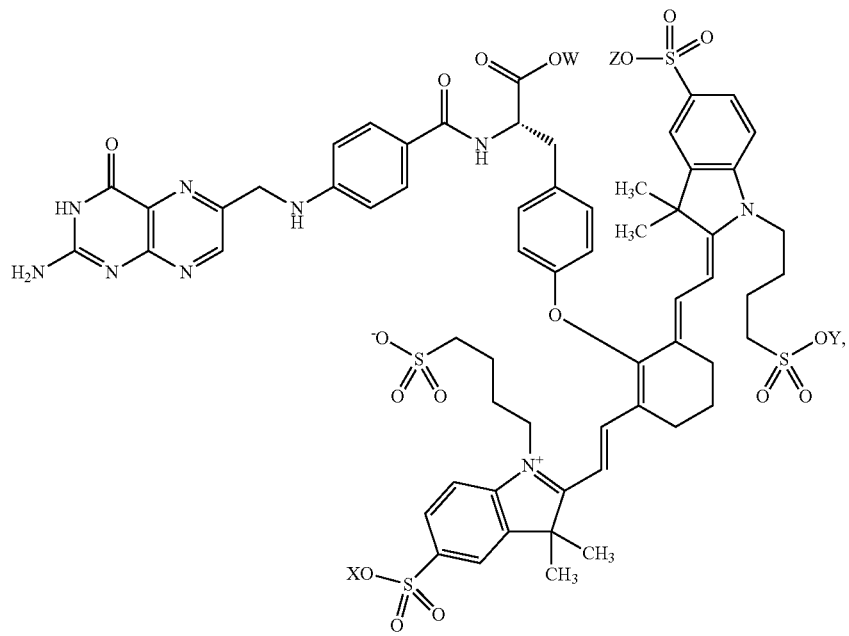

wherein:

W, X, Y and Z are independently selected from the group consisting of $H^+$, $Na^+$, $K^+$ or $NH_4^+$;

comprising the steps of:

(a) reacting a compound of the formula:

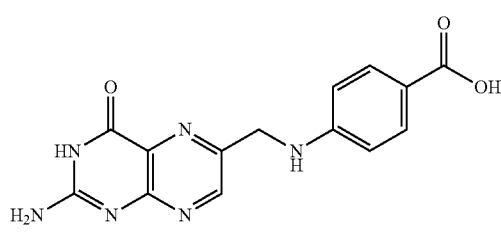 [SMILES: Nc1nc2ncc(CNc3ccc(C(=O)O)cc3)nc2c(=O)[nH]1]

-continued

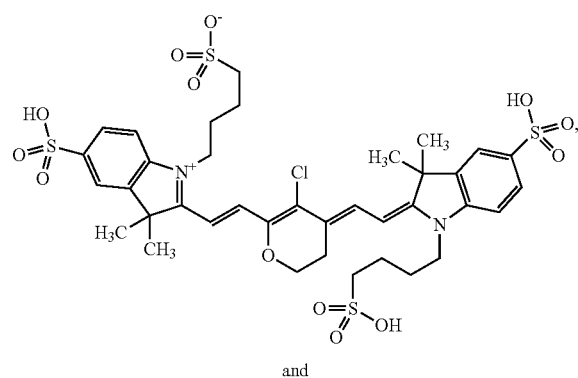

and with a compound of the formula:

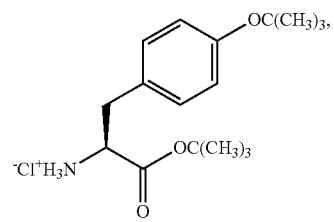

in the presence of dimethylformamide and trifluoroacetic acid to provide a compound of the formula:

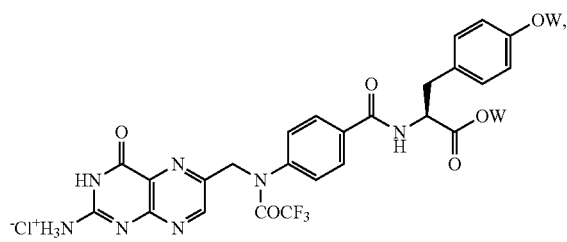

wherein:
W is independently selected from the group consisting of H$^+$, Na$^+$, K$^+$ or NH$_4^+$;

(b) reacting the compound of the formula:

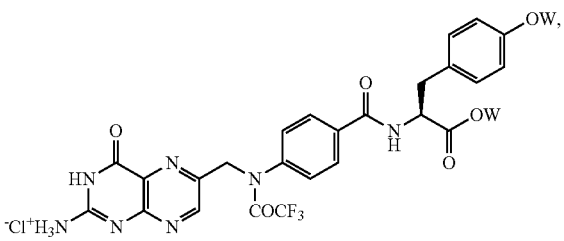

with sodium hydroxide and a dye compound of the formula:

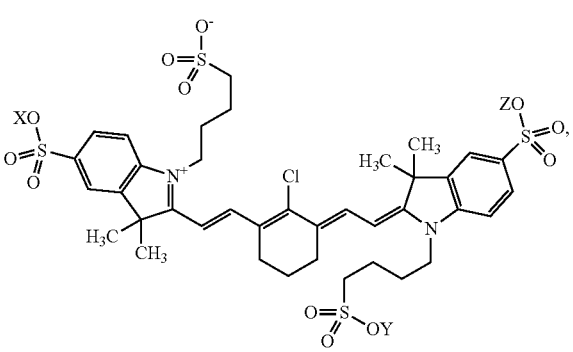

wherein:
X, Y and Z are independently selected from the group consisting of H$^+$, Na$^+$, K$^+$ or NH$_4^+$; and
(c) isolating the compound of the formula:

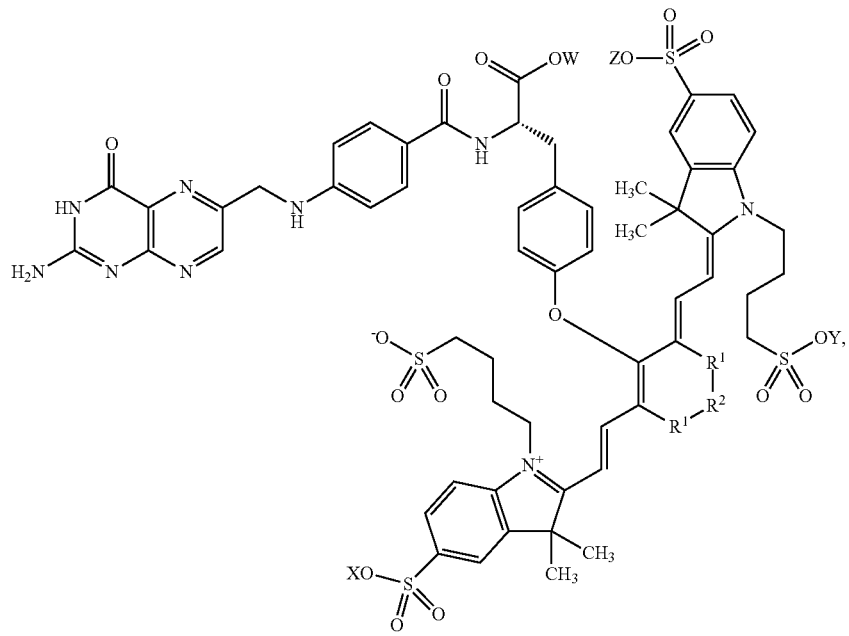

wherein:
W, X, Y and Z are independently selected from the group consisting of $H^+$, $Na^+$, $K^+$ or $NH_4^+$.

5. A method for synthesizing an isotopic form of a compound of the formula:

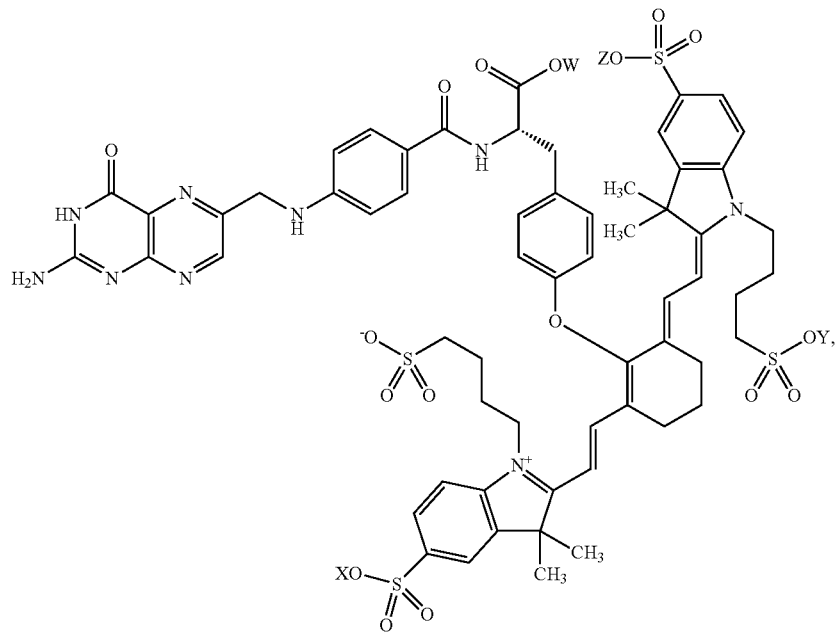

wherein said isotopic form comprises one or more carbon and/or hydrogen isotopes selected from the group consisting of $^2H$, $^3H$, $^{13}C$ and $^{14}C$, and further wherein:
W, X, Y and Z are independently selected from the group consisting of $H^+$, $Na^+$, $K^+$ or $NH_4^+$;
comprising the steps of:

(a) reacting a compound of the formula:

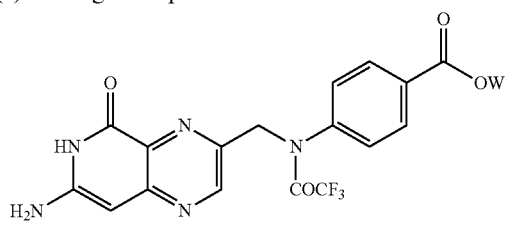

wherein:
W is selected from the group consisting of $H^+$, $Na^+$, $K^+$ or $NH_4^+$;
with an isotopic form of a compound of the formula:

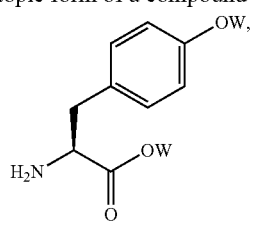

wherein said isotopic form comprises one or more carbon and/or hydrogen isotopes selected from the group consisting of $^2H$, $^3H$, $^{13}C$ and $^{14}C$, and further wherein:
W is selected from the group consisting of $H^+$, $Na^+$, $K^+$ or $NH_4^+$;

in the presence of dimethylformamide to provide an isotopic form of a compound of the formula:

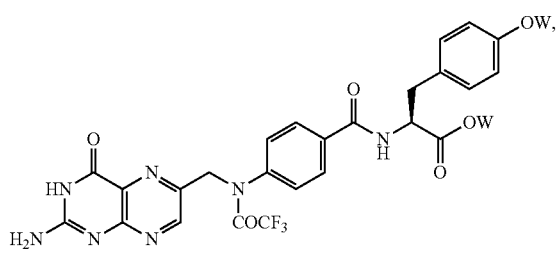

wherein said isotopic form comprises one or more carbon and/or hydrogen isotopes selected from the group consisting of $^2H$, $^3H$, $^{13}C$ and $^{14}C$, and further wherein:
W is selected from the group consisting of $H^+$, $Na^+$, $K^+$ or $NH_4^+$;

(b) reacting the isotopic form of the compound of the formula:

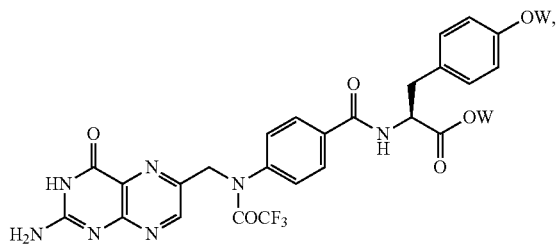

wherein said isotopic form comprises one or more carbon and/or hydrogen isotopes selected from the group consisting of $^2H$, $^3H$, $^{13}C$ and $^{14}C$, and further wherein:

W is selected from the group consisting of $H^+$, $Na^+$, $K^+$ or $NH_4^+$;

with sodium hydroxide and a dye compound of the formula:

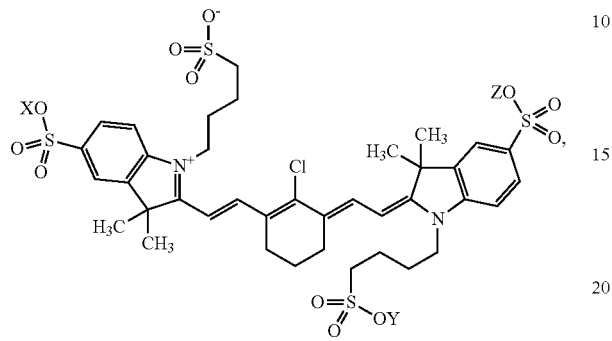

wherein
X, Y and Z are independently selected from the group consisting of $H^+$, $Na^+$, $K^+$ or $NH_4^+$; and (c) isolating the isotopic form of the compound of the formula:

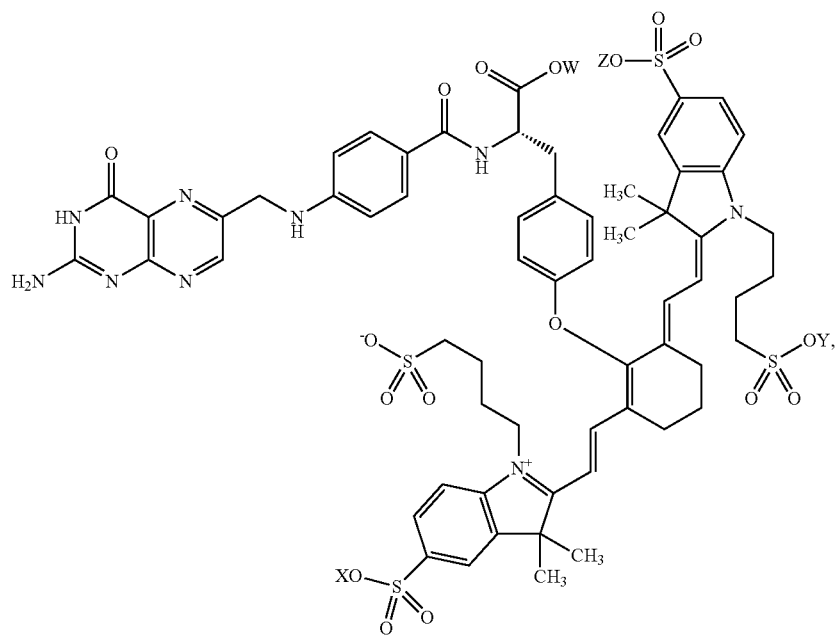

wherein said isotopic form comprises one or more carbon and/or hydrogen isotopes selected from the group consisting of $^2H$, $^3H$, $^{13}C$ and $^{14}C$, and further wherein:

W, X, Y and Z are independently selected from the group consisting of $H^+$, $Na^+$, $K^+$ or $NH_4^+$.

6. A method for the solid phase synthesis of a compound of the formula:

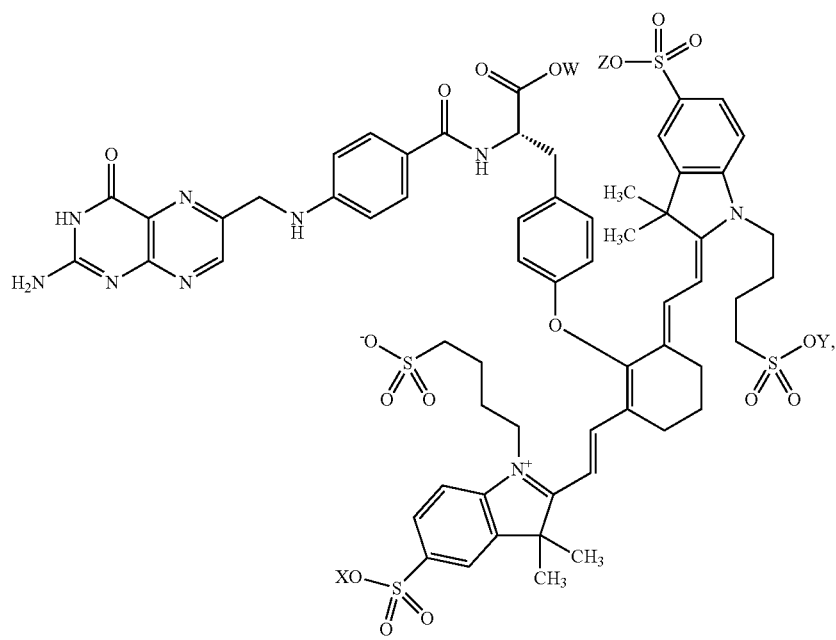

wherein:
W, X, Y and Z are independently selected from the group consisting of H⁺, Na⁺, K⁺ or NH₄⁺;
comprising in a solid phase peptide synthesizer, the steps of:
(a) reacting a compound of the formula:

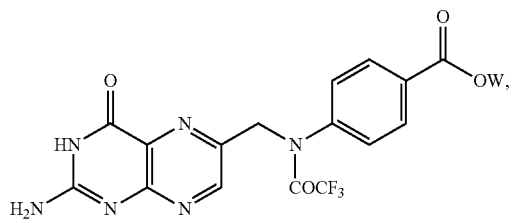

wherein:
W is selected from the group consisting of H⁺, Na⁺, K⁺ or NH₄⁺;
with a compound of the formula:

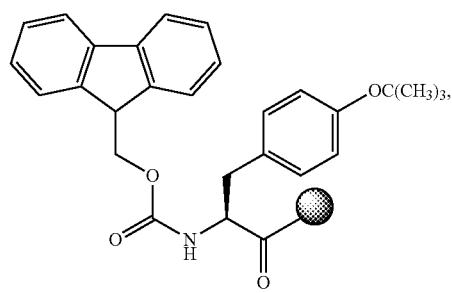

wherein:
🔘 is a resin bead;
in the presence of dimethylformamide to provide a compound of the formula:

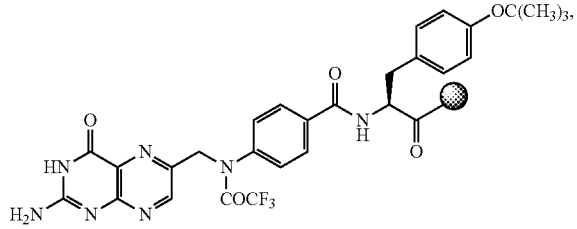

wherein:
🔘 is a resin bead;
(b) reacting the compound of the formula:

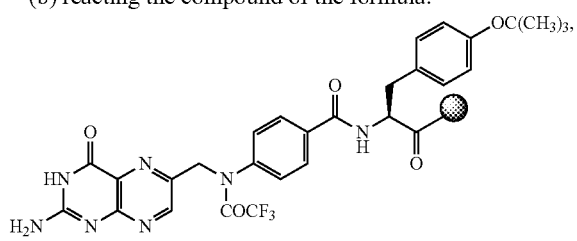

in the presence of trifluoroacetic acid:H₂O:triisopropyl-silyl alcohol to provide a compound of the formula:

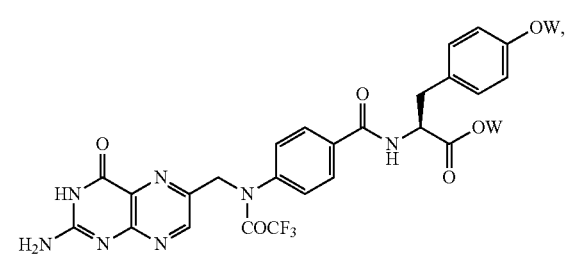

wherein:

W is selected from the group consisting of $H^+$, $Na^+$, $K^+$ or $NH_4^+$;

(c) reacting the compound of the formula:

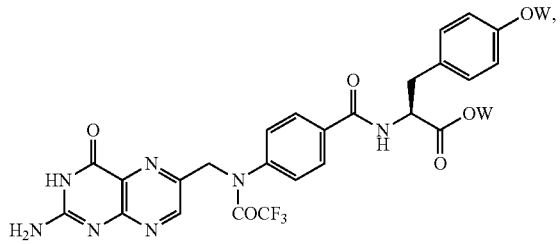

with sodium hydroxide and a dye compound of the formula:

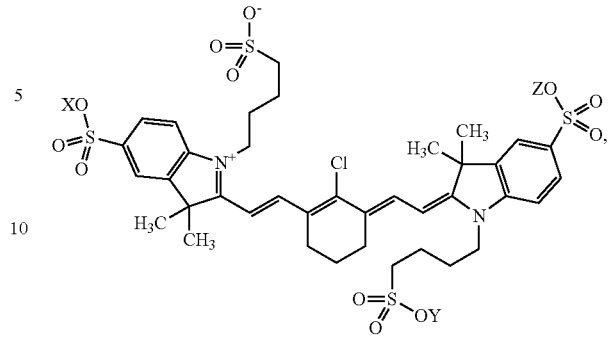

wherein:
X, Y and Z are independently selected from the group consisting of $H^+$, $Na^+$, $K^+$ or $NH_4^+$; and (d) isolating the compound of the formula:

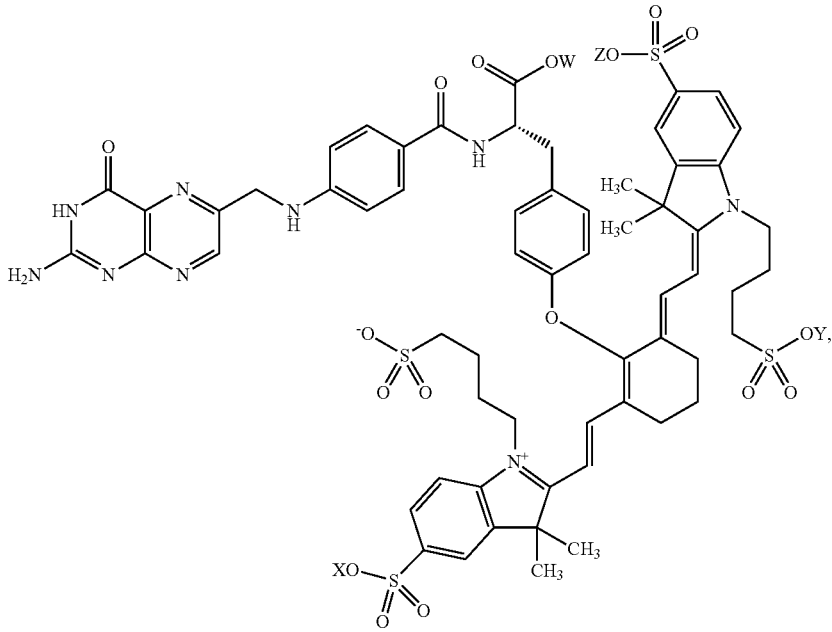

wherein:
W, X, Y and Z are independently selected from the group consisting of $H^+$, $Na^+$, $K^+$ or $NH_4^+$.

* * * * *